US008202845B2

(12) United States Patent
Drumm et al.

(10) Patent No.: US 8,202,845 B2
(45) **Date of Patent: *Jun. 19, 2012**

(54) MEANS AND METHODS FOR THE SPECIFIC MODULATION OF TARGET GENES IN THE CNS AND THE EYE AND METHODS FOR THEIR IDENTIFICATION

(75) Inventors: Karina Drumm, Würzburg (DE); Stefan Hubert Schlör, Marktheidenfeld (DE); Frank Göhring, Würzburg (DE)

(73) Assignee: Acuity Pharmaceuticals, Inc., Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/511,657

(22) PCT Filed: Apr. 16, 2003

(86) PCT No.: PCT/EP03/04003

§ 371 (c)(1),
(2), (4) Date: Apr. 18, 2005

(87) PCT Pub. No.: WO03/087368

PCT Pub. Date: Oct. 23, 2003

(65) Prior Publication Data

US 2006/0003915 A1 Jan. 5, 2006

Related U.S. Application Data

(60) Provisional application No. 60/431,173, filed on Dec. 5, 2002.

(30) Foreign Application Priority Data

Apr. 18, 2002 (EP) .................................... 02008761

(51) Int. Cl.

| | |
|---|---|
| *A61K 31/70* | (2006.01) |
| *C07H 21/02* | (2006.01) |
| *C07H 21/04* | (2006.01) |

(52) U.S. Cl. ..................... 514/44 A; 536/24.1; 536/24.5

(58) Field of Classification Search ........................ None
See application file for complete search history.

(56) References Cited

U.S. PATENT DOCUMENTS 4,235,871 A 11/1980 Papahadjopoulos et al.

(Continued)

FOREIGN PATENT DOCUMENTS

CA 2359180 A1 8/2000

(Continued)

OTHER PUBLICATIONS

Elbashir et al. (2001) Nature 411:494-498.*

(Continued)

*Primary Examiner* — Terra Cotta Gibbs

(74) *Attorney, Agent, or Firm* — Pepper Hamilton LLP

(57) ABSTRACT

Provided are methods for the treatment of disorders of the central nervous system (CNS) and the eye. In particular, use of compositions comprising a compound capable of modulating a target gene or gene product is described for the preparation of a pharmaceutical composition for the treatment of disorders of the CNS and/or the eye, wherein the composition is designed to be administered outside the blood-CNS and the blood-retina barriers. Furthermore, methods are provided for identifying and obtaining nucleic acid molecules encoding polypeptides involved in CNS disorders or of the eye, methods for diagnosing said disorders as well as transgenic animal deficient in the expression of target genes identified in accordance with the described method. In addition, methods of identifying and isolating drugs that are particularly useful for the treatment of disorders related to the CNS and/or the eye are disclosed.

8 Claims, 1 Drawing Sheet fluorescence bright-field

U.S. PATENT DOCUMENTS

| | | | | |
|---|---|---|---|---|
| 4,501,728 | A | 2/1985 | Geho et al. | |
| 4,837,028 | A | 6/1989 | Allen | |
| 4,920,016 | A | 4/1990 | Allen et al. | |
| 5,019,369 | A | 5/1991 | Presant et al. | |
| 5,139,941 | A | 8/1992 | Muzyczka et al. | |
| 5,252,479 | A | 10/1993 | Srivastava | |
| 5,498,521 | A * | 3/1996 | Dryja et al. | 435/6 |
| 5,550,289 | A | 8/1996 | Eppstein et al. | |
| 5,624,803 | A | 4/1997 | Noonberg et al. | |
| 5,639,736 | A | 6/1997 | Robinson | |
| 5,639,872 | A | 6/1997 | Robinson | |
| 5,661,135 | A | 8/1997 | Robinson | |
| 5,683,986 | A | 11/1997 | Carter | |
| 5,712,257 | A | 1/1998 | Carter | |
| 5,801,156 | A | 9/1998 | Robinson et al. | |
| 5,814,620 | A * | 9/1998 | Robinson et al. | 514/44 |
| 5,902,598 | A | 5/1999 | Chen et al. | |
| 6,015,894 | A | 1/2000 | Bennett et al. | |
| 6,020,462 | A | 2/2000 | Semenza | |
| 6,037,329 | A | 3/2000 | Baird et al. | |
| 6,121,000 | A | 9/2000 | Wright et al. | |
| 6,150,092 | A | 11/2000 | Uchida et al. | |
| 6,177,401 | B1 | 1/2001 | Ulrigh et al. | |
| 6,331,313 | B1 | 12/2001 | Wong et al. | |
| 6,355,271 | B1 | 3/2002 | Bell et al. | |
| 6,375,972 | B1 | 4/2002 | Guo et al. | |
| 6,433,145 | B1 | 8/2002 | LaFleur et al. | |
| 6,506,559 | B1 | 1/2003 | Fire et al. | |
| 6,852,510 | B2 | 2/2005 | Bremel et al. | |
| 7,056,704 | B2 | 6/2006 | Tuschl et al. | |
| 7,090,864 | B2 | 8/2006 | Pardridge et al. | |
| 7,148,342 | B2 * | 12/2006 | Tolentino et al. | 536/24.5 |
| 7,345,027 | B2 | 3/2008 | Tolentino et al. | |
| 7,674,895 | B2 | 3/2010 | Reich et al. | |
| 7,750,143 | B2 | 7/2010 | Tolentino et al. | |
| 2001/0021772 | A1 | 9/2001 | Uhlmann et al. | |
| 2002/0054902 | A1 * | 5/2002 | Pardridge | 424/450 |
| 2002/0086356 | A1 | 7/2002 | Tuschl et al. | |
| 2002/0132788 | A1 | 9/2002 | Lewis et al. | |
| 2002/0162126 | A1 | 10/2002 | Beach et al. | |
| 2002/0165158 | A1 * | 11/2002 | King | 514/12 |
| 2002/0173478 | A1 | 11/2002 | Gewirtz | |
| 2003/0138407 | A1 | 7/2003 | Lu et al. | |
| 2003/0153519 | A1 | 8/2003 | Kay et al. | |
| 2003/0216335 | A1 | 11/2003 | Lockridge et al. | |
| 2004/0018176 | A1 | 1/2004 | Tolentino et al. | |
| 2004/0018716 | A1 | 1/2004 | Kitou et al. | |
| 2004/0096848 | A1 | 5/2004 | Thru et al. | |
| 2004/0115640 | A1 | 6/2004 | Myers et al. | |
| 2004/0180357 | A1 | 9/2004 | Reich et al. | |
| 2004/0220129 | A1 | 11/2004 | Reich et al. | |
| 2004/0248174 | A1 | 12/2004 | Reich et al. | |
| 2004/0259247 | A1 | 12/2004 | Tuschl et al. | |
| 2005/0019927 | A1 | 1/2005 | Hildinger et al. | |
| 2005/0048529 | A1 | 3/2005 | McSwiggen | |
| 2005/0159380 | A1 | 7/2005 | Guerciolini et al. | |
| 2005/0187174 | A1 | 8/2005 | Richards et al. | |
| 2005/0197315 | A1 | 9/2005 | Taira et al. | |
| 2005/0222061 | A1 | 10/2005 | Schulte | |
| 2005/0246794 | A1 | 11/2005 | Khvorova et al. | |
| 2006/0003915 | A1 | 1/2006 | Drumm et al. | |
| 2006/0094032 | A1 | 5/2006 | Fougerolles et al. | |
| 2006/0182783 | A1 | 8/2006 | Hughes et al. | |
| 2006/0217332 | A1 | 9/2006 | Vargeese et al. | |
| 2006/0223770 | A1 | 10/2006 | Fougerolles et al. | |
| 2006/0286073 | A1 | 12/2006 | Tolentino et al. | |
| 2006/0292120 | A1 | 12/2006 | Tolentino et al. | |
| 2007/0003523 | A1 | 1/2007 | Tolentino et al. | |
| 2007/0037760 | A1 | 2/2007 | Tolentino et al. | |
| 2007/0037761 | A1 | 2/2007 | Tolentino et al. | |
| 2007/0037762 | A1 | 2/2007 | Tolentino et al. | |
| 2007/0149471 | A1 | 6/2007 | Reich et al. | |
| 2007/0178068 | A1 | 8/2007 | Reich et al. | |
| 2008/0188437 | A1 | 8/2008 | Tolentino et al. | |
| 2009/0061478 | A1 | 3/2009 | Reich et al. | |
| 2009/0104259 | A1 | 4/2009 | Tolentino et al. | |
| 2010/0168207 | A1 | 7/2010 | Tolentino et al. | |
| 2011/0021605 | A1 | 1/2011 | Schulte et al. | |

FOREIGN PATENT DOCUMENTS

| | | | |
|---|---|---|---|
| EP | 0308066 | A2 | 3/1989 |
| EP | 1229134 | A2 | 8/2002 |
| EP | 1578933 | B1 | 3/2010 |
| IL | 166274 | | 9/2010 |
| NZ | 537833 | | 12/2010 |
| WO | WO93/24641 | A2 | 12/1993 |
| WO | WO 94/08026 | A1 | 4/1994 |
| WO | WO94/13788 | A1 | 6/1994 |
| WO | WO94/24274 | A1 | 10/1994 |
| WO | WO95/04142 | A2 | 2/1995 |
| WO | WO 97/18855 | A1 | 5/1997 |
| WO | WO 97/20579 | A2 | 6/1997 |
| WO | WO 98/22132 | A1 | 5/1998 |
| WO | WO 98/48009 | A2 | 10/1998 |
| WO | WO 98/56361 | A1 | 12/1998 |
| WO | WO 99/12572 | A1 | 3/1999 |
| WO | WO00/08141 | A2 | 2/2000 |
| WO | WO00/44895 | A1 | 8/2000 |
| WO | WO 00/44914 | A | 8/2000 |
| WO | WO 00/63364 | A2 | 10/2000 |
| WO | WO 01/36646 | A | 5/2001 |
| WO | WO01/52904 | A2 | 7/2001 |
| WO | WO01/57206 | A2 | 8/2001 |
| WO | WO01/68836 | A2 | 9/2001 |
| WO | WO 01/75164 | A2 | 10/2001 |
| WO | WO 01/82900 | A1 | 11/2001 |
| WO | WO 01/83729 | A | 11/2001 |
| WO | WO 01/98522 | A2 | 12/2001 |
| WO | WO02/08242 | A1 | 1/2002 |
| WO | WO 02/11666 | A2 | 2/2002 |
| WO | WO02/44321 | A2 | 6/2002 |
| WO | WO 02/083184 | A2 | 10/2002 |
| WO | WO 02/088320 | A | 11/2002 |
| WO | WO02/096927 | A2 | 12/2002 |
| WO | WO02/096957 | A1 | 12/2002 |
| WO | WO03/012105 | A2 | 2/2003 |
| WO | WO03/066805 | A2 | 8/2003 |
| WO | WO03/070910 | A2 | 8/2003 |
| WO | WO03/087367 | A2 | 10/2003 |
| WO | WO03/087368 | A2 | 10/2003 |
| WO | WO03/099298 | A1 | 12/2003 |
| WO | WO2004/009769 | A2 | 1/2004 |
| WO | WO 2004/013310 | A2 | 2/2004 |
| WO | WO2004/065546 | A2 | 8/2004 |
| WO | WO2004/094606 | A2 | 11/2004 |
| WO | WO2005/028649 | A1 | 3/2005 |
| WO | WO2006/110813 | A2 | 10/2006 |
| WO | WO2007/067981 | A2 | 6/2007 |
| WO | WO2007/146953 | A2 | 12/2007 |
| WO | WO2008/030996 | A2 | 3/2008 |
| WO | WO2008/110777 | A2 | 9/2008 |

OTHER PUBLICATIONS

Weber et al. (1991) Nucleic Acids Res. 19:6263-6268.*

Epstein (1998) Methods: A Companion to Methods in Enzymology 14:21-33.*

Collins et al. (1992) "The human beta-subunit of rod photoreceptor cGMP phosphodiesterase: complete retinal cDNA sequence and evidence for expression in brain" Genomics 13 (3): 698-704.*

Dryja et al. (1995) "Mutations in the gene encoding the alpha subunit of the rod cGMP-gated channel in autosomal recessive retinitis pigmentosa" PNAS 92:10177-10181.*

Hart et al. (2005) "Genotype—Phenotype Correlation of Mouse Pde6b Mutations" Investigative Ophthalmology and Visual Science. 2005;46:3443-3450.*

Liu et al. (2005) "Ribozyme Knockdown of the [gamma]-Subunit of Rod cGMP Phosphodiesterase Alters the ERG and Retinal Morphology in Wild-Type Mice" Investigative Opthalmology & Visual Science 46:3836-3844.*

Leconte et al. (2000) "Impairment of rod cGMP-gated channel alpha-subunit expression leads to photoreceptor and bipolar cell degeneration" Invest Ophthalmol Vis Sci. Mar. 2000;41(3):917-26.*

Trudeau et al. (2002) Neuron 34:197-2017.*

Lewin et al. (1998) "Ribozyme rescue of photoreceptor cells in a transgenic rat model of autosomal dominant retinitis pigmentosa" Nature Med. Aug;4(8):967-71.*

McCaffrey et al., RNA interference in adult mice, 2002, Nature 418:38-39.
Asahara et al., Induction of Gene into the Rabbit Eye by Iontophoresis: Preliminary Report, 2001, Jpn. J. Ophthalmol. 45:31-39.
Carlson et al., Perineurium in the *Drosophila* embryo and its role in the blood-brain/nerve barrier, 1998, Int. J. Insect Morphology and Embryology 27(2):61-66.
Banks et al., Delivery across the blood-brain barrier of antisense directed against Amyloid beta: reversal of learning and memory deficits in mice overexpressing Amyloid precursor protein, 2001, J. Pharmacology and Experimental Therapeutics 297(3):1113-1121.
Pardridge et al., Vector-mediated delivery of a polymamide ("peptide") mucleic acid analogue through the blood-brain barrier in vivo, 1995, Proc. Nat. Acad. Sci. USA 92:5592-5596.
Boado et al., Drug delivery of antisense molecules to the brain for treatment of Alzheimer's disease and cerebral AIDS, 1998, J. Pharm. Sci. 87(11):1308-1315.
Tyler et al., Peptide nucleic acids targeted to the neurotensin receptor and administered i.p. cross the blood-brain barrier and specifically reduce gene expression, 1999, Proc. Natl. Acad. Sci. USA 96:7053-7058.
Lee et al., Imaging gene expression in the brain in vivo in a transgenic mouse model of Huntington's disease with an antisense radiopharmaceutical and drug-targeting technology, 2002, J. Nuclear Medicine 43(7):948-956.
Penichet et al., An antibody-Avidin fusion protein specific for the Transferrin Receptor serves as a delivery vehicle for the effective brain targeting: initial applications in anti-HIV antisense drug delivery to the brain, 1999, J. Immun. 163:4421-4426.
Wu et al., Pharmacokinetics and blood-brain barrier transport of [3H]-biotinylated phosphorothioate oligodeaoxynucleotide conjugated to a vector-mediated drug delivery system, 1996, J. Pharm. Exp. Ther. and Am. Soc. Pharm. 276(1):206-211.
Shi et al., Antisense imaging of gene expression in the brain in vivo, 2000, Proc. Natl. Acad. Sci. USA 97(26):14709-14714.
Boado, Antisense drug delivery through the blood-brain barrier, 1995, Adv. Drug Delivery Reviews 15(1/3):73-107.
Pineda et al., The genetic network of prototypic planarian eye regeneration is Pax6 independent, 2002, Development 129:1423-1434.
Dryja et al., Mutations in the gene encoding the alpha subunit of the rod cGMP-gated channel in autosomal recessive retinitis pigmentosa, 1995, Proc. Natl. Acad. Sci. USA 92:10177-10181.
Hunt et al., Vitreous treatment of retinal pigment epithelial cells results in decreased expression of FGF-2, 1998, Investigative Ophthalmology & Visual Sci. 39(11):2111-2120.
Kociok et al., Vitreous treatment of cultured human RPE cells results in differential expression of 10 new genes, 2002, Investigative Ophthalmology & Visual Sci. 43(7):2474-2480.
Campochiaro, Gene therapy for retinal and choroidal diseases, 2002, Expert Opinion on Biological Therapy, 2(5):537-544.
Kociok et al., Upregulation of RAS-GTPase Activating Protein (GAP)-Binding Protein (G38BP) in proliferating RPE cells, 1999, J. Cellular Biochemistry 74:194-201.
Chan et al., Expression of chemokine receptors, CXCR4 and CXCR5, and chemokines, BLC and SDF-1, in the eyes of patients with primary intraocular lymphoma, 2003, Ophthalmology 110(2):421-426.
Avgeropoulos et al., New treatment strategies for malignant gliomas, 1999, The Oncologist 4:209-224.
Groothuis, The blood-brain and blood-tumor barriers: a review of strategies for increasing drug delivery, 2000, Neuro-Oncology 2:45-59.
Pardridge, Brain drug targeting and gene technologies, 2001, Japanese J. Pharmacology 87:97-103.
Pardriege, Drug and gene targeting to the brain with molecular Trojan horses, 2002, Nature Reviews 1:131-139.
Qian et al., Targeted drug delivery via the Transferrin Receptor mediated endocytosis pathway, 2002, Pharmacological Reviews 54(4):561-587.
Pardridge, Vector-Mediated drug delivery to the brain, 1999, Advanced Drug Delivery Reviews, 36(2-3):299-321.
Pardridge, CNS drug design based onprinciples of blood-brain barrier transport, 1998, J. Neurochemistry 70:1781-1792.
Pardridge, Drug delivery to the brain, 1997, J. Cerebral Blood Flow and Metabolism, 17(7):713-731.
Philip et al., Polarized expression of monocarboxylate transporters in human retinal pigment epithelium and ARPE-19 cells, 2003, Investigative Ophthalmology & Visual Sci. 44(4):1716-1721.
Nahoko Ogata et al. "Transfection of Basic Fibroblast Growth Factor (bFGF) Gene or bFGF Antisense Gene into Human Retinal Pigment Epithelial Cells" 1999, Graefe's Archive for Clinical and Experimental Ophthalmology, 237:678-684.
Capeans et al. "A c-*myc* Antisense Oligonucleotide Inhibits Human Retinal Pigment Epithelial Cell Proliferation" 1998, Experimental Eye Research, 66:581-589.
Bonilha et al. "Ezrin Promotes Morphogenesis of Apical Microvilli and Basal Infoldings in Retinal Pigment Epithelium" 1999, The Journal of Cell Biology, 147(7):1533-1547.
Detrick et al. "Inhibition of Human Cytomegalovirus Replication in a Human Retinal Epithelial Cell Model by Antisense Oligonucleotides" 2001, Investigative Ophthalmology & Visual Science, 42(1):163-169.
Chooi-May Lai et al. "The Use of Adenovirus-Mediated Gene Transfer to Develop a Rat Model for Photoreceptor Degeneration" 2000, Investigative Ophthalmology and Visual Science, 41(2):580-584.
Crooke "Progress in Antisense Technology: The End of the Beginning" 1999, Methods of Enzymology, Academic Press, 313:3-45.
Caplen "Gene Therapy Progress and Prospect. Downregulating Gene Expression: The Impact of RNA Interference" Gene Therapy, 2004, 11(16):1241-1248.
Chirila et al. "The Use of Synthetic Polymers for Delivery of Therapeutic Antisense Oligodeoxynucleotides" Biomaterials, 2002, 23:321-342.
Opalinska et al. "Nucleic-Acid Therapeutics: Basic Principles and Recent Applications" Nature Reviews, 2002, 1:503-514.
Lu et al. "Delivering siRNA in vivo for Functional Genomics and Novel Therapeutics" 2005, RNA Interference Technology: From Basic Science to Drug Development, Cambridge University Press, 303-317.
Sioud "siRNA Delivery In Vivo" 2005, Methods in Molecular Biology vol. 309: RNA Silencing: Methods and Protocols, Humana Press Inc.
Simeoni et al. "Peptide-Based Strategy for siRNA Delivery into Mammalian Cells" 2005, Methods in Molecular Biology, vol. 309: RNA Silencing: Methods and Protocols, Humana Press Inc.
Deonarain "Ligand-targeted Receptor-mediated Vectors for Gene Delivery" Expert Opinion on Therapeutic Patents, 1998, 8(1):53-69.
Verma et al. "Gene Therapy—Promises, Problems and Prospects" Nature, 1997, 389:239-242.
Verma et al. "Gene Therapy—Twenty-first Century Medicine" Annual Review of Biochemistry. 2005, 74:711-738.
Goncalves "A Concise Peer into the Background, Initial Thoughts and Practices of Human Gene Therapy" BioEssays, 2005, 27:506-517.
Gardlik et al. "Vectors and Delivery Systems in Gene Therapy" Med. Sci, Monit. 2005, 11(4):RA110-121.
Shoji et al. "Current Status of Delivery Systems to Improve Target Efficacy of Oligonucleotides" Current Pharmaceutical Design, 2004, 10:785-796.
Mothe et al. "Analysis of Green Fluorescent Protein Expression in Transgenic Rats for Tracking Transplanted Neural Stem/Progenitor Cells" Journal of Histochemistry & Cytochemistry, 2005, 53(10):1215-1226.
Rummelt et al. "Triple Retinal Infection with Human Immunodeficiency Virus Type 1, Cytomegalovirus, and Herpes Simplex Virus Type 1. Light and Electron Microscopy, Immunohistochemistry, and in situ Hybridization" Ophthamology, 1994, 101(2):270-279, Abstract only.
Caplen "An New Approach to the Inhibition of Gene Expression" Trends in Biotechnology, 2002, 20(2):49-51.
Gan et al. "Specific Interference of Gene Function by Double-stranded RNA in Neuronal Cell Lines" Society for Neuroscience Abstracts, 2001, 27(2):2051.

Dzitoyeva et al. "Intra-abdominal Injection of Double-stranded RNA into Anesthetized Adult *Drosophila* Triggers RNA Interference in the Central Nervous System" Molecular Psychiatry, 2001, 6:655-670.
Acheampong, et al., Distribution of Brimonidine into Anterior and Posterior Tissues of Monkey, Rabbit, and Rat Eyes, *Drug Metab Dispos*. (Apr. 2002), 30(4):421-429.
Adamis, et al., Inhibition of Vascular Endothelial Growth Factor Prevents Retinal Ischemia-Associated Iris Neovascularization in a Nonhuman Primate, *Arch Ophthalmol*. (Jan. 1996), 114(1):66-71.
Addis-Lieser, et al., Opposing Regulatory Roles of Complement Factor 5 in the Development of Bleomycin-Induced Pulmonary Fibrosis, *J Immunol*. (Aug. 1, 2005), 175(3):1894-1902.
Agami, RNAi and Related Mechanisms and Their Potential Use for Therapy, *Curr Opin Chem Biol*. (Dec. 2002), 6(6):829-834.
Agrawal, et al., Antisense Therapeutics: Is It As Simple As Complementary Base Recognition?, *Mol Med Today* (Feb. 2000), 6(2):72-81.
Alexion Pharmaceuticals, Alexion Pharmaceuticals Initiates Treatment in Pivotal Phase III Eculizummab Program in Paraxysmal Nocturnal Emoglobinuria Patients, *News and Information at* www.alexionpharm.com (Sep. 23, 2004).
Altschul, et al., Basic Local Alignment Search Tool, *J Mol Biol*. (Oct. 5, 1990), 215(3):403-410.
Altschul, et al., Gapped BLAST and PSI-BLAST: a New Generation of Protein Database Search Programs, *Nucleic Acids Res*. (Sep. 1, 1997), 25(17):3389-3402.
Ambati, et al., Transscleral Drug Delivery to the Retina and Choroid, *Prog Retin Eye Res*. (Mar. 2002), 21(2):145-151.
Ames, et al., Identification of a Selective Nonpeptide Antagonist of the Anaphylatoxin C3a Receptor That Demonstrates Antiinflammatory Activity in Animal Models, *J Immunol*. (May 15, 2001), 166(10):6341-6348.
Anderson, et al., A Role for Local Inflammation in the Formation of Drusen in the Aging Eye, *Am J Ophthalmol*. (Sep. 2002), 134(3):411-431.
Anderson, et al., Vitronectin Gene Expression in the Adult Human Retina, *Invest Ophthalmol Vis Sci*. (Dec. 1999), 40(13):3305-3315.
Anderson, Human Gene Therapy, *Nature* (Apr. 30, 1998), 392:S25-S31.
Andra, et al., Generation and Characterization of Transgenic Mice Expressing Cobra Venom Factor, *Mol Immunol*. (Oct. 2002), 39(5-6):357-365.
Banan, et al., The Ins and Outs of RNAi in Mammalian Cells, *Curr Pharm Biotechnol*. (Oct. 2004), 5(5):441-450.
Bao, et al., C5a Promotes Development of Experimental Lupus Nephritis which Can be Blocked with a Specific Receptor Antagonist, *Eur J Immunol*. (Aug. 2005), 35(8):2496-2506.
Bartz, et al., Production of High-Titer Human Immunodeficiency Virus Type 1 Pseudotyped with Vesiculuar Stomatitis Virus Glycoprotein, *Methods* (Aug. 1997), 12(4):337-342.
Bass, The Short Answer, *Nature* (May 24, 2001), 411(6836):428-429.
Bates, et al., VEGF$_{165}$b, an Inhibitory Splice Variant of Vascular Endothelial Growth Factor, Is Down-Regulated in Renal Cell Carcinoma, *Cancer Res*. (Jul. 15, 2002), 62(14):4123-4131.
Belletti, et al., Modulation of in vivo growth of thyroid tumor-derived cell lines by sense and antisense vascular endothelial growth factor gene, *Oncogene* (Aug. 26, 1999), 18(34):4860-4869.
Bennett, et al., Humoral response after administration of E1-deleted adenoviruses: immune privilege of the subretinal space, *Hum Gene Ther*. (Sep. 10, 1996), 7(14):1763-1769 (Abstract).
Berkhout, An Eye-Opener for RNAi Therapeutics, *J Formos Med. Assoc*. (Oct. 2008), 107(10):749-750.
Blinder, et al., Effect of Lesion Size, Visual Acuity, and Lesion Composition on Visual Acuity Change with and without Verteporfin Therapy for Choroidal Neovascularization Secondary to Age-Related Macular Degeneration: TAP and VIP Report No. 1, *Am J Ophthalmol*. (Sep. 2003), 136(3):407-418.
Blom, et al., Complement Inhibitor C4b-binding Protein—Friend or Foe in the Innate Immune System?, *Mol Immunol*. (Apr. 2004), 40(18):1333-1346.
Bok, Evidence for an Inflammatory Process in Age-Related Macular Degeneration Gains New Support, *Proc Natl Acad Sci USA* (May 17, 2005), 102(20):7053-7054.
Boocock, et al., Expression of Vascular Endothelial Growth Factor and its Receptors fit and KDR in Ovarian Carcinoma, *J Natl Cancer Inst*. (Apr. 5, 1995), 8(7):506-516.
Bora, et al., Role of Complement and Complement Membrane Attack Complex in Laser-induced Choroidal Neovascularization, *J Immunol*. (Jan. 1, 2005), 174(1):491-497.
Brantl, Antisense-RNA regulation and RNA Interference, *Biochim Biophys Acta*. (May 3, 2002), 1575(1-3):15-25.
Bressler, et al., Verteporfin Therapy of Subfoveal Choroidal Neovasculariation in Patients with Age-Related Macular Degeneration, *Arch Ophthalmol*. (Nov. 2002), 120(11):1443-1454.
Brummelkamp, et al., A System for Stable Expression of Short Interfering RNAs in Mammalian Cells, *Science* (Apr. 19, 2002), 296(5567):550-553.
Bullard, et al., Direct Comparison of Nick-Joining Activity of the Nucleic Acid Ligases from Bacteriophage T4, *Biochem J*. (Aug. 15, 2006), 398(1):135-144.
Bustin, Absolute Quantification of mRNA Using Real-time Reverse Transcription Polymerase Chain Reaction Assays, *J Mol Endocrinol*. (Oct. 2000), 25(2):169-193.
Cai, et al., A Direct Role for C1 Inhibitor in Regulation of Leukocyte Adhesion, *J Immunol*. (May 15, 2005), 174(10):6462-6466.
Caplen, RNAi as a Gene Therapy Approach, *Expert Opin Biol Ther*. (Jul. 2003), 3(4):575-586.
Chen, et al., Prevention of Hyperacute Rejection of Pig-to-Monkey Cardiac Xenografts by Chinese Cobra Venom Factor, *Transplant Proc*. (Nov.-Dec. 2001), 33(7-8):3857-3858.
Cho, Small Interfering RNA-induced TLR3 Activation Inhibits Blood and Lymphatic Vessel Growth, *Proc Natl Acad Sci USA* (Apr. 28, 2009), 106(17):7137-7142.
Coburn, et al., siRNAs: a New Wave of RNA-Based Therapeutics, *J Antimicrob Chemother*. (Apr. 2003), 51(4):753-756.
Conley, et al., Candidate Gene Analysis Suggests a Role for Fatty Acid Biosynthesis and Regulation of the Complement System in the Etiology of Age-Related Maculopathy, *Hum Mol Genet*. (Jul. 15, 2005), 14(14):1991-2002.
Daiger, Was the Human Genome Project Worth the Effort?, *Science* (Apr. 15, 2005), 308(5720):362-364.
Davis, et al., The Age-Related Eye Disease Study Severity Scale for Age-Related Macular Degeneration: AREDS Report No. 17, *Arch Ophthalmol*. (Nov. 2005), 123(11):1484-1498.
Devroe, et al., Retrovirus-delivered siRNA, *BMC Biotech*. (Aug. 28. 2002), 2:1-5.
Dornburg, Reticuloendotheliosis Viruses and Derived Vectors, *Gene Ther*. (Jul. 1995), 2(5):301-310.
Dorsett, et al., siRNAs: Applications in Functional Genomics and Potential as Therapeutics, *Nat Rev Drug Discov*. (Apr. 2004), 3(4):318-329.
Downward, Science, medicine and the future, RNA Interference, *BMJ* (May 22, 2004), 328(7450):1245-1248.
Dragun, et al., ICAM-1 Antisense Oligodesoxynucleotides Prevent Reperfusion Injury and Enhance Immediate Graft Function in Renal Transplantation, *Kidney Int*. (Aug. 1998), 54(2):590-602.
Dyer, et al., The Role of Complement in Immunological Demyelination of the Mammalian Spinal Cord, *Spinal Cord* (Jul. 2005), 43(7):417-425.
EBI Accession No. GSN-ADY90830—Retrieved from online database Jun. 16, 2005, VEGF siRNA SEQ ID No. 3868, XP002468091.
EBI Accession No. GSN-ADY90830—Retrieved from online database Jun. 16, 2005, VEGF siRNA SEQ ID No. 3867, XP002468090.
Edwards, et al., Complement Factor H Polymorphism and Age-Related Macular Degeneration, *Science* (Apr. 15, 2005), 308(5720):421-424.
Eglitis, et al., Retroviral Vectors for Introduction of Genes into Mammalian Cells, Biotechniques (Jul.-Aug. 1988), 6(7):608-614.
Elbashir, et al., Analysis of Gene Function in Somatic Mammalian Cells Using Small Interfering RNAs, *Methods* (Feb. 2002), 26(2):199-213.
Elbashir, et al., Functional Anatomy of siRNAs for Mediating Efficient RNAi in *Drosophila melanogaster* Embryo Lysate, *EMBO J*. (Dec. 3, 2001), 20(23):6877-6888.
Elbashir, et al., RNA Interference is mediated by 21- and 22-nucleotide RNAs. *Genes Dev*. (Jan. 15, 2001), 15(2):188-200.

Engström, et al., Complement C3 is a Risk Factor for the Development of Diabetes: a Population-Based Cohort Study, *Diabetes* (Feb. 2005), 54(2):570-575.
Erickson, RNAi Revs Up, *Start-Up Emerging Medical Ventures* (Art. #2002900168) (Oct. 1, 2002). pp. 1-12.
Far, et al., The Activity of siRNA in Mammalian Cells is Related to Structural Target Accessiblity: a Comparison with Antisense Oligonucleotides, *Nucleic Acids Re.* (Aug. 1, 2003), 31(15):4417-4424.
Finehout, et al., Complement Protein Isoforms in CSF as Possible Biomarkers for Neurodegenerative Disease, *Dis Markers* (2005), 21(2):93-101. (Abstract).
Fire, et al., Potent and specific genetic interference by double-stranded RNA in *Caenorhabditis elegans, Nature* (Feb. 19, 1998), 391(6669):806-811.
Fisher, et al., Transduction with Recombinant Adeno-Associated Virus for Gene Therapy is Limited by Leading-Strand Synthesis, *J Virol*. (Jan. 1996), 70(1):520-532.
Fjose, et al., RNAi and MicroRNAs: from Animal Models to Disease Therapy, *Birth Defects Res C Embryo Today* (Jun. 2006), 78(2):150-171.
Fujita, et al., Complement Activation Accelerates Glomerular Injury in Diabetic Rats, *Nephron* (Feb. 1999), 81(2):208-214.
Fung, et al., Inhibition of Complement, Neutrophil, and Platelet Activation by an Anti-Factor D Monoclonal Antibody in Simulated Cardiopulmonary Bypass Circuits, *J Thorac Cardiovasc Surg*. (Jul. 2001). 122(1):113-122.
Gabizon, et al., Liposome Formulations With Prolonged Circulation Time in Blood and Enhanced Uptake by Tumors, *Proc Natl Acad Sci* USA (Sep. 1988), 85(18):6949-6953.
Gan, et al., Specific Interference of Gene Function by Double-Stranded RNA in Neuronal Cell Lines, Program No. 772.10, 2001 Neuroscience Meeting Planner. San Diego, CA (Nov. 14, 2001) (Abstract).
Ganesh, et al., Structure of Vaccinia Complement Protein in Complex with Heparin and Potential Implications for Complement Regulation, *Proc Natl Acad Sci* USA (Jun. 15 2004), 101(24):8924-8929.
Garrett, et al., In vivo use of oligonucleotides to inhibit choroidal neovascularisation in the eye. *J Gene Med* (Jul.-Aug. 2001), 3(4):373-383.
Genbank Accession No. AF 091352 (1998).
Genbank Accession No. AF 214570 (1999) (see :SATO—VEGF).
Genbank Accession No. AF 430806 (2001).
Genbank Accession No. AJ 010438 (1988).
Genbank Accession No. AJ 245445, 1999 (Einspanier—Flt1).
Genbank Accession No. CS 245578.
Genbank Accession No. CS 245579.
Gompels, et al., C1 inhibitor deficiency: consensus document, *Clin Exp. Immunol*. (Mar. 2005), 139(3):379-394.
Guo, et al., Role of C5A in Inflammatory Responses, *Annu Rev Immunol*. (2005), 23:821-852.
Hageman, et al., A common haplotype in the complement regulatory gene factor H (*HF1/CFH*) predisposes individuals to age-related macular degeneration, *Proc Natl Acad Sci USA* (May 17, 2005), 102(20):7227-7232.
Hageman, et al., An Integrated Hypothesis that Considers Drusen as Biomarkers of Immune-Mediated Processes at the RPE-Bruch's Membrane Interface in Aging and Age-Related Macular Degeneration, *Prog Retin Eye Res*. (Nov. 2001), 20(6):705-732.
Hageman, et al., Molecular composition of drusen as related to substructural phenotype, *Mol. Vis*. (Nov. 3, 1999), 5:28-37.
Haines, et al., Complement Factor H Variant Increases the Risk of Age-Related Macular Degeneration, *Science* (Apr. 15, 2005), 308(5720):419-421.
Halstead, et al., Complement Inhibition Abrogates Terminal Injury in Miller Fisher Syndrome, *Ann Neurol*. (Aug. 2005), 58(2):203-210.
Hammond, et al., Post-Transcriptional Gene Silencing by Double-Stranded RNA, *Nat Rev Genet* (Feb. 2001), 2(2):110-119.
Harborth, et al., Self Assembly of NuMA multiarm oligomers as structural units of a nuclear lattice, *EMBO J*. (Mar. 15, 1999), 18(6):1689-1700.
Harborth, et al., Sequence. Chemical, and Structural Variation of Small Interfering RNAs and Short Hairpin RNAs and the Effect on Mammalian Gene Silencing, *Antisense Nucleic Acid Drug Dev*. (Apr. 2003), 13(2):83-105.
Hart, et al., Genotype-Phenotype Correlation of Mouse *Pde6b* Mutations, *Invest Ophthalmos Vis Sci*., (Sep. 2005), 46(9):3443-3450.
Hart, et al., Initiation of complement activation following oxidative stress. In vitro and in vivo observations, *Mol Immunol*. (Jun. 2004), 41(2-3):165-171.
Hasan, et al., VEGF antagonists, *Expert Opin Biol Ther*. (Jul. 2001), 1(4):703-718.
He, et al., Complement Inhibitors Targeted to the Proximal Tubule Prevent Injury in Experimental Nephrotic Syndrome and Demonstrate a Key Role for C5b-9, *J Immunol*. (May 1, 2005), 174(9):5750-5757.
Hillebrandt, et al., Complement factor 5 is a quantitative trait gene that modifies liver fibrogenesis in mice and humans, *Nat. Genet* (Aug. 2005), 37(8):835-843.
Hodgetts, et al., Complement and myoblast transfer therapy: Donor myoblast survival is enhanced following depletion of host complement C3 using cobra venom factor, but not in the absence of C5, *Immunol Cell Biol*. (Jun. 2001), 79(3):231-239.
Hoeg, et al., In Vitro and In Vivo Efficacy of a HIF-1 Alpha-Antisense Oligonucleotide Containing Locked Nucleic Acids, *ECJ Supplements* (Sep. 24, 2003), pp. S212-S213 (Abstract).
Holash, et al., VEGF-Trap: A VEGF blocker with potent antitumor effects, *Proc Natl Acad Sci USA* (Aug. 20, 2002), 99(17):11393-11398.
Holers, et al., The alternative pathway of complement in disease: opportunities for therapeutic targeting, *Mol Immunol*. (Jun. 2004), 41(2-3):147-152.
Houck, et al., The Vascular Endothelial Growth Factor Family: Identification of a Fourth Molecular Species and Characterization of Alternative Splicing of RNA, *Mol Edocrinol*. (Dec. 1991), 5(12):1806-1814.
Jakobsdottir, et al., Susceptibility Genes for Age-Related Maculopathy on Chromosome 10q26, *Am J Hum Genet*. (Sep. 2005), 77(3):389-407.
Jen, et al., Suppression of Gene Expression by Targeted Disruption of Messenger RNA: Available Options and Current Strategies, *Stem Cells*. (2000), 18(5):307-319.
Jha, et al., Vaccinia complement control protein: Multi-functional protein and a potential wonder drug, *J Biosci*. (Apr. 2003), 28(3):265-271.
Johnson, et al., A Potential Role for Immune Complex Pathogenesis in Drusen Formation, *Exp Eye Res*. (Apr. 2000), 70(4):441-449.
Johnson, et al., Complement Activation and Inflammatory Processes in Drusen Formation and Age Related Macular Degeneration, *Exp Eye Res*. (Dec. 2001), 73(6):887-896.
Johnson, et al., The Alzheimer's Aβ-peptide is deposited at sites of complement activation in pathologic deposits associated with aging and age-related macular degeneration, *Proc Natl Acad Sci USA* (Sep. 3, 2002), 99(18):11830-11835.
Kang, et al., An Antisense Oligonucleotide that Inhibits the Expression of Hypoxia-Inducible Factor-1 Alpha Alters Hypoxia-Induced Changes in Proliferation and Viability of Human Cardiac Fibroblasts Abstracts from Scientific Sessions 2001 II-57:274 (Abstract).
Katz, et al., ICAM-1 Antisense Oligodeoxynucleotide Improves Islet Allograft Survival and Function, *Cell Transplant*. (Nov.-Dec. 2000), 9(6):817-828.
Kim, et al., Potent VEGF blockade causes regression of coopted vessels in a model of neuroblastoma, *Proc Natl Acad Sci USA*. (Aug. 20, 2002), 99(17):11399-11404.
Klein, et al., Complement Factor H Polymorphism in Age-Related Macular Degeneration, *Science*. (Apr. 15, 2005), 308(5720):385-389.
Kleinman, et al., Sequence- and target-independent angiogenesis suppression by siRNA via TLR3, *Nature* (Apr. 3, 2008), 452(7187):591-598.
Kock, et al., Structure and Function of Recombinant Cobra Venom Factor, *J Biol Chem*. (Jul. 16, 2004), 279(29):30836-30843.

Konopatskaya, et al., $VEGF_{165}b$, an endogenous C-terminal splice variant of VEGF, inhibits retinal neovascularization in mice, *Mol Vis.* (May 26, 2006), 12:626-632.
Kostelny, et al., Formation of a Bispecific Antibody by the Use of Leucine Zippers, *J Immunol.* (Mar. 1, 1992), 148(5):1547-1553.
Krishnamachary, et al., Regulation of Colon Carcinoma Cell Invasion by Hypoxia-Inducible Factor 1, *Cancer Res.* (Mar. 1, 2003), 63(5):1138-1143.
Kuehn, Gene Discovery Provides Clues to Cause of Age-Related Macular Degeneration, *JAMA.* (Apr. 20, 2005), 293(15):1841-1845.
Kurschat, et al., Optimizing splinted ligation of highly structured small RNAs, RNA. (Dec. 2005), 11(12):1909-1914.
Lawson, et al., Understanding the Glaucoma Gene, *Developmental Control of Gene Expression* (2000), 69-74:14a (Abstract).
Leconte, et al., Impairment of Rod cGMP-Gated Channel α-Subunit Expression Leads to Photoreceptor and Bipolar Cell Degeneration, *Invest. Ophthamol. Vis Sci.* (Mar. 2000). 41(3):917-926.
Lee, et al., Expression of small interfering RNAs targeted against HIV-1 *rev* transcripts in human cells, *Nat Biotechnol.* (May 2002), 20(5):500-505.
Levy, et al., Post-Transcriptional Regulation of Vascular Endothelial Growth Factor by Hypoxia, *J Biol. Chem.* (Feb. 2, 1996), 271(5):2746-2753.
Lewis, et al., A serum-resistant cytofectin for cellular delivery of antisense oligodeoxynucleotides and plasmid DNA, *Proc Natl Acad Sci USA.* (Apr. 16, 1996), 93(8):3176-3181.
Linton, et al., Therapeutic efficacy of a novel membrane-targeted complement regulator in antigen-induced arthritis in the rat, *Arthritis Rheum.*(Nov. 2000), 43(11):2590-2597 (Abstract).
Liu, et al., Ribozyme Knockdown of the γ-Subunit of Rod cGMP Phosphodiesterase Alters the ERG and Retinal Morphology in Wild-Type Mice, *Invest Ophthalmol Vis Sci.* (Oct. 2005), 46(10):3836-3844.
Lucas, et al., Secreted Immunomodulatory Viral Proteins as Novel Biotherapeutics, *J Immunol.* (Oct. 15, 2004), 173(8):4765-4774.
Manoharan, RNA interference and chemically modified small interfering RNAs, *Curr Opin Chem Biol.* (Dec. 2004), 8(6):570-579.
Marchand, et al., Blockade of in vivo VEGF-mediated angiogenesis by antisense gene therapy: role of Flk-1 and Flt-1 receptors, *Am J Physiol Heart Circ Physiol.* (Jan. 2002), 282(1):H194-H204.
Mastellos., et al., From atoms to aystems: a cross-disciplinary approach to complement-mediated functions, *Mol Immunol.* (Jun. 2004), 41(2-3):153-l64.
Mastellos, et al., Novel biological networks modulated by complement, *Clinical Immunol.* (Jun. 2005), 115(3):225-235.
Merriam-Webster's Online Dictionary, Definition of Ligand, http://www.merriam-webster.com/dictionary/ligand (Jun. 2, 2008).
Miller, Retrovirus Packaging Cells, *Hum Gene Ther.* (Spring 1990), 1(1):5-14 (Abstract).
Miyagishl et al., U6 promoter-driven siRNAs with four uridine 3' overhangs efficiently suppress targeted gene expression in mammalian cells, *Nat Biotechnol.* (May 2002), 20(5):497-500.
Miyamoto, et al., Prevention of leukostasis and vascular leakage in streptozotocin-induced diabetic retinopathy via intercellular adhesion molecule-1 inhibition, *Proc Natl Acad Sci USA.* (Sep. 14, 1999), 96(19):10836-10841.
Miyamoto, et al., Vascular Endothelial Growth Factor (VEGF)-Induced Retinal Vascular Permeability is Mediated by Intercellular Adhesion Molecule-1 (ICAM-1), *Am J Pathol.* (May 2000), 156(5):1733-1739.
Mollnes, et al., Complement in inflammatory tissue damage and disease, *Trends Immunol.* (Feb. 2002), 23(2):61-64.
Moromizato, et al., CD18 and ICAM-1 Dependent Corneal Neovascularization and Inflammation after Limbal Injury, *Am J Pathol.* (Oct. 2000), 157(4):1277-1281.
Mullins, et al., Drusen associated with aging and age-related macular degeneration contain proteins common to extracellular deposits associated with atherosclerosis, elastosis, amyloidosis, and dense deposit disease, *FASEB J.* (May 1, 2000), 14(7):835-846.
Nandakumar, et al., RNA Substrate Specificity and Structure-guided Mutational Analysis of Bacteriophage T4 RNA *Ligase 2, J Biol Chem.* (Jul. 23, 2004), 279(30):31337-31347.
Nielsen, Systemic Delivery: The Last Hurdle?, *Gene Ther.* (Jun. 2005), 12(12):956-957.
Nishiwaki, et al., Introduction of short interfering RNA to silence endogenous E-selection in vascular endothelium leads to successful inhibition of leukocyte adhesion, *Biochem Biophys Res Commun.* (Oct. 31, 2003), 310(4):1062-1066.
Novina, et al., siRNA-directed inhibition of HIV-1 infection, *Nat Med.* (Jul. 2002). 8(7):681-686.
Nückel, et al., Alemtuzumab induces enhanced apoptosis in vitro in B-cells from patients with chromic lymphocytic leukemia by antibody-dependent cellular cytotoxicity, *Eur J Pharmacol.* (May 9, 2005), 514(2-3):217-224.
Ohali, et al., Complement profile in childhood immune thrombocytopenic purpura: a prospective pilot study, *Ann Hematol.* (Nov. 2005), 84(12):812-815.
Ostergaard, et al., Complement activation and diabetic vascular complications, *Clin Chim Acta.* (Nov. 2005), 361(1-2):10-19.
Paddison, et al., Short hairpin RNAs (shRNAs), induce sequence-specific silencing in mammalian cells, *Genes Dev.* (Apr. 15. 2002), 16(8):948-958.
Paroo, et al., Challenges for RNAi in vivo, *Trends Biotechnol.* (Aug. 2004), 22(8):390-394.
Patterson, et al., Cloning and functional analysis of the promoter for KDR/flk-1, a receptor for vascular endothelial growth factor, *J Biol Chem.* (Sep. 29, 1995), 270(39):23111-23118 (Abstract).
Paul, et al., Effective expression of small interfering RNA in human cells, *Nat Biotechnol.* (May 2002) 20(5):505-508.
Peng, et al., Role of C5 in the development of airway inflammation, airway hyperresponsiveness, and ongoing airway response, *J Clin Invest.* (Jun. 2005), 115(6):1590-1600.
Pratt, et al., Nontransgenic Hyperexpression of a Complement Regulator in Donor Kidney Modulates Transplant Ischemia/Reperfusion Damage, Acute Rejection, and Chronic Nephropathy, *Am J Pathol.* (Oct. 2003), 163(4):1457-1465.
Reich, et al., Small Interfering RNA ( siRNA), targeting VEGF Effectively Inhibits Ocular Neovascularization in a Mouse Model, *Mol. Vis.* (May 30, 2003), 9(31):210-216.
Remington's *Pharmaceutical Sciences*, $17^{th}$ ed., Mack Publishing Co., Easton. PA. (1985), TOC (See Gennaro).
Rennel, et al., Recombinant human $VEGF_{165}b$ Protein is an effective anti-cancer agent in mice. *Eur J Cancer* (Sep. 2008), 44(13):1883-1894.
Rennel, et al., The endogenous anti-angiogenic VEGF isoform, $VEGF_{165}b$ inhibits human tumour growth in mice, *Br J Cancer* (Apr. 8, 2008), 98(7):1250-1257.
Roberts, et al., Efficient expression of ribozyme and reduction of stromelysin mRNA in cultured cells and tissue from rabbit knee via Adeno-associated Virus (AAV), *Gene Therapy and Mol. Biol.* (Dec. 1999), 4:45-58.
Rosenfeld, et al., Maximum Tolerated Dose of a Humanized Anti-Vascular Endothelial Growth Factor Antibody Fragment for Treating Neovascular Age-Related Macular Degeneration, *Opthalmology.* (Jun. 2005), 112(6):1048-1053.
Rother, et al., Inhibition of terminal complement: a novel therapeutic approach for the treatment of systemic lupus erythematosus, *Lupus* (2004), 13(5):328-334.
Rubinson, et al., A lentivirus-based system to functionally silence genes in primary mammalian cells, stem cells and transgenic mice by RNA interference, *Nat Genet.* (Mar. 2003), 33(3):401-406 (Abstract).
Russell, et al., Location. Substructure, and Composition of Basal Laminar Drusen Compared with Drusen Associated with Aging and Age-Related Macular Degeneration, *Am J Ophthalmol.* (Feb. 2000), 129(2):205-214.
Sakurai, et al., Targeted Disruption of the CD18 or ICAM-1 Gene Inhibits Choroidal Neovascularization, *Invest Ophthalmol Vis Sci.* (Jun. 2003), 44(6):2743-2749.
Samarsky, et al., RNAi in drug development: Practical Considerations, RNA Interference Tech., Cambridge (Appasani ed.), (Sep. 1, 2005), pp. 384-395.
Samulski, et al., A Recombinant Plasmid from Which an Infectious Adeno-Associated Virus Genome Can Be Excised in Vitro and its use to Study Viral Replication, *J Virol.* (Oct. 1987), 61(10):3096-3101.

Samulski, et al., Helper-Free Stocks of Recombinant Adeno-Associated Viruses: Normal Integration Does Not Require Viral Gene Expression, *J Virol*. (Sep. 1989), 63(9):3822-3828.
Sato, et al., Human cDNA for Vascular Endothelial Growth Factor Isoform VEGF121, GenBank Accession No. AF214570. (Sep. 1999) (see Genbank).
Scanlon, Anti-Genes: siRNA, Ribozymes and Antisense, *Curr Pharm Biotechnol*. (Oct. 2004), 5(5):415-420.
Schroder, et al., A single-stranded promoter for RNA polymerase III, *Proc Natl Acad Sci* USA. (Feb. 4, 2003), 100(3):934-939.
Sewell, et al., Complement C3 and C5 play critical roles in traumatic brain cryoinjury: blocking effects on neutrophil extravasation by C5a receptor antagonist, *J Neuroimmunol*. (Oct. 2004), 155(1-2):55-63.
Shen, et al., A Study of Cobra Venom Factor in Ex Vivo Pig Liver Perfusion Model, *Transplantation Proc*. (Nov.-Dec. 2001), 33(7-8):3860-3861.
Shen, et al., Suppression of ocular neovascularization with siRNA targeting VEGF receptor 1, *Gene Ther*. (Feb. 2006), 13(3):225-234.
Shi, et al., Inhibition of renal cell carcinoma antiogenesis and growth by antisense oligonucleotides targeting vascular endothelial growth factor, *Br J Cancer* (Jul. 1, 2002), 87(1):119-126.
Shibuya, et al., Nucleotide sequence and expression of a novel human receptor-type tyrosine kinaase gene (flt), closely related to the fins family, *Oncogene*. (Apr. 1990), 5(4):519-524 (Abstract).
Shim, et al., Inhibition of Angiopoietin-1 Expression in Tumor Cells by an Antisense RNA Approach Inhibited Xenograft Tumor Growth in Immunodeficient Mice, *Int J Cancer*. (Oct. 1, 2001), 94(1):6-15.
Shu, et al., Sphingosine Kinase Mediates Vascular Endothelial Growth Factor-Induced Activation of Ras and Mitogen-Activated Protein Kinases, *Mol Cell Biol*. (Nov. 2002), 22(22):7758-7768.
Smith, et al., Membrane-targeted complement inhibitors, *Mol Immunol*. (Aug. 2001), 38(2-3):249-255.
Sohn, et al., Chronic Low Level Complement Activation within the Eye is Controlled by Intraocular Complement Regulatory Proteins, *Invest Ophthahmol Vis Sci*. (Oct. 2000), 41(11):3492-3502.
Sohn, et al., Complement Regulatory Activity of Normal Human Intraocular Fluid is Mediated by MCP, DAF and CD59, *Invest Ophthalmal Vis Sci*. (Dec. 2000), 41(13):4195-4202.
Sohn, et al., Tolerance is dependent on complement C3 fragment iC3b binding to antigen-presenting Cells, *Nat Med*. (Feb. 2003), 9(2):206-212.
Songsivilai, et al., Bispecific antibody: a tool for diagnosis and treatment of disease, *Clin Exp Immunol*. (Mar. 1990), 79(3):315-321.
Spaide, et al., Intravitreal Bevacizumab Treatment of Choroidal Neovascularization Secondary to Age-Related Macular Degeneration, Retina (2006), 26(4):383-390.
Speidl, et al., Complement component C5a predicts future cardiovascular events in patients with advanced atherosclerosis, *Eur Heart J*. (Nov. 2005), 26(21):2294-2299.
Speirs, et al., Production of VEGF and expression of the VEGF receptors Flt-1 and KDR in primary cultures of epithelial and stromal cells derived from breast tumours, *Br J Cancer* (May 1999), 80(5-6):898-903.
Stein, et al., Oligodeoxynucleotides as Inhibitors of Gene Expression: A Review, *Cancer Res*. (May 15, 1988), 48(10):2659-2668.
Strachan, et al., A New Small Molecule C5a Receptor Antagonist Inhibits the Reverse-Passive Arthus Reaction and Endotoxic Shock in Rats, *J Immunol*. (Jun. 15, 2000), 164(12):6560-6565.
Sun, et al., Gene transfer of antisense hypoxia inducible factor-1 $\alpha$ enhances the therapeutic efficacy of cancer immunotherapy, *Gene Ther*. (Apr. 2001), 8(8):638-645.
Sun, et al., Prolonged cardiac xenograft survival in guinea pig-to-rat model by a highly active cobra venom factor, *Toxicon*. (Sep. 1, 2003), 42(3):257-262.
Szoka, Jr., et al., Comparative Properties and Methods of Preparation of Lipid Vesicles (Liposomes), Ann Rev Biophys Bioeng. (Jun. 1980), 9:467-508.
Thurman, et al., A novel inhibitor of the alternative complement pathway prevents antiphospholipid antibody-induced pregnancy loss in mice, *Mol Immunol*. (Jan. 2005), 42(1):87-97.
Tischer, et al., The Human Gene for Vascular Endothelial Growth Factor. Multiple Protein Forms Are Encoded Through Alternative Exon Splicing, J Biol Chem. (Jun. 25, 1991), 266(18):11947-11954 (Abstract).
Tolentino, et al., Intravitreal Injection of Vascular Endothelial Growth Factor Small Interfering RNA Inhibits Growth and Leakage in a Nonhuman Primate, Laser-induced Model of Choroidal Neovascularization, *Retina*. (Feb. 2004), 24(1):132-138.
Tuschl, Expanding small RNA interference, *Nat Biotechnol*. (May 2002), 20(5):446-448.
Tuschl, The siRNA user guide, http://www.mpidpc.gwdg.de/abteilungen/100/105/sirna.html (May 6, 2004).
Tuschl, The siRNA user guide, http://www.mpidpc.gwdg.de/abteilungen/100/105/sirna.html (Oct. 11, 2002).
Van Brunt, Shoot the Messenger, Signals Magazine, http://www.signalsmag.com/signalsmag/3DF5AEF6049CC81C99256C1D0055BAA (Aug. 22, 2002).
Van Der Krol, et al., Modulation of Eukaryotic Gene Expression by Complementary RNA or DNA Sequences, *BioTechniques*. (Nov.-Dec. 1988), 6(10):958-976.
Vickers, et al., Efficient Reduction of Target RNAs by Small Interfering RNA and RNase H-dependent Antisense Agents *J Biol Chem*. (Feb. 28, 2003), 278(9):7108-7118.
Vogel, et al., Recombinant cobra venom factor, *Mol Immunol*. (Jun. 2004). 41(2-3):191-199.
Walport, Complement at the Interface Between Innate and Adaptive Immunity, Complement, First of Two Parts, *N Engl J Med*. (Apr. 12, 2001), 344(14):1058-1066.
Walport, Complement at the Interface Between Innate and Adaptive Immunity, Complement: Second of Two Parts, *N Engl J Med*. (Apr. 12, 2001), 344(15):1140-1144.
Ward, et al., Genomic structure of the human angiopoietins show polymorphism in angiopoietin-2, *Cytogenet Cell Genet*. (2001), 94(3-4):147-154.
Warren, et al., Successful ICAM-1 Gene Inactivation in Pluripotent Stem Cell using RNA Interference and in Situ Expressed Antisense/Ribozyme Transgenes, *J Am Soc Nephrology* (2002), p. 101A (Abstract).
Xia, et al., siRNA-mediated gene silencing in vitro and in vivo, *Nat Biotechnol*. (Oct. 2002), 20(10):1006-1010.
Xu, et al., Protective effect of membrane cofactor protein against complement-dependent injury, *Acta Pharmacol Sin*. (Aug. 2005), 26(8):987-991.
Zareparsi, et al., Strong Association of the Y402H Variant in Complement Factor H at 1q32 with Susceptibility to Age-Related Macular Degeneration, *Am J Hum Genet*. (Jul. 2005), 77(1):149-153.
Zheng, et al., Protection of Renal Ischemia Injury Using Combination Gene Silencing of Complement 3 and Caspase 3 Genes, *Transplantation* (Dec. 27 2006), 82(12):1781-1786.

* cited by examiner

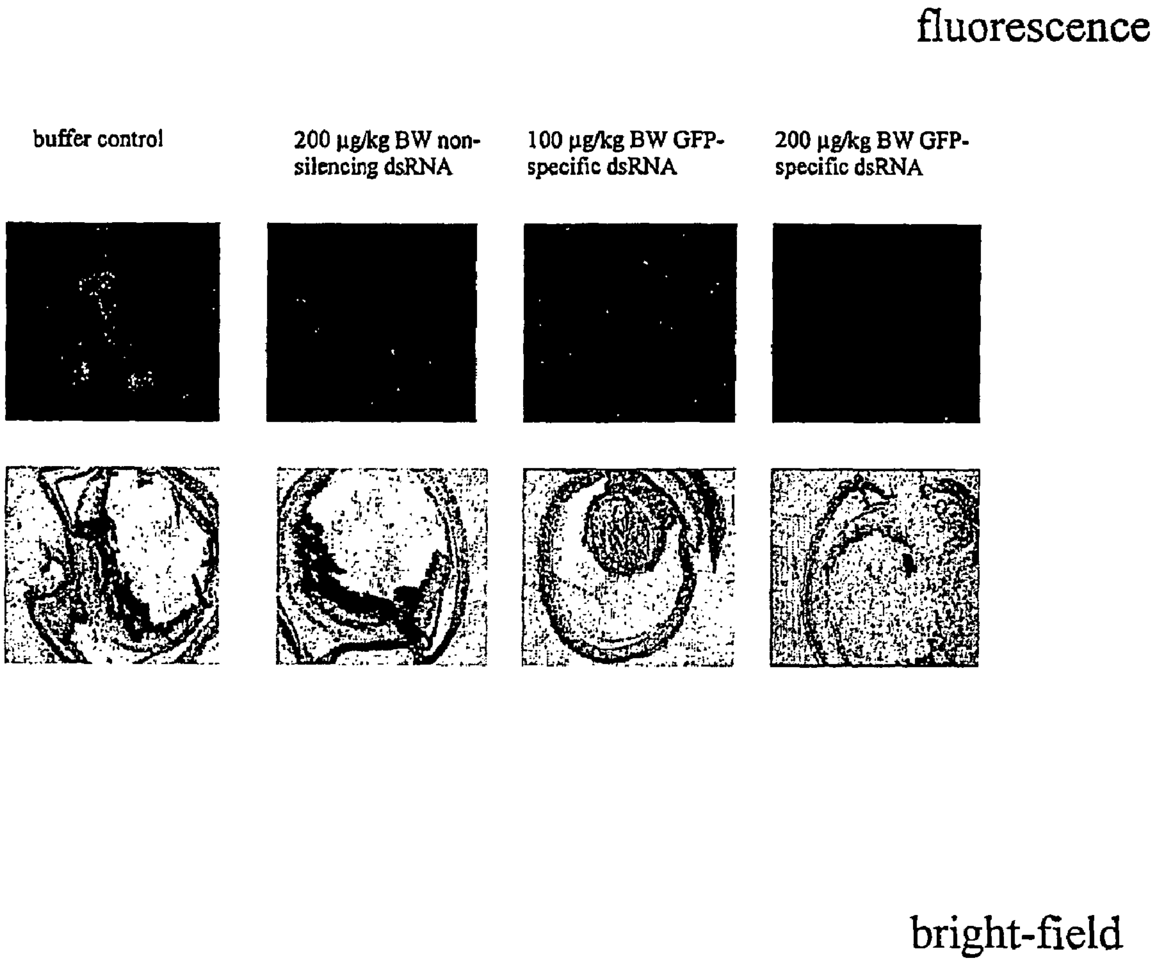
fluorescence
buffer control
200 µg/kg BW non-silencing dsRNA
100 µg/kg BW GFP-specific dsRNA
200 µg/kg BW GFP-specific dsRNA
bright-field

SEQUENCE LISTING

```
<160> NUMBER OF SEQ ID NOS: 10

<210> SEQ ID NO 1
<211> LENGTH: 2500
<212> TYPE: DNA
<213> ORGANISM: homo sapiens
<220> FEATURE:
<221> NAME/KEY: CDS
<222> LOCATION: (25)..(2097)
<223> OTHER INFORMATION: Homo sapiens cyclic nucleotide gated channel
      alpha 1

<400> SEQUENCE: 1

tatattactt aaacaaccaa agat atg aaa cta tcc atg aag aac aat att        51
                           Met Lys Leu Ser Met Lys Asn Asn Ile
                           1               5

atc aat aca cag cag tct ttt gta acc atg ccc aat gtg att gta cca       99
Ile Asn Thr Gln Gln Ser Phe Val Thr Met Pro Asn Val Ile Val Pro
10                  15                  20                  25

gat att gaa aag gaa ata cga agg atg gaa aat gga gca tgc agc tcc      147
Asp Ile Glu Lys Glu Ile Arg Arg Met Glu Asn Gly Ala Cys Ser Ser
                30                  35                  40

ttt tct gag gat gat gac agt gcc tat aca tct gaa gaa tca gag aat      195
Phe Ser Glu Asp Asp Asp Ser Ala Tyr Thr Ser Glu Glu Ser Glu Asn
            45                  50                  55

gaa aac cct cat gca agg ggt tcc ttt agt tat aag tca ctc aga aag      243
Glu Asn Pro His Ala Arg Gly Ser Phe Ser Tyr Lys Ser Leu Arg Lys
        60                  65                  70

gga gga cca tca cag agg gag cag tac ctg cct ggt gcc att gcc att      291
Gly Gly Pro Ser Gln Arg Glu Gln Tyr Leu Pro Gly Ala Ile Ala Ile
    75                  80                  85

ttt aat gtg aac aac agc agc aat aag gac cag gaa cca gag gaa aaa      339
Phe Asn Val Asn Asn Ser Ser Asn Lys Asp Gln Glu Pro Glu Glu Lys
90                  95                  100                 105

aag aaa aag aaa aaa gaa aag aag agc aag tca gat gat aaa aac gaa      387
Lys Lys Lys Lys Lys Glu Lys Lys Ser Lys Ser Asp Asp Lys Asn Glu
                110                 115                 120

aat aaa aac gac cca gag aag aaa aag aag aaa aag gac aaa gag aag      435
Asn Lys Asn Asp Pro Glu Lys Lys Lys Lys Lys Lys Asp Lys Glu Lys
            125                 130                 135

aaa aag aaa gag gag aaa agc aaa gat aag aaa gaa cac cac aag aaa      483
Lys Lys Lys Glu Glu Lys Ser Lys Asp Lys Lys Glu His His Lys Lys
        140                 145                 150
```

-continued

```
gaa gtt gtg gtt att gat ccc tcg gga aac aca tat tac aac tgg ctg      531
Glu Val Val Val Ile Asp Pro Ser Gly Asn Thr Tyr Tyr Asn Trp Leu
    155                 160                 165

ttt tgc atc aca tta cct gtt atg tac aac tgg aca atg gtt att gcc      579
Phe Cys Ile Thr Leu Pro Val Met Tyr Asn Trp Thr Met Val Ile Ala
170                 175                 180                 185

aga gca tgt ttt gat gaa ctt caa tct gat tac cta gaa tat tgg ctc      627
Arg Ala Cys Phe Asp Glu Leu Gln Ser Asp Tyr Leu Glu Tyr Trp Leu
                190                 195                 200

att ttg gat tac gta tca gac ata gtc tat tta atc gat atg ttt gta      675
Ile Leu Asp Tyr Val Ser Asp Ile Val Tyr Leu Ile Asp Met Phe Val
            205                 210                 215

cga aca agg aca ggt tac cta gaa caa gga ctg ctg gta aag gaa gaa      723
Arg Thr Arg Thr Gly Tyr Leu Glu Gln Gly Leu Leu Val Lys Glu Glu
        220                 225                 230

ctt aaa ctc ata aat aaa tat aaa tcc aac ttg caa ttt aaa ctt gat      771
Leu Lys Leu Ile Asn Lys Tyr Lys Ser Asn Leu Gln Phe Lys Leu Asp
    235                 240                 245

gtt ctg tca ctg ata cca act gat ttg ctg tat ttt aag tta ggg tgg      819
Val Leu Ser Leu Ile Pro Thr Asp Leu Leu Tyr Phe Lys Leu Gly Trp
250                 255                 260                 265

aac tat cca gaa att aga tta aac agg ttg tta cgg ttc tct cgt atg      867
Asn Tyr Pro Glu Ile Arg Leu Asn Arg Leu Leu Arg Phe Ser Arg Met
                270                 275                 280

ttt gag ttc ttc cag aga aca gaa aca agg aca aac tat cca aac atc      915
Phe Glu Phe Phe Gln Arg Thr Glu Thr Arg Thr Asn Tyr Pro Asn Ile
            285                 290                 295

ttc agg att tcc aac ctt gtt atg tat atc gtc atc att atc cac tgg      963
Phe Arg Ile Ser Asn Leu Val Met Tyr Ile Val Ile Ile Ile His Trp
        300                 305                 310

aat gca tgt gtg ttc tac tct att tct aaa gct att gga ttt gga aat     1011
Asn Ala Cys Val Phe Tyr Ser Ile Ser Lys Ala Ile Gly Phe Gly Asn
    315                 320                 325

gat aca tgg gtc tac cct gat att aat gat cct gaa ttt ggc cgt ttg     1059
Asp Thr Trp Val Tyr Pro Asp Ile Asn Asp Pro Glu Phe Gly Arg Leu
330                 335                 340                 345

gct aga aaa tac gta tac agc ctt tac tgg tct aca ctg act ttg act     1107
Ala Arg Lys Tyr Val Tyr Ser Leu Tyr Trp Ser Thr Leu Thr Leu Thr
                350                 355                 360

acc att ggt gaa aca ccc cct ccc gtg agg gat tct gag tat gtc ttt     1155
Thr Ile Gly Glu Thr Pro Pro Pro Val Arg Asp Ser Glu Tyr Val Phe
            365                 370                 375

gtg gtg gtt gat ttc cta att gga gtg tta att ttt gct acc atc gtt     1203
Val Val Val Asp Phe Leu Ile Gly Val Leu Ile Phe Ala Thr Ile Val
        380                 385                 390

ggt aac ata ggt tct atg att tcc aac atg aat gca gcc aga gca gaa     1251
Gly Asn Ile Gly Ser Met Ile Ser Asn Met Asn Ala Ala Arg Ala Glu
    395                 400                 405

ttt caa gca aga att gat gct atc aag caa tat atg cat ttt cga aat     1299
Phe Gln Ala Arg Ile Asp Ala Ile Lys Gln Tyr Met His Phe Arg Asn
410                 415                 420                 425

gta agc aaa gat atg gaa aag agg gtt att aaa tgg ttt gac tac ctg     1347
Val Ser Lys Asp Met Glu Lys Arg Val Ile Lys Trp Phe Asp Tyr Leu
                430                 435                 440

tgg acc aac aaa aaa aca gtt gat gag aaa gaa gtc tta aag tat cta     1395
Trp Thr Asn Lys Lys Thr Val Asp Glu Lys Glu Val Leu Lys Tyr Leu
            445                 450                 455

cct gat aaa cta aga gca gaa att gcc atc aac gtt cac tta gac aca     1443
Pro Asp Lys Leu Arg Ala Glu Ile Ala Ile Asn Val His Leu Asp Thr
        460                 465                 470
```

```
tta aaa aag gta cgc att ttt gct gat tgt gaa gct ggt ctg ttg gtg     1491
Leu Lys Lys Val Arg Ile Phe Ala Asp Cys Glu Ala Gly Leu Leu Val
    475                 480                 485

gag ttg gtc ttg aaa ttg caa ccc caa gtc tac agt cct gga gat tat     1539
Glu Leu Val Leu Lys Leu Gln Pro Gln Val Tyr Ser Pro Gly Asp Tyr
490                 495                 500                 505

att tgc aag aaa ggg gat atc gga cga gag atg tac att atc aag gaa     1587
Ile Cys Lys Lys Gly Asp Ile Gly Arg Glu Met Tyr Ile Ile Lys Glu
                510                 515                 520

ggc aaa ctc gct gtg gtg gca gat gat gga gtc act cag ttt gtg gta     1635
Gly Lys Leu Ala Val Val Ala Asp Asp Gly Val Thr Gln Phe Val Val
            525                 530                 535

ttg agc gat ggc agc acc ttc ggt gag atc agc att ctt aac att aaa     1683
Leu Ser Asp Gly Ser Thr Phe Gly Glu Ile Ser Ile Leu Asn Ile Lys
        540                 545                 550

ggg agc aaa gct ggc aat cga aga acg gcc aat att aaa agt att ggc     1731
Gly Ser Lys Ala Gly Asn Arg Arg Thr Ala Asn Ile Lys Ser Ile Gly
    555                 560                 565

tac tca gac ctg ttc tgt ctc tca aaa gat gac ctc atg gaa gct cta     1779
Tyr Ser Asp Leu Phe Cys Leu Ser Lys Asp Asp Leu Met Glu Ala Leu
570                 575                 580                 585

act gag tac cca gat gcc aaa act atg cta gaa gaa aaa ggg aag caa     1827
Thr Glu Tyr Pro Asp Ala Lys Thr Met Leu Glu Glu Lys Gly Lys Gln
                590                 595                 600

att tta atg aaa gat ggt cta ctg gat cta aac att gca aat gct ggc     1875
Ile Leu Met Lys Asp Gly Leu Leu Asp Leu Asn Ile Ala Asn Ala Gly
            605                 610                 615

agt gat cct aaa gat ctt gaa gag aag gtt act cga atg gag ggg tca     1923
Ser Asp Pro Lys Asp Leu Glu Glu Lys Val Thr Arg Met Glu Gly Ser
        620                 625                 630

gta gac ctc ctg caa acc agg ttt gcc cga atc ttg gct gag tat gag     1971
Val Asp Leu Leu Gln Thr Arg Phe Ala Arg Ile Leu Ala Glu Tyr Glu
    635                 640                 645

tcc atg cag cag aaa ctg aaa caa aga tta acc aag gtt gag aaa ttt     2019
Ser Met Gln Gln Lys Leu Lys Gln Arg Leu Thr Lys Val Glu Lys Phe
650                 655                 660                 665

ctg aaa ccg ctt att gac aca gaa ttt tca agt att gag gga cct tgg     2067
Leu Lys Pro Leu Ile Asp Thr Glu Phe Ser Ser Ile Glu Gly Pro Trp
                670                 675                 680

agc gaa agt ggg ccc atc gac tct aca tag aaccgaaaag ctggtcatta       2117
Ser Glu Ser Gly Pro Ile Asp Ser Thr
            685                 690

acagggacat gcctcatgat ccttttgatc ctatgactga catcaactaa aatttaaaag   2177

aagaggaaga ctcagttggg aaatttttcc atgaggaaaa tgtgctttgg tgcaaggtac   2237

agcccacacc tctctgagag atactatgat taaaaaagct ttatatctgg gatttttcac   2297

aactgataat gtgcaaagat ataaactgat taacttgtca gtgtctgtat tttctgattt   2357

tttcacatac gctcatttta tgtaatattc ttcataaaaa tgaataagta gccctcactt   2417

tcatgccatt tccattgttg agtgaagcgt atttgaagta actgagaatt accatgtaca   2477

tcatatttgg gataacattt tta                                           2500


<210> SEQ ID NO 2
<211> LENGTH: 690
<212> TYPE: PRT
<213> ORGANISM: homo sapiens

<400> SEQUENCE: 2

Met Lys Leu Ser Met Lys Asn Asn Ile Ile Asn Thr Gln Gln Ser Phe
```

-continued

```
1               5                   10                  15

Val Thr Met Pro Asn Val Ile Val Pro Asp Ile Glu Lys Glu Ile Arg
            20                  25                  30

Arg Met Glu Asn Gly Ala Cys Ser Ser Phe Ser Glu Asp Asp Asp Ser
        35                  40                  45

Ala Tyr Thr Ser Glu Glu Ser Glu Asn Glu Asn Pro His Ala Arg Gly
    50                  55                  60

Ser Phe Ser Tyr Lys Ser Leu Arg Lys Gly Gly Pro Ser Gln Arg Glu
65                  70                  75                  80

Gln Tyr Leu Pro Gly Ala Ile Ala Ile Phe Asn Val Asn Asn Ser Ser
                85                  90                  95

Asn Lys Asp Gln Glu Pro Glu Glu Lys Lys Lys Lys Lys Lys Glu Lys
            100                 105                 110

Lys Ser Lys Ser Asp Asp Lys Asn Glu Asn Lys Asn Asp Pro Glu Lys
        115                 120                 125

Lys Lys Lys Lys Lys Asp Lys Glu Lys Lys Lys Lys Glu Glu Lys Ser
    130                 135                 140

Lys Asp Lys Lys Glu His His Lys Lys Glu Val Val Val Ile Asp Pro
145                 150                 155                 160

Ser Gly Asn Thr Tyr Tyr Asn Trp Leu Phe Cys Ile Thr Leu Pro Val
                165                 170                 175

Met Tyr Asn Trp Thr Met Val Ile Ala Arg Ala Cys Phe Asp Glu Leu
            180                 185                 190

Gln Ser Asp Tyr Leu Glu Tyr Trp Leu Ile Leu Asp Tyr Val Ser Asp
        195                 200                 205

Ile Val Tyr Leu Ile Asp Met Phe Val Arg Thr Arg Thr Gly Tyr Leu
    210                 215                 220

Glu Gln Gly Leu Leu Val Lys Glu Glu Leu Lys Leu Ile Asn Lys Tyr
225                 230                 235                 240

Lys Ser Asn Leu Gln Phe Lys Leu Asp Val Leu Ser Leu Ile Pro Thr
                245                 250                 255

Asp Leu Leu Tyr Phe Lys Leu Gly Trp Asn Tyr Pro Glu Ile Arg Leu
            260                 265                 270

Asn Arg Leu Leu Arg Phe Ser Arg Met Phe Glu Phe Phe Gln Arg Thr
        275                 280                 285

Glu Thr Arg Thr Asn Tyr Pro Asn Ile Phe Arg Ile Ser Asn Leu Val
    290                 295                 300

Met Tyr Ile Val Ile Ile Ile His Trp Asn Ala Cys Val Phe Tyr Ser
305                 310                 315                 320

Ile Ser Lys Ala Ile Gly Phe Gly Asn Asp Thr Trp Val Tyr Pro Asp
                325                 330                 335

Ile Asn Asp Pro Glu Phe Gly Arg Leu Ala Arg Lys Tyr Val Tyr Ser
            340                 345                 350

Leu Tyr Trp Ser Thr Leu Thr Leu Thr Thr Ile Gly Glu Thr Pro Pro
        355                 360                 365

Pro Val Arg Asp Ser Glu Tyr Val Phe Val Val Val Asp Phe Leu Ile
    370                 375                 380

Gly Val Leu Ile Phe Ala Thr Ile Val Gly Asn Ile Gly Ser Met Ile
385                 390                 395                 400

Ser Asn Met Asn Ala Ala Arg Ala Glu Phe Gln Ala Arg Ile Asp Ala
                405                 410                 415

Ile Lys Gln Tyr Met His Phe Arg Asn Val Ser Lys Asp Met Glu Lys
            420                 425                 430
```

```
Arg Val Ile Lys Trp Phe Asp Tyr Leu Trp Thr Asn Lys Lys Thr Val
        435                 440                 445

Asp Glu Lys Glu Val Leu Lys Tyr Leu Pro Asp Lys Leu Arg Ala Glu
    450                 455                 460

Ile Ala Ile Asn Val His Leu Asp Thr Leu Lys Lys Val Arg Ile Phe
465                 470                 475                 480

Ala Asp Cys Glu Ala Gly Leu Leu Val Glu Leu Val Leu Lys Leu Gln
                485                 490                 495

Pro Gln Val Tyr Ser Pro Gly Asp Tyr Ile Cys Lys Lys Gly Asp Ile
            500                 505                 510

Gly Arg Glu Met Tyr Ile Ile Lys Glu Gly Lys Leu Ala Val Val Ala
        515                 520                 525

Asp Asp Gly Val Thr Gln Phe Val Val Leu Ser Asp Gly Ser Thr Phe
    530                 535                 540

Gly Glu Ile Ser Ile Leu Asn Ile Lys Gly Ser Lys Ala Gly Asn Arg
545                 550                 555                 560

Arg Thr Ala Asn Ile Lys Ser Ile Gly Tyr Ser Asp Leu Phe Cys Leu
                565                 570                 575

Ser Lys Asp Asp Leu Met Glu Ala Leu Thr Glu Tyr Pro Asp Ala Lys
            580                 585                 590

Thr Met Leu Glu Glu Lys Gly Lys Gln Ile Leu Met Lys Asp Gly Leu
        595                 600                 605

Leu Asp Leu Asn Ile Ala Asn Ala Gly Ser Asp Pro Lys Asp Leu Glu
    610                 615                 620

Glu Lys Val Thr Arg Met Glu Gly Ser Val Asp Leu Leu Gln Thr Arg
625                 630                 635                 640

Phe Ala Arg Ile Leu Ala Glu Tyr Glu Ser Met Gln Gln Lys Leu Lys
                645                 650                 655

Gln Arg Leu Thr Lys Val Glu Lys Phe Leu Lys Pro Leu Ile Asp Thr
            660                 665                 670

Glu Phe Ser Ser Ile Glu Gly Pro Trp Ser Glu Ser Gly Pro Ile Asp
        675                 680                 685

Ser Thr
    690


<210> SEQ ID NO 3
<211> LENGTH: 3231
<212> TYPE: DNA
<213> ORGANISM: homo sapiens
<220> FEATURE:
<221> NAME/KEY: CDS
<222> LOCATION: (22)..(2586)
<223> OTHER INFORMATION: Homo sapiens phosphodiesterase 6B,
      cGMP-specific, rod, beta (congenital stationary night blindness
      3, autosomal dominant)

<400> SEQUENCE: 3

ctccagggac aggcagccac c atg agc ctc agt gag gag cag gcc cgg agc       51
                        Met Ser Leu Ser Glu Glu Gln Ala Arg Ser
                        1               5                   10

ttt ctg gac cag aac ccc gat ttt gcc cgc cag tac ttt ggg aag aaa       99
Phe Leu Asp Gln Asn Pro Asp Phe Ala Arg Gln Tyr Phe Gly Lys Lys
                15                  20                  25

ctg agc cct gag aat gtt ggc cgc ggc tgc gag gac ggg tgc ccg ccg      147
Leu Ser Pro Glu Asn Val Gly Arg Gly Cys Glu Asp Gly Cys Pro Pro
            30                  35                  40

gac tgc gac agc ctc cgg gac ctc tgc cag gtg gag gag agc acg gcg      195
Asp Cys Asp Ser Leu Arg Asp Leu Cys Gln Val Glu Glu Ser Thr Ala
        45                  50                  55
```

-continued

```
ctg ctg gag ctg gtg cag gat atg cag gag agc atc aac atg gag cgc      243
Leu Leu Glu Leu Val Gln Asp Met Gln Glu Ser Ile Asn Met Glu Arg
    60                  65                  70

gtg gtc ttc aag gtc ctg cgg cgc ctc tgc acc ctc ctg cag gcc gac      291
Val Val Phe Lys Val Leu Arg Arg Leu Cys Thr Leu Leu Gln Ala Asp
75                  80                  85                  90

cgc tgc agc ctc ttc atg tac cgc cag cgc aac ggc gtg gcc gag ctg      339
Arg Cys Ser Leu Phe Met Tyr Arg Gln Arg Asn Gly Val Ala Glu Leu
                95                  100                 105

gcc acc agg ctt ttc agc gtg cag ccg gac agc gtc ctg gag gac tgc      387
Ala Thr Arg Leu Phe Ser Val Gln Pro Asp Ser Val Leu Glu Asp Cys
            110                 115                 120

ctg gtg ccc ccc gac tcc gag atc gtc ttc cca ctg gac atc ggg gtc      435
Leu Val Pro Pro Asp Ser Glu Ile Val Phe Pro Leu Asp Ile Gly Val
        125                 130                 135

gtg ggc cac gtg gct cag acc aaa aag atg gtg aac gtc gag gac gtg      483
Val Gly His Val Ala Gln Thr Lys Lys Met Val Asn Val Glu Asp Val
    140                 145                 150

gcc gag tgc cct cac ttc agc tca ttt gct gac gag ctc act gac tac      531
Ala Glu Cys Pro His Phe Ser Ser Phe Ala Asp Glu Leu Thr Asp Tyr
155                 160                 165                 170

aag aca aag aat atg ctg gcc aca ccc atc atg aat ggc aaa gac gtc      579
Lys Thr Lys Asn Met Leu Ala Thr Pro Ile Met Asn Gly Lys Asp Val
                175                 180                 185

gtg gcg gtg atc atg gca gtg aac aag ctc aac ggc cca ttc ttc acc      627
Val Ala Val Ile Met Ala Val Asn Lys Leu Asn Gly Pro Phe Phe Thr
            190                 195                 200

agc gaa gac gaa gat gtg ttc ttg aag tac ctg aat ttt gcc acg ttg      675
Ser Glu Asp Glu Asp Val Phe Leu Lys Tyr Leu Asn Phe Ala Thr Leu
        205                 210                 215

tac ctg aag atc tat cac ctg agc tac ctc cac aac tgc gag acg cgc      723
Tyr Leu Lys Ile Tyr His Leu Ser Tyr Leu His Asn Cys Glu Thr Arg
    220                 225                 230

cgc ggc cag gtg ctg ctg tgg tcg gcc aac aag gtg ttt gag gag ctg      771
Arg Gly Gln Val Leu Leu Trp Ser Ala Asn Lys Val Phe Glu Glu Leu
235                 240                 245                 250

acg gac atc gag agg cag ttc cac aag gcc ttc tac acg gtg cgg gcc      819
Thr Asp Ile Glu Arg Gln Phe His Lys Ala Phe Tyr Thr Val Arg Ala
                255                 260                 265

tac ctc aac tgc gag cgg tac tcc gtg ggc ctc ctg gac atg acc aag      867
Tyr Leu Asn Cys Glu Arg Tyr Ser Val Gly Leu Leu Asp Met Thr Lys
            270                 275                 280

gag aag gaa ttt ttt gac gtg tgg tct gtg ctg atg gga gag tcc cag      915
Glu Lys Glu Phe Phe Asp Val Trp Ser Val Leu Met Gly Glu Ser Gln
        285                 290                 295

ccg tac tcg ggc cca cgc acg cct gat ggc cgg gaa att gtc ttc tac      963
Pro Tyr Ser Gly Pro Arg Thr Pro Asp Gly Arg Glu Ile Val Phe Tyr
    300                 305                 310

aaa gtg atc gac tac atc ctc cac ggc aag gag gag atc aag gtc att     1011
Lys Val Ile Asp Tyr Ile Leu His Gly Lys Glu Glu Ile Lys Val Ile
315                 320                 325                 330

ccc aca ccc tca gcc gat cac tgg gcc ctg gcc agc ggc ctt cca agc     1059
Pro Thr Pro Ser Ala Asp His Trp Ala Leu Ala Ser Gly Leu Pro Ser
                335                 340                 345

tac gtg gca gaa agc ggc ttt att tgt aac atc atg aat gct tcc gct     1107
Tyr Val Ala Glu Ser Gly Phe Ile Cys Asn Ile Met Asn Ala Ser Ala
            350                 355                 360

gac gaa atg ttc aaa ttt cag gaa ggg gcc ctg gac gac tcc ggg tgg     1155
Asp Glu Met Phe Lys Phe Gln Glu Gly Ala Leu Asp Asp Ser Gly Trp
        365                 370                 375
```

```
ctc atc aag aat gtg ctg tcc atg ccc atc gtc aac aag aag gag gag     1203
Leu Ile Lys Asn Val Leu Ser Met Pro Ile Val Asn Lys Lys Glu Glu
    380                 385                 390

att gtg gga gtc gcc aca ttt tac aac agg aaa gac ggg aag ccc ttt     1251
Ile Val Gly Val Ala Thr Phe Tyr Asn Arg Lys Asp Gly Lys Pro Phe
395                 400                 405                 410

gac gaa cag gac gag gtt ctc atg gag tcc ctg aca cag ttc ctg ggc     1299
Asp Glu Gln Asp Glu Val Leu Met Glu Ser Leu Thr Gln Phe Leu Gly
                415                 420                 425

tgg tca gtg atg aac acc gac acc tac gac aag atg aac aag ctg gag     1347
Trp Ser Val Met Asn Thr Asp Thr Tyr Asp Lys Met Asn Lys Leu Glu
            430                 435                 440

aac cgc aag gac atc gca cag gac atg gtc ctt tac cac gtg aag tgc     1395
Asn Arg Lys Asp Ile Ala Gln Asp Met Val Leu Tyr His Val Lys Cys
        445                 450                 455

gac agg gac gag atc cag ctc atc ctg cca acc aga gcg cgc ctg ggg     1443
Asp Arg Asp Glu Ile Gln Leu Ile Leu Pro Thr Arg Ala Arg Leu Gly
    460                 465                 470

aag gag cct gct gac tgc gat gag gac gag ctg ggc gaa atc ctg aag     1491
Lys Glu Pro Ala Asp Cys Asp Glu Asp Glu Leu Gly Glu Ile Leu Lys
475                 480                 485                 490

gag gag ctg cca ggg ccc acc aca ttt gac atc tac gaa ttc cac ttc     1539
Glu Glu Leu Pro Gly Pro Thr Thr Phe Asp Ile Tyr Glu Phe His Phe
                495                 500                 505

tct gac ctg gag tgc acc gaa ctg gac ctg gtc aaa tgt ggc atc cag     1587
Ser Asp Leu Glu Cys Thr Glu Leu Asp Leu Val Lys Cys Gly Ile Gln
            510                 515                 520

atg tac tac gag ctg ggc gtg gtc cga aag ttc cag atc ccc cag gag     1635
Met Tyr Tyr Glu Leu Gly Val Val Arg Lys Phe Gln Ile Pro Gln Glu
        525                 530                 535

gtc ctg gtg cgg ttc ctg ttc tcc atc agc aaa ggg tac cgg aga atc     1683
Val Leu Val Arg Phe Leu Phe Ser Ile Ser Lys Gly Tyr Arg Arg Ile
    540                 545                 550

acc tac cac aac tgg cgc cac ggc ttc aac gtg gcc cag acg atg ttc     1731
Thr Tyr His Asn Trp Arg His Gly Phe Asn Val Ala Gln Thr Met Phe
555                 560                 565                 570

acg ctg ctc atg acc ggc aaa ctg aag agc tac tac acg gac ctg gag     1779
Thr Leu Leu Met Thr Gly Lys Leu Lys Ser Tyr Tyr Thr Asp Leu Glu
                575                 580                 585

gcc ttc gcc atg gtg aca gcc ggc ctg tgc cat gac atc gac cac cgc     1827
Ala Phe Ala Met Val Thr Ala Gly Leu Cys His Asp Ile Asp His Arg
            590                 595                 600

ggc acc aac aac ctg tac cag atg aag tcc cag aac ccc ttg gct aag     1875
Gly Thr Asn Asn Leu Tyr Gln Met Lys Ser Gln Asn Pro Leu Ala Lys
        605                 610                 615

ctc cac ggc tcc tcg att ttg gag cgg cac cac ctg gag ttt ggg aag     1923
Leu His Gly Ser Ser Ile Leu Glu Arg His His Leu Glu Phe Gly Lys
    620                 625                 630

ttc ctg ctc tcg gag gag acc ctg aac atc tac cag aac ctg aac cgg     1971
Phe Leu Leu Ser Glu Glu Thr Leu Asn Ile Tyr Gln Asn Leu Asn Arg
635                 640                 645                 650

cgg cag cac gag cac gtg atc cac ctg atg gac atc gcc atc atc gcc     2019
Arg Gln His Glu His Val Ile His Leu Met Asp Ile Ala Ile Ile Ala
                655                 660                 665

acg gac ctg gcc ctg tac ttc aag aag aga gcg atg ttt cag aag atc     2067
Thr Asp Leu Ala Leu Tyr Phe Lys Lys Arg Ala Met Phe Gln Lys Ile
            670                 675                 680

gtg gat gag tcc aag aac tac cag gac aag aag agc tgg gtg gag tac     2115
Val Asp Glu Ser Lys Asn Tyr Gln Asp Lys Lys Ser Trp Val Glu Tyr
        685                 690                 695
```

```
ctg tcc ctg gag acg acc cgg aag gag atc gtc atg gcc atg atg atg      2163
Leu Ser Leu Glu Thr Thr Arg Lys Glu Ile Val Met Ala Met Met Met
    700                 705                 710

aca gcc tgc gac ctg tct gcc atc acc aag ccc tgg gaa gtc cag agc      2211
Thr Ala Cys Asp Leu Ser Ala Ile Thr Lys Pro Trp Glu Val Gln Ser
715                 720                 725                 730

aag gtc gca ctt ctc gtg gct gct gag ttc tgg gag caa ggt gac ttg      2259
Lys Val Ala Leu Leu Val Ala Ala Glu Phe Trp Glu Gln Gly Asp Leu
                735                 740                 745

gaa agg aca gtc ttg gat cag cag ccc att cct atg atg gac cgg aac      2307
Glu Arg Thr Val Leu Asp Gln Gln Pro Ile Pro Met Met Asp Arg Asn
            750                 755                 760

aag gcg gcc gag ctc ccc aag ctg caa gtg ggc ttc atc gac ttc gtg      2355
Lys Ala Ala Glu Leu Pro Lys Leu Gln Val Gly Phe Ile Asp Phe Val
        765                 770                 775

tgc aca ttc gtg tac aag gag ttc tct cgt ttc cac gaa gag atc ctg      2403
Cys Thr Phe Val Tyr Lys Glu Phe Ser Arg Phe His Glu Glu Ile Leu
    780                 785                 790

ccc atg ttc gac cga ctg cag aac aat agg aaa gag tgg aag gcg ctg      2451
Pro Met Phe Asp Arg Leu Gln Asn Asn Arg Lys Glu Trp Lys Ala Leu
795                 800                 805                 810

gct gat gag tat gag gcc aaa gtg aag gct ctg gag gag aag gag gag      2499
Ala Asp Glu Tyr Glu Ala Lys Val Lys Ala Leu Glu Glu Lys Glu Glu
                815                 820                 825

gag gag agg gtg gca gcc aag aaa gta ggc aca gaa att tgc aat ggc      2547
Glu Glu Arg Val Ala Ala Lys Lys Val Gly Thr Glu Ile Cys Asn Gly
            830                 835                 840

ggc cca gca ccc aag tct tca acc tgc tgt atc ctg tga gcactggtcc      2596
Gly Pro Ala Pro Lys Ser Ser Thr Cys Cys Ile Leu
        845                 850

cgtggggacc ctatggctcc ctcaatcttc acccactagg atttgggttc tgcctgtggc   2656

tatttgctac aagaggttag gaagcccaag aaaatgactg aagatcattc tggatatttt   2716

aatttttttt tttttttttt ttttgagatg gagtcttgct ctgtcaccca ggctggagtg   2776

ccgtggcacg atctcagctc actgcaacct ccacctccca ggttcaagcg attctcgtgc   2836

ctcagcctcc tgagtagctg ggactacagg cgcccaccac cacacatgct aatttttgta   2896

ttttcagtac agatggggtt tcaccatatt gggcaggctg gtctcgaact cctgacctca   2956

ggtgatcacc gcctcagctt cctgaagtgc tgggattaca ggcatgagcc accacgccca   3016

gcctgttttt ataaactgaa gccaactgtg aataaactgt agcctacatt actcatccat   3076

ttttggatag ttaccactgg gagacctttg aaaagggtcc atgaactctg aaatcactga   3136

gaacatttgc agccacacat gtacatatgt gtacacaggt agacagatgg acacaggccg   3196

tttctcatcc agtttaggaa aacacacatg ctcag                               3231

<210> SEQ ID NO 4
<211> LENGTH: 854
<212> TYPE: PRT
<213> ORGANISM: homo sapiens

<400> SEQUENCE: 4

Met Ser Leu Ser Glu Glu Gln Ala Arg Ser Phe Leu Asp Gln Asn Pro
1               5                   10                  15

Asp Phe Ala Arg Gln Tyr Phe Gly Lys Lys Leu Ser Pro Glu Asn Val
            20                  25                  30

Gly Arg Gly Cys Glu Asp Gly Cys Pro Pro Asp Cys Asp Ser Leu Arg
        35                  40                  45
```

-continued

```
Asp Leu Cys Gln Val Glu Glu Ser Thr Ala Leu Leu Glu Leu Val Gln
    50                  55                  60

Asp Met Gln Glu Ser Ile Asn Met Glu Arg Val Val Phe Lys Val Leu
65                  70                  75                  80

Arg Arg Leu Cys Thr Leu Leu Gln Ala Asp Arg Cys Ser Leu Phe Met
                85                  90                  95

Tyr Arg Gln Arg Asn Gly Val Ala Glu Leu Ala Thr Arg Leu Phe Ser
            100                 105                 110

Val Gln Pro Asp Ser Val Leu Glu Asp Cys Leu Val Pro Pro Asp Ser
        115                 120                 125

Glu Ile Val Phe Pro Leu Asp Ile Gly Val Val Gly His Val Ala Gln
    130                 135                 140

Thr Lys Lys Met Val Asn Val Glu Asp Val Ala Glu Cys Pro His Phe
145                 150                 155                 160

Ser Ser Phe Ala Asp Glu Leu Thr Asp Tyr Lys Thr Lys Asn Met Leu
                165                 170                 175

Ala Thr Pro Ile Met Asn Gly Lys Asp Val Val Ala Val Ile Met Ala
            180                 185                 190

Val Asn Lys Leu Asn Gly Pro Phe Phe Thr Ser Glu Asp Glu Asp Val
        195                 200                 205

Phe Leu Lys Tyr Leu Asn Phe Ala Thr Leu Tyr Leu Lys Ile Tyr His
    210                 215                 220

Leu Ser Tyr Leu His Asn Cys Glu Thr Arg Arg Gly Gln Val Leu Leu
225                 230                 235                 240

Trp Ser Ala Asn Lys Val Phe Glu Glu Leu Thr Asp Ile Glu Arg Gln
                245                 250                 255

Phe His Lys Ala Phe Tyr Thr Val Arg Ala Tyr Leu Asn Cys Glu Arg
            260                 265                 270

Tyr Ser Val Gly Leu Leu Asp Met Thr Lys Glu Lys Glu Phe Phe Asp
        275                 280                 285

Val Trp Ser Val Leu Met Gly Glu Ser Gln Pro Tyr Ser Gly Pro Arg
    290                 295                 300

Thr Pro Asp Gly Arg Glu Ile Val Phe Tyr Lys Val Ile Asp Tyr Ile
305                 310                 315                 320

Leu His Gly Lys Glu Glu Ile Lys Val Ile Pro Thr Pro Ser Ala Asp
                325                 330                 335

His Trp Ala Leu Ala Ser Gly Leu Pro Ser Tyr Val Ala Glu Ser Gly
            340                 345                 350

Phe Ile Cys Asn Ile Met Asn Ala Ser Ala Asp Glu Met Phe Lys Phe
        355                 360                 365

Gln Glu Gly Ala Leu Asp Asp Ser Gly Trp Leu Ile Lys Asn Val Leu
    370                 375                 380

Ser Met Pro Ile Val Asn Lys Lys Glu Glu Ile Val Gly Val Ala Thr
385                 390                 395                 400

Phe Tyr Asn Arg Lys Asp Gly Lys Pro Phe Asp Glu Gln Asp Glu Val
                405                 410                 415

Leu Met Glu Ser Leu Thr Gln Phe Leu Gly Trp Ser Val Met Asn Thr
            420                 425                 430

Asp Thr Tyr Asp Lys Met Asn Lys Leu Glu Asn Arg Lys Asp Ile Ala
        435                 440                 445

Gln Asp Met Val Leu Tyr His Val Lys Cys Asp Arg Asp Glu Ile Gln
    450                 455                 460

Leu Ile Leu Pro Thr Arg Ala Arg Leu Gly Lys Glu Pro Ala Asp Cys
465                 470                 475                 480
```

```
Asp Glu Asp Glu Leu Gly Glu Ile Leu Lys Glu Glu Leu Pro Gly Pro
                485                 490                 495

Thr Thr Phe Asp Ile Tyr Glu Phe His Phe Ser Asp Leu Glu Cys Thr
            500                 505                 510

Glu Leu Asp Leu Val Lys Cys Gly Ile Gln Met Tyr Tyr Glu Leu Gly
        515                 520                 525

Val Val Arg Lys Phe Gln Ile Pro Gln Glu Val Leu Val Arg Phe Leu
    530                 535                 540

Phe Ser Ile Ser Lys Gly Tyr Arg Arg Ile Thr Tyr His Asn Trp Arg
545                 550                 555                 560

His Gly Phe Asn Val Ala Gln Thr Met Phe Thr Leu Leu Met Thr Gly
                565                 570                 575

Lys Leu Lys Ser Tyr Tyr Thr Asp Leu Glu Ala Phe Ala Met Val Thr
            580                 585                 590

Ala Gly Leu Cys His Asp Ile Asp His Arg Gly Thr Asn Asn Leu Tyr
        595                 600                 605

Gln Met Lys Ser Gln Asn Pro Leu Ala Lys Leu His Gly Ser Ser Ile
    610                 615                 620

Leu Glu Arg His His Leu Glu Phe Gly Lys Phe Leu Leu Ser Glu Glu
625                 630                 635                 640

Thr Leu Asn Ile Tyr Gln Asn Leu Asn Arg Arg Gln His Glu His Val
                645                 650                 655

Ile His Leu Met Asp Ile Ala Ile Ile Ala Thr Asp Leu Ala Leu Tyr
            660                 665                 670

Phe Lys Lys Arg Ala Met Phe Gln Lys Ile Val Asp Glu Ser Lys Asn
        675                 680                 685

Tyr Gln Asp Lys Lys Ser Trp Val Glu Tyr Leu Ser Leu Glu Thr Thr
    690                 695                 700

Arg Lys Glu Ile Val Met Ala Met Met Met Thr Ala Cys Asp Leu Ser
705                 710                 715                 720

Ala Ile Thr Lys Pro Trp Glu Val Gln Ser Lys Val Ala Leu Leu Val
                725                 730                 735

Ala Ala Glu Phe Trp Glu Gln Gly Asp Leu Glu Arg Thr Val Leu Asp
            740                 745                 750

Gln Gln Pro Ile Pro Met Met Asp Arg Asn Lys Ala Ala Glu Leu Pro
        755                 760                 765

Lys Leu Gln Val Gly Phe Ile Asp Phe Val Cys Thr Phe Val Tyr Lys
    770                 775                 780

Glu Phe Ser Arg Phe His Glu Glu Ile Leu Pro Met Phe Asp Arg Leu
785                 790                 795                 800

Gln Asn Asn Arg Lys Glu Trp Lys Ala Leu Ala Asp Glu Tyr Glu Ala
                805                 810                 815

Lys Val Lys Ala Leu Glu Glu Lys Glu Glu Glu Glu Arg Val Ala Ala
            820                 825                 830

Lys Lys Val Gly Thr Glu Ile Cys Asn Gly Gly Pro Ala Pro Lys Ser
        835                 840                 845

Ser Thr Cys Cys Ile Leu
    850
```

<210> SEQ ID NO 5
<211> LENGTH: 21
<212> TYPE: DNA
<213> ORGANISM: Artificial Sequence
<220> FEATURE:
<223> OTHER INFORMATION: GFP target sequence -continued

```
<400> SEQUENCE: 5

gcaagctgac cctgaagttc a                                              21


<210> SEQ ID NO 6
<211> LENGTH: 19
<212> TYPE: RNA
<213> ORGANISM: Artificial Sequence
<220> FEATURE:
<223> OTHER INFORMATION: GFP dsRNA sense strand

<400> SEQUENCE: 6

gcaagcugac ccugaaguu                                                 19


<210> SEQ ID NO 7
<211> LENGTH: 19
<212> TYPE: RNA
<213> ORGANISM: Artificial Sequence
<220> FEATURE:
<223> OTHER INFORMATION: GFP dsRNA antisense strand

<400> SEQUENCE: 7

aacuucaggg ucagcuugc                                                 19


<210> SEQ ID NO 8
<211> LENGTH: 21
<212> TYPE: DNA
<213> ORGANISM: Artificial Sequence
<220> FEATURE:
<223> OTHER INFORMATION: non-silencing control target sequence

<400> SEQUENCE: 8

aattctccga acgtgtcacg t                                              21


<210> SEQ ID NO 9
<211> LENGTH: 21
<212> TYPE: DNA
<213> ORGANISM: Artificial Sequence
<220> FEATURE:
<223> OTHER INFORMATION: non-silencing control dsRNA sense strand

<400> SEQUENCE: 9

uucuccgaac gugucacgut t                                              21


<210> SEQ ID NO 10
<211> LENGTH: 21
<212> TYPE: DNA
<213> ORGANISM: Artificial Sequence
<220> FEATURE:
<223> OTHER INFORMATION: non-silencing control dsRNA antisense strand

<400> SEQUENCE: 10

acgugacacg uucggagaat t                                              21
```

MEANS AND METHODS FOR THE SPECIFIC MODULATION OF TARGET GENES IN THE CNS AND THE EYE AND METHODS FOR THEIR IDENTIFICATION

FIELD OF THE INVENTION

The present invention relates to methods for the treatment of disorders of the central nervous system (CNS) and the eye. In particular, the present invention relates to the use of compositions comprising a compound capable of modulating a target gene or gene product for the preparation of a pharmaceutical composition for the treatment of disorders of the CNS and/or the eye, wherein the composition is designed to be administered outside the blood-CNS and the blood-retina barriers. The instant invention further relates to methods of identifying and isolating nucleic acid molecules encoding polypeptides involved in CNS disorders or of the eye, methods for diagnosing said disorders as well as to transgenic animals, wherein the expression of target genes identified in accordance with the method of the invention has been modulated. In addition, the present invention relates to methods of identifying and isolating drugs that are particularly useful for the treatment of disorders related to the CNS and/or the eye.

Several documents are cited throughout the text of this specification. Each of the documents cited herein (including any manufacturer's specifications, instructions, etc.) are hereby incorporated herein by reference; however, there is no admission that any document cited is indeed prior art as to the present invention.

BACKGROUND ART

A variety of approaches currently exist for delivering biologically active agents to the CNS and/or the eye. These include, among possible others, oral administration, intravenous-, intramuscular- and transcutaneous administration as well as intra-bulbous injection or application as eye-drops. If the drug is delivered into the systemic circulation, it is being carried to all internal organs and tissues and it has to pass through the blood-brain and/or blood retina barrier (in order to access the CNS and/or the inner parts of the eye). Obviously, all other organs are being exposed to the drug, which may lead to a high incidence of side effects, particularly when the drug exerts its effects on target genes or gene products, which are not specific for the disorder to be treated and/or the target cell or tissue.

Another strategy often employed in brain delivery is the use of invasive methods such as intraventricular infusion systems, intracerebral (polymeric) implants, transplantation of genetically engineered protein-secreting cells and cell implants. These methods are unfortunately only effective for drug delivery to the surface of the brain or to cells immediately adjacent to the depot or infusion site and can be used for example in the treatment of carcinomatous infiltration of the meninges. However, these methods have many limitations because effective drug concentrations in brain parenchyma cannot be achieved.

Like the human central nervous system the human eye is an organ characterized by high complexity and the coordinated functioning of numerous specific structures and tissues. Both are protected by barriers (tear secretion, enzymes, transport mechanisms, blood-retina and blood-CNS barrier) against harmful environmental influences. Like the blood-brain barrier, the blood-retina barrier also represents a physiological barrier for the uptake of medication by the inner part of the eye, and makes pharmacological therapy of ocular diseases very difficult indeed—if at all possible—at the present state of technology.

Medication currently available on the market for the treatment of disorders of the CNS including ophthalmological diseases is therefore almost exclusively available for treatment of clinical symptoms often associated with side effects due to the high doses necessary. A causal therapy of the CNS, and particularly of the back sections of the eye, was not possible apart from the injections. Furthermore, the current state of information on the complex molecular metabolic interrelationship underlying the etiology of retinal diseases of multi-factorial origin is only limited. Consequently, medicaments available on the market are suitable to treat the symptoms of such diseases only.

In view of the need of therapeutic means for the treatment of diseases related to CNS and/or the eye, the technical problem of the present invention is to provide means and methods for the identification and modulation of genes involved in disorders of the CNS and/or the eye. More specifically, the technical problem of present invention is to provide non-invasive methods for the controlled modulation of target genes and gene products in the mammalian CNS and/or eye while overcoming the blood-brain and/or blood retina barrier without injuring it.

The solution to said technical problem is achieved by providing the embodiments characterized in the claims, and described further below.

SUMMARY OF THE INVENTION

The present invention is directed to a method for the treatment of a disorder of the central nervous system (CNS) and/or the eye comprising administering to a subject a composition comprising a compound capable of modulating a target gene or gene product in a therapeutically effective amount, wherein said composition is administered outside the blood-brain and/or the blood-retina barriers. In particular, said composition can comprise one or more double-stranded oligoribonucleotides (dsRNA), which mediate an RNA interference of the corresponding mRNA of one or more target genes.

In another aspect, the present invention is directed to a method of identifying and isolating a nucleic acid molecule encoding a polypeptide involved in a disorder of the CNS and/or the eye comprising the steps of:

(a) culturing a cell, tissue or non-human animal under stress conditions which lead to simulation of a pathological condition related to a CNS or eye disorder;
(b) isolating nucleic acids and/or proteins from a sample of said cell, tissue or animal;
(c) comparing the expression or activity profile of at least one of said nucleic acids and/or proteins with that of a corresponding non-treated cell, tissue or animal, and/or with that of a cell, tissue or animal, which has been treated under different stress conditions;
(d) determining at least one nucleic acid and/or protein which is differentially expressed, whereby a change of expression or of the active amount of said at least one nucleic acid or activity of at least one of said proteins or an altered localization of the protein is indicative for its role in a disorder of the CNS or eye.

The present invention also relates to nucleic acid molecules obtainable by the method described above, particularly if the encoded polypeptide is involved in angiogenesis and/or neovascularization and/or retinal disorder as well as to vectors comprising such nucleic acid molecules and host cells comprising said vector.

The present invention is also directed to a method for the production of a polypeptide capable of inducing a responsive change in a phenotype comprising culturing said host cell under conditions allowing the expression of the polypeptide and recovering the produced polypeptide from the culture as well as to polypeptides obtainable by said method or encoded by the nucleic acid molecules mentioned above.

Furthermore, the present invention relates to an antibody specifically recognizing such a polypeptide and pharmaceutical and/or diagnostic compositions comprising such an antibody or any one of the above described nucleic acid molecules, nucleic acid molecules which are complementary to such a nucleic acid molecules, vectors, host cells, and/or polypeptides, and optionally a pharmaceutically acceptable carrier and suitable means for detection, respectively.

In addition, the present invention is directed to methods for treating a disorder of the CNS and/or the eye comprising administering to the subject said pharmaceutical compositions in an effective dose, Furthermore, the present invention relates to a method for detecting expression of a gene involved in a disorder of the CNS and/or eye comprising:

(a) obtaining mRNA from a cell;
(b) incubating the mRNA so obtained with a probe comprising a nucleic acid molecule described above or a fragment thereof under hybridizing conditions; and
(c) detecting the presence of mRNA hybridized to the probe; or
(a) obtaining a cell sample from the subject;
(b) contacting the cell sample so obtained with an antibody described above; and
(c) detecting the presence of the antibody bound to the protein encoded by said gene.

The invention furthermore is directed to a method for diagnosing in a subject said disorder or a predisposition to such disorder which comprises:

(a) isolating DNA from patient suffering from the disorder;
(b) digesting the isolated DNA of step (a) with at least one restriction enzyme;
(c) electrophoretically separating the resulting DNA fragments on a sizing gel;
(d) incubating the resulting gel with a probe comprising a nucleic acid molecule of the invention or a fragment thereof labeled with a detectable marker;
(e) detecting labeled bands on a gel which have hybridized to the probe as defined to create a band pattern specific to the DNA of patients of the disorder;
(f) preparing subject's DNA by steps (a) to (e) to produce detectable labeled bands on a gel; and
(g) comparing the band pattern specific to the DNA of patients of the disorder of step (e) and the subject's DNA of step (f) to determine whether the patterns are the same or different and to diagnose thereby the disorder or a predisposition to the disorder, if the patterns are the same; or
(a) analyzing a sample of nucleic acids of a subject by means of a diagnostic chip, primer extension, single nucleotide polymorphisms or sequencing comprising a nucleic acid molecule as described above; and
(b) comparing the result with that of a sample obtained from a patient suffering from the disorder;

wherein the identity of expression profile and/or nucleotide sequence is indicative for the disorder.

In further embodiment, the present invention relates to a method of determining whether a test substance has an effect on a nucleic acid molecule or polypeptide involved in a CNS or eye disorder comprising the steps:

(a) contacting a cell which expresses the target gene or gene product identified and isolated in accordance with the above described method with a compound to be screened; and
(b) determining if the compound modulates the expression or the activity of said target gene or gene product.

In a further aspect, the present invention relates to a drug or prodrug for the treatment of a disorder as defined above comprising:

(a) synthezising a test substance or a collection of test substances;
(b) subjecting said the test substance or collection of test substances to the screening method of the invention; and
(c) producing a compound identified as a modulator of a target gene or gene product or a derivative thereof.

In addition, the present invention is directed to a transgenic non-human animal which displays an aberrant expression or activity of the target gene or gene product defined above and to its use for a process in drug discovery for the treatment of said disorder.

DETAILED DESCRIPTION OF THE INVENTION

The present invention relates to the use of a compound capable of modulating a target gene or gene product for the preparation of a pharmaceutical composition for the treatment of a disorder of the central nervous system (CNS) and/or the eye, wherein said composition is designed to be applied outside the blood-CNS and/or blood-retina barriers.

In one aspect, the present invention is based on the surprising finding that the blood-retina barrier could be overcome by the administration of compounds not considered to be capable of doing so in the therapy of ocular diseases by specific modulation of protein function in the tissues of the eye. Due to the functional similarity of the blood-retina barrier to the blood-brain barrier, providing an improved method to overcome the blood-retina barrier with the aim to treat a given eye disease is expected to be suitable for the treatment of CNS disorders, too.

Hence, in accordance with the present invention the compositions comprising a compound capable of modulating a target gene or gene product in the CNS or the eye are preferably designed to be administered without any substantial, i.e. substantially effective amount of delivery-enhancing agents facilitating passage of compounds through the blood-brain barrier and/or without the necessity of applying invasive methods and devices; see, e.g., those compounds, methods and devices described in U.S. 2002183683 and WO03/000018. However, for some embodiments, which represent independent aspects of the invention, such as the use of compounds mediating RNA interference, the use of such methods and compounds may be encompassed for the enhanced and controlled delivery of a compound capable of modulating a target gene or gene product into the mammalian CNS and/or eye while circumventing the blood-brain and blood-retina barriers.

Those later embodiments are based, inter alia, on the provision of novel methods that overcome the difficulty of the application of conventional experimental strategies for the identification of genes, which cause CNS disorders and/or eye diseases, and their validation as targets for diagnosis and for pharmacological intervention strategies. This applies especially for AMD, since the symptoms of this disorder appear only late, generally in the $7^{th}$ decade of life. The current state of knowledge regarding the pathological metabolic interrelationships is not sufficient for the medical treatment of most CNS and eye diseases. Suitable animal or cell culture models are not available for such diseases, due to the complexity of the disease patterns and the lack of appropriate strategies for simple intervention and manipulation in the CNS and at the eye.

Hence, in one important aspect, the present invention relates to a cell, tissue and animal model based assay for the identification and isolation of target genes and gene products involved in disorders of the CNS and/or the eye and their use as targets for therapeutic intervention and/or diagnosis of such disorders.

Examples for CNS disorders are, for example, Alzheimer's disease, Parkinson disease, depression, bipolar disorder, schizophrenia, amnesia, migraine-headache, stroke, insomnia, alcohol abuse, anxiety, obsessive compulsive disorder, cerebral acquired human immuno-deficiency syndrome, chronic pain and many others.

The compositions of the invention may be administered locally or systemically e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as interleukins or interferons depending on the intended use of the pharmaceutical composition.

In accordance with the present invention the pharmaceutical compositions are administered to a subject in an effective dose of between about 0.1 μg to about 10 mg units/day and/or units/kg body weight; see also infra. Furthermore, the appropriate dosage regimen can be determined according to Example 21.

In a preferred embodiment, the disorder to be treated is related to eye. Such disorders include chorioretinitis and herpes retinitis, which may be considered as acquired forms of retinal disease, the majority of retinal disease disorders are reduced to a genetic predisposition. These include for example primary retinal detachment (ablatio retinae), retinal blastoma, retinal astrocytoma (Bourneville-Pringle), angiomatosis retinae (Hippel-Lindau), Coat's disease (exudative retinitis), Eale's disease, central serous retinopathy, ocular albinism, retinitis pigmentosa, retinitis punctata albescens, Usher syndrome, Leber's congenital amaurosis, cone dystrophy, vitelliform macular degeneration (Best's disease), juvenile retinoschisis, North Carolina macular dystrophy, Sorsby's fundus dystrophy, Doyne's honey comb retinal dystrophy (Malattia Leventinese), Stargardt's disease, Wagner vitreoretinal degeneration or Age-related macular degeneration (AMD) as well as single-gene retinopathies like Morbus Best or Morbus Stargardt. Various genetic defects are known which lead or predispose to this wide range of eye disease phenotypes.

Some of these clinical phenotypes are characterized by a pathological de novo generation of blood vessels, which is called neoangiogenesis or neovascularization. Starting from the choriokapillaris, the growth of new blood vessels into the inner eye then leads to an increasing degeneration of photoreceptor cells in the affected areas of the human retina. In the field of opthalmology, one can distinguish between two forms of neovascularization: subretinal (choroidal=CNV) neovascularization and retinal neovascularization. Subretinal neovascularization, which is also called subfoveal neovascularization, is associated with degenerative disorders like Makular degeneration and characterized by loss of visual acuity and metamorphopsy. On the other hand, retinal neovascularization, vitreous body or Iris neovascularization is associated with ischemic processes (e.g. retinal vasculitis and diabetic retinopathy). Furthermore, neoangiogenesis is an important pathomechanism in different, non ophthalmological disease patterns such as tumor growth, arthritis and diabetic nephropathy. Therefore, in a preferred embodiment of the methods and uses of the present invention said disorder to be treated is related to angiogenesis and/or neovascularization and particularly preferred to the retinal pigment epithelium (RPE), neurosensory retina and/or choriodea. Most preferred, the disorder is wet age-related macular degeneration (AMD) or diabetic retinopathy.

The following description deals with AMD as example for a complex eye disease with a genetic component. Considering the wet form of AMD, it also serves as an example for a disease pattern, which is characterized by a distinct neovascularization. The example shall illustrate the associated technical problems with reference to the study of molecular causes and the development of diagnostic and pharmacological intervention strategies.

AMD, which can be thought as a sub-type of retinal degeneration, is the most common cause of visual morbidity in the developed world with a prevalence increasing from 9% in persons over 52 years to more than 25% in persons over the age of 75 (Paetkau et al. 1978, Leibowitz et al. 1980, Banks and Hutton 1981, Ghafour et al. 1983, Hyman 1987, Hyman et al. 1983, Grey et al. 1989, Yap and Weatherill 1989, Heiba et al. 1994).

An early stage in the evolution of AMD pathology is accompanied by an increasing accumulation of yellowish lipofuscin-like particles within the retinal pigment epithelium (RPE; Feeney 1978). It is thought that these particles represent remnants of undigested phagocytosed photoreceptor outer segment membranes which, in the normal process, are excreted basally through Bruch's membrane into the choriocapillaris. Over time, accumulation of lipofuscin-like particles affect Bruch's membrane and lead to its progressive destruction (Hogan and Alvarado 1967, Sarks 1976, Feeney-Burns and Ellersieck 1985, Pauleikhoffet al. 1990). The deposits in the RPE and Bruch's membrane consists largely of lipids although their exact composition may vary between individuals with some deposits revealing more polar phospholipids while others contain predominantly apolar neutral lipids.

These individual differences in drusen composition are thought to be the basis for the clinical heterogeneity in AMD (Green et al. 1985). While some patients present with an ingrowth of vessels from the choriocapillaris through Bruch's membrane (neovascularization) (Bressler et al. 1982), others show pigment epithelial detachment due to excudation underneath the RPE (Gass 1967, Green et al. 1985), and a third group of patients experiences a slow decrease of visual loss due to atrophic changes in the RPE and the overlying sensory neuroretina (Maguire and Vine 1986).

Although much less common the excudative/neovascular form of AMD accounts for more than 80% of blindness with a visual acuity of $\leqq$20/200 (Bressler et al. 2002). In contrast to the above described "dry" form of AMD, the exudative "wet" AMD is associated with a choroidal neovascularization (CNV), leading to blindness and, thus, to a loss of life quality (followed by psychic disorders, increased risk of injury etc; Bressler et al. 2002). There is a high risk of developing (>40%) CNV in the second eye within 5 years of the development of CNV-AMD in the first eye (Bressler et al. 2002). Neovascular AMD is characterized by choroidal neovascular lesions. These lesions develop when abnormal blood vessels from the choroid grow and proliferate through breaks in the Bruch membrane to beneath the retinal pigment epithelium (Bressler et al. 2002, Campochiaro et al. 1999). The abnormal leakage from these vessels can result in hemorrhage or detachment of the retinal pigment epithelium or the neurosensory retina (which overlies the retinal pigment epithelium). Accompanying scar formation can replace retinal tissue and result in permanent vision loss.

AMD is a complex disease caused by exogenous as well as endogenous factors (Meyers and Zachary 1988; Seddon et al. 1997). In addition to environmental factors, several personal risk factors such as hypermetropia, light skin and iris colour, elevated serum cholesterol levels, hypertension or cigarette smoking have been suggested (Hyman et al. 1983, Klein et al. 1993, Sperduto and Hiller 1986, The Eye Disease Case-Control Study Group 1992, Bressler and Bressler 1995). A genetic component for AMD has been documented by several groups (Gass 1973, Piguet et al. 1993, Silvestri et al. 1994) and has lead to the hypothesis that the disease may be triggered by environmental/individual factors in those persons who are genetically predisposed. The number of genes which, when mutated, can confer susceptibility to AMD is not known but may be numerous.

The late onset of symptoms generally in the 7th decade of life as well as the clinical and likely genetic heterogeneity make it difficult to apply conventional approaches for the identification of genes predisposing to AMD. Due to the complexity of the clinical phenotype, it may be assumed that the number of genes is large, which, when mutated contribute to AMD susceptibility.

With recent physical approaches for the treatment of AMD such as laser photocoagulation, photodynamic therapy (using verteprofin, trade name Visudyne®, Novartis), irradiation or surgical therapies, success was only achieved with a moderate percentage of the patients (Bressler et al. 2002, Yuzawa et al. 2001).

Hence, the methods, uses and compositions of the present invention described herein represent an important improvement and alternative therapeutic intervention for the treatment of this particular disease as well as of others. For those embodiments the pharmaceutical compositions are preferably designed to be effective in (and applied to) the posterior segment of the eye, preferably in a form designed to be applied outside the retinal region of the blood-retina barrier.

In one embodiment of the invention said compound is an inhibitor/antagonist of said target gene or gene product and preferably inhibits the expression of a gene or the activity of a gene product involved in angiogenesis and/or neovascularization; see supra.

The term "antagonist/inhibitor" in accordance with the present invention includes chemical agents that modulate the action of a gene or the activity of a gene product either through altering its enzymatic activity or through modulation of expression, e.g., by affecting transcription or translation. In some cases the antagonist/inhibitor may also be a substrate of a a gene product involved in the disorder or a ligand binding molecule.

The term "inhibitor" includes both substances which reduce the activity of the polypeptide and those which nullify it altogether.

An "antagonist" that modulates the activity of the gene product and causes for example a response in a cell based assay described below, refers to a compound that alters directly or indirectly the activity the gene product or the amount of active product. The effect of an antagonist may be observed as a blocking of agonist-induced activation of a target gene. Antagonists include competitive as well as non-competitive antagonists. A competitive antagonist (or competitive blocker) interacts with or near the site specific for agonist binding. A non-competitive antagonist or blocker inactivates the function of the gene product by interacting with a site other than the agonist interaction site. Preferably, the antagonist/inhibitor is small chemical agent which directly interacts with the target gene product involved in the disorder, preferably with a gene product involved in angiogenesis and/or neovascularization. Therefore, there will preferably be a direct relationship between the molar amount of compound required to inhibit or stimulate the target gene activity and the molar amount of gene product present or lacking in the cell. The compounds can be derived from a polypeptide, an anti-polypeptide antibody, an RNA molecule encoding (part of) a polypeptide or its antisense sequence, a transcription regulator, a ligand binding molecule, a polypeptide substrate or a known agonist/activator or antagonist/inhibitor.

In a preferred embodiment of the present invention said antagonist is based on nucleic acids, for example a ribozyme, antisense or sense nucleic acid molecules to said gene or gene or dsRNA molecules which are capable of mediating RNA interference. Methods and computer programs for the preparation rational selection of for example antisense oligonucleotide sequences are described in the prior art; see for example Smith, Eur. J. Pharm. Sci. 11 (2000), 191-198; Toschi, Methods 22 (2000), 261-269; Sohail, Adv. Drug Deliv. Rev. 44 (2000), 23-34; Moulton, J. Comput. Biol. 7 (2000), 277-292. These procedures comprise how to find optimal hybridization sites, and secondly on how to select sequences that bind to for example mRNAs overexpressed in a CNS or eye disorder. These methods can include the more empirical testing of large numbers of mRNA complementary sequences to the more systematic techniques, i.e. RNase H mapping, use of combinatorial arrays and prediction of secondary structure of mRNA by computational methods. Structures that bind to structured RNA, i.e. aptastructures and tethered oligonucleotide probes, and foldback triplex-forming oligonucleotides can also be employed for the purpose of the present invention. Relating to selection of antisense sequences by aid of computational analysis, valuable www addresses are given below.

In a particularly preferred embodiment of the present invention said antagonist/inhibitor substantially consists of ribonucleotides which preferably contain a portion of double-stranded oligoribonucleotides (dsRNA). Secondary structure prediction and in vitro accessibility of mRNA as tools in the selection of target sites is described for example in Amarzguioui, Nucleic Acids Res. 28 (2000), 4113-4124. Minimising the secondary structure of DNA targets by incorporation of a modified deoxynucleoside: implications for nucleic acid analysis by hybridisation is described in Nguyen, Nucleic Acids Res. 28 (2000), 3904-3909.

dsRNA between 21 and 23 nucleotides in length is preferred. The dsRNA molecule can also contain a terminal 3'-hydroxyl group and may represent an analogue of naturally occurring RNA, differing from the nucleotide sequence of said gene or gene product by addition, deletion, substitution or modification of one or more nucleotides. General processes of introducing an RNA into a living cell to inhibit gene expression of a target gene in that cell comprising RNA with double-stranded structure, i.e. dsRNA or RNAi are known to the person skilled in the art and are described, for in WO99/32619, WO01/68836, WO01/77350, WO00/44895, WO02/055692 and WO02/055693, the disclosure content of which is hereby incorporated by reference.

The target mRNA of said dsRNA is preferably encoded by gene or a cDNA obtained in accordance with the method of the present invention described below. In one embodiment the target nucleotide sequence encodes an amino acid sequence of SEQ ID NO: 2 or 4 and/or comprises a nucleotide sequence of SEQ ID NO: 1 or 3.

In one embodiment of the invention the compound to be used in the compositions is a nucleic acid molecule or encoded by a nucleic acid molecule and is designed to be expressed in cells of the CNS and/or eye. For those embodiments gene therapy intervention is envisaged; see also infra.

In a preferred embodiment of the methods and uses of the present invention the composition is in a form designed to be introduced into the cells or tissue of the CNS or eye by a suitable carrier, characterized by the application occurring outside the blood-CNS and/or blood-retina barriers, for instance as eye drops. It can also be administered systemically, iontophoretically or by retrobulbar injection.

Iontophoresis has been defined as the active introduction of ionised molecules into tissues by means of an electric current. The technique has been used to enhance drug delivery into tissues underlying the donor electrode (e.g. skin) as well as to the general blood circulation, thus providing systemic delivery of a drug to the entire body. Iontophoresis devices require at least two electrodes, both being in electrical contact with some portion of a biological membrane surface of the body. One electrode commonly referred to as the "donor" or "active" electrode, is the electrode from which the biologically active substance, such as a drug or prodrug, is delivered into the body. Another electrode having an opposite polarity functions to complete the electric circuit between the body and the electrical power source. This electrode is commonly referred to as the "receptor" or "passive" electrode. During iontophoresis, an electrical potential is applied over the electrodes, in order to create an electrical current to pass through the drug solution and the adjacent tissue. Iontophoresis has been described for the treatment of blood-vessel related disorders (e.g. restenosis), bladder, uterus, urethra and prostate disorders. U.S. Pat. Nos. 6,219,557; 5,588,961; 5,843016; 5,486,160; 5,222,936; 5,232,441; 5,401,239 and 5,728,068 disclose different types of iontophoresis catheters for insertion into hollow, tubular organs (bladder, urethra and prostate) or into blood vessels. U.S. 2002183683 suggests the method for delivery of active substances into the CNS.

Numerous active, often specifically expressed genes are required to perform and control the processes in the cells of the CNS and the retina and the metabolic exchanges across the blood-CNS and blood-retina barrier. Specific genetic activity is also necessary for maintaining the structure and functional integrity of numerous components of these complex tissues. As a consequence, this unique and highly evolved system is especially susceptible to various genetic defects, thus leading to a wide range of disease phenotypes. While studying monogenetic disorders is relatively easy, provided the patients are members of a family sufficiently large enough to allow positional cloning, the identification of genes that contribute to multigeneic disorders or confer or susceptibility to a disease is far more difficult.

Hence, in another aspect the present invention relates to a method of identifying and isolating a nucleic acid molecule encoding a polypeptide involved in a disorder of the CNS and/or the eye comprising:

(a) culturing a cell, tissue or non-human animal under stress conditions which lead to simulation of a pathological condition related to a CNS or eye disorder;
(b) isolating nucleic acids and/or proteins from a sample of said cell, tissue or animal;
(c) comparing the expression or activity profile of at least one of said nucleic acids and/or proteins with that of a corresponding non-treated cell, tissue or animal, and/or with that of a cell, tissue or animal, which has been treated under different stress conditions;
(d) determining at least one nucleic acid and/or protein which is differentially expressed, whereby a change of expression or of the active amount of said at least one nucleic acid or activity of at least one of said proteins or an altered localization of the protein is indicative for its role in a disorder of the CNS or eye.

First, a cell, tissue or non-human animal is cultured under stress conditions which lead to simulation of a pathological condition related to a CNS or eye disorder. Preferably, said method is a cell culture based method. Preferred cells and tissue investigated (either in culture or comprised in a test animal) are those which belong to the CNS and/or eye, for example neuronal cells, glial cells, retinal cells, etc.

In a particular preferred embodiment of the method of the present invention said cell is an RPE cell or an established cell line derived from an RPE cell such as the cell line ARPE-19; see also infra. The isolation of RPE cells is described, e.g., in Example 1 below. ARPE-19 cell line is described in Dunn et al., Exp. Eye Res. 62 (1996), 155-169. For example, ARPE-19 cell line is particularly suitable for mimicking the repair response observed in vivo during proliferative vitreoretinopathy by vitreous treatment.

The mentioned stress condition can be generated by an aberrant supply of the cell, tissue or animal culture conditions and comprise, for example, oxidative stress, hypoxic culture conditions, insufficient nutrition and/or supply with growth factors, change of pH-value and/or pathophysiological concentration of rod outer segments (ROS) and/or A2-E; see also Examples 3 to 10. Preferred stress conditions are those conferred by pathophysiological concentration of rod outer segments (ROS) and/or A2-E. As an example the tissue of the interior segment of the eye can be supplied in an aberrant manner, which is a preferred embodiment of the method of the invention. Table 1 shows commonly marker genes, whose altered expression indicates apoptosis, hypoxic culture conditions or oxidative stress and which can thereby be used to verify and/or quantify the applied stress and the cellular response, respectively.

A further step of the method of the present invention involves isolating the nucleic acids and/or proteins from a sample of said cell, tissue or animal and in a further step comparing the expression or activity profile of at least one of said nucleic acids and/or proteins with that of a corresponding non-treated cell, tissue or animal, and/or with that of a cell, tissue or animal, which has been treated under different stress conditions. The isolation of nucleic acids and proteins can be done by methods known to the person skilled in the art and described in the cited literature; see also Examples 11 and 12.

In the last step at least one nucleic acid and/or protein which is differentially expressed is determined, whereby a change of expression or of the active amount of said at least one nucleic acid or activity of at least one of said proteins or an altered localization of the protein is indicative for its role in a disorder of the CNS or eye.

In one embodiment of the screening method of the invention the expression of nucleic acids is analyzed with an expression array and/or realtime PCR. Chip and array technology are well known to the person skilled in the art; see also Examples 14 to 20. Advances in approaches to DNA-based diagnostics are reviewed, for example, by Whitcombe et al. in Curr. Opin. Biotechnol. 9 (1998), 602-608. Furthermore, DNA chips and microarray technology devices, systems, and applications are described by, e.g. Cuzin, Transfus. Clin. Biol. 8 (2001), 291-296 and Heller, Annu. Rev. Biomed. Eng. (2002), 129-153. Likewise, biomedical applications of protein chips is known and described in, e.g., Ng, J. Cell. Mol. Med. 6 (2002), 329-340.

In another embodiment the protein expression is analyzed with immunoblot or ELISA assay, or 2 D gel electrophoresis or MALDI-TOF and particularly preferred antibodies are used which are specific for proteins involved in angiogenesis and/or neovascularization.

Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publication, including Sambrook et al., (1989) Molecular Cloning: A Laboratory Manual, 2nd ed., Cold Spring Harbor Laboratory Press. Candidate nucleic acids or encoded polypeptides identified in such a manner can be validated by expressing them and observing the phenotype. A further embodiment of the screening method therefore comprises the overexpression or inhibition of expression of the identified candidate nucleic acid or encoded polypeptide in said cell, tissue or animal for their capability of inducing a responsive change in the phenotype of said cell, tissue or animal, wherein said phenotype is related to a disorder of the CNS or eye.

The responsive change in the phenotype of said cells can be observed by subjecting the cells, secreted factors thereof, or cell lysates thereof, to endothelial cell cultures; and/or analyzing different parameters like cell proliferation, electrophysiological activity, DNA synthesis, out-growth of cells, cell migration, chemokinesis, chemotaxis, development of vessels, marker gene expression or activity, apoptosis and/or vitality. Examples for such assays are:

Proliferating cell nuclear antigen assay (PCNA) or TUNEL-assay are described in Montesano, R.: Regulation of angiogenesis in vitro. Eur J Clin Invest, 22: 504-515, 1992. Montesano, R. et al.: Basic fibroblast growth factor induces angiogenesis in vitro. Proc Natl Acad Sci USA, 83: 7297-7301, 1986. Holmgren, L. et al.: Dormancy of mictrometastases: Balanced proliferation and apoptosis in the presence of angiogenesis suppression. Nature Med, 1: 149-153, 1995.

Boyden chamber assay is described in Holmgren, L. et al.: Dormancy of mictrometastases: Balanced proliferation and apoptosis in the presence of angiogenesis suppression. Nature Med, 1: 149-153, 1995. Albini, A. et al.: A rapid in vitro assay for quantitating the invasive potential of tumor cells. Cancer Research, 47: 3239-3245, 1987. Hu, G. et al.: Angiogenen promotes invasiveness of cultured endothelial cells by stimulation of cell-associated proteolytic activities. Proc Natl Acad Sci USA, 6: 12096-12100, 1994. Alessandri, G. et al.: Mobilization of capillary endothelium in vitro induced by effectors of angiogenesisi in vivo. Cancer res, 43: 1790-1797, 1983.

Aortic ring angiogenesis assay is described in Zuh, W. H., et al.: Regulation of vascular growth and regression by matrix metalloproteinases in the rat aorta model of angiogenesis. Lab Invest, 80: 545-555, 2000. Kruger, E A. et al.: UCN01, a protein kinase C inhibitor, inhibits endothelial cell proliferation and angiogenic hypoxic response. Invasion Metastas, 18: 209-218, 2000. Kruger, E. A. et al.: Endostatin inhibits microvessel formation in the rat aortic ring angiogenesis assay. Biochem Biophys Res Commun, 268: 183-191, 2000. Bauer, K. S. et al.: Inhibition of angiogenesis by thalidomide requires metabolic activation, which is species dependent. Biochem Pharmacol, 55: 1827-1834, 1998. Bauer, K. S. et al.: Carboxyamidotriazole inhibits angiogenesis by blocking the calcium-mediated nitric-oxide synthase-vascular endothelial growth factor pathway. J Pharmacol Exp Ther, 292: 31-37, 2000. Berger, A. C. et al.: Endothelial monocyte activating polypeptide III induces endothelial cell apoptosis and may inhibit tumor angiogenesis. Microvasc Res, 60: 70-80, 2000.

Saphenous vein angiogenesis assay is described in Kruger, E. A. et al.: Endostatin inhibits microvessel formation in the rat aortic ring angiogenesis assay. Biochem Biophys Res Commun, 268: 183-191, 2000.

Comes mircropocket assay is described in Gimbrone, E. A. et al: Tumor growth and neovascularization: an experimental model using the rabbit cornea. J Natl Cancer Inst, 52: 413-427, 1974. Kenyon, B. M. et al.: A model of angiogenesis in the mouse cornea. Invest Ophthalmol Vis Sci, 37: 1625-1632, 1996. Kenyon, B. M. et al.: Effects of thalidomide and related metabolites in a mouse corneal model of neovascularization. Exp Eye Res, 64: 971-978, 1997. Proia, A. D. et al.: The effect of angiostatic steroids and beta-cyclodextrin tetradecasulfate on corneal neovascularization in the rat. Exp Eye Res, 57: 693-698, 1993.

Chick embryo chorioallantoic membrane assay is described in Knighton, D. et al.: Avascular and vascular phases of tumor growth factor in the chicken embryo. Br J Cancer, 35: 347-356, 1977. Auerbach, R. et al.: A simple procedure for the long-term cultivation of chicken embryos. Dev Biol, 41: 391-394, 1974. Ausprunk, D. H. et al.: Differentiation of vascular endothelium in the chick chorioallantois: A structural and autoradiographic study. Dev Biol, 38: 237-248, 1974. Nguyen, M. et al.: Quantitation of angiogenesis and antiangiogenesis in the chick embryo chorioallantoic membrane. Microvasc Res, 47: 31-40, 1994.

Furthermore a sample of said cells can be treated with an inhibitor specific for the candidate nucleic acid or encoded polypeptide to be validated and in a second step it is determined whether said cells, secreted factors thereof or cell lysates thereof have lost their capability of inducing the responsive change in the phenotype observed when no inhibitor is used. In a preferred embodiment the phenotype is angiogenesis and/or neovascularization. As an inhibitor the molecules described above can be used. Preferably, siRNA technique is used for inhibiting the expression of the target gene. A collection of protocols for siRNA-mediated knockdown of mammalian gene expression, which can be adapted to a method of the invention as mentioned herein is described for example in Elbashir et al., Methods 26 (2002), 199-213 and Martinez et al., Cell 110 (2002), 563-574.

For the development of assays and drugs for treatment of disorders caused by the genes it is often necessary to identify the sequence of those nucleic acids and/or proteins, and optionally identifying the corresponding encoding gene or cDNA as well. Based on the specific functions of the cells of the CNS and/or eye specific, it is presumed that genes, the aberrant function of which cause a CNS or eye disease, are specifically expressed in the respective tissues and cells, thus representing preferred targets for drug interventions. Therefore, the identified gene, cDNA or a fragment thereof is usually also cloned and nucleic acid molecules obtainable by the methods described herein form also part of the invention, particularly if they encode polypeptides involved in angiogenesis and/or neovascularization. Such a nucleic acid molecule can be DNA or cDNA and be derived from a mammal and in a preferred embodiment is from a mouse or a human.

Hence, in a first set of experiments several nucleic acid molecules could be identified which indeed were known to be involved in autosomal recessive retinitis pigmentosa (ARRP), which inter alia is characterized by the degeneration of retinal photoreceptor cells. For example, nucleic acid molecules could be indentified corresponding to the gene encoding the human cyclic nucleotide gated channel alpha 1 (CNGA1, accession No. NM_000087; SEQ ID NO: 1 and 2). Mutations in this gene have been described to be involved in autosomal recessive retinitis pigmentosa; see Dryja et al., Proc. Nat. Acad. Sci. USA 92 (1995), 10177-10181. In another experiment, nucleic acid molecules corresponding to the human gene encoding the beta-subunit of rod cGMP phosphodiesterase (accession No. NM 000283; SEQ ID NO: 3 and 4) have been identified. Malfunction of this gene has also been associated with autosomal recessive retinitis pigmentosa, in particular with congenital stationary night blindness 3, CSNB3. These results confirm that the method of the present invention works.

In another embodiment the nucleic acid molecule specifically hybridizes to one of the nucleic acid molecules described above wherein the latter encodes a mutated version of the protein which has lost its capability of inducing a responsive change in a phenotype. In addition or alternatively, nucleic acid molecules are encompassed of at least 15 nucleotides in length and able to hybridize specifically to a nucleic acid molecule described above or with a complementary strand thereof. These nucleic acid molecules are particularly useful as probes; see infra.

The nucleic acid molecules described above can be contained in a vector and preferably be operatively linked to regulatory elements permitting expression in prokaryotic or eukaryotic host cells. Expression of said nucleic acid molecule comprises transcription into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

Possible regulatory elements permitting expression in prokaryotic host cells comprise, e.g., the $P_L$, lac, trp or tac promoter in *E. coli*, and examples for regulatory elements permitting expression in eukaryotic host cells are the AOX1 or GALL promoter in yeast or the CMV-, SV40-, RSV-promoter, CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the nucleic acid molecule. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the protein so produced.

Furthermore, the present invention relates to vectors, particularly plasmids, cosmids, viruses and bacteriophages used conventionally in genetic engineering that comprise a nucleic acid molecule of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells. The vectors containing the nucleic acid molecules of the invention can be transferred into the host cell by well known methods, which vary depending on the type of cellular host. For example, calcium chloride transfection is commonly utilized for prokaryotic cells, whereas calcium phosphate treatment or electroporation may be used for other cellular hosts; see Sambrook, supra.

Vectors that can be used for therapeutic and/or diagnostic purposes in accordance with the teaching of the present invention are known to the person skilled in the art; see, e.g., heritable and inducible genetic interference by double-stranded RNA encoded by transgenes described in Tavemarakis et al., Nat. Genet. 24 (2000), 180-183. Further vectors and methods for gene transfer and generation of transgenic animals are described in the prior art; see, e.g., adeno-associated virus related vectors described in Qing et al., Virol. 77 (2003), 2741-2746; human immunodeficiency virus type 2 (HIV-2) vector-mediated in vivo gene transfer into adult rabbit retina described in Cheng et al. Curr. Eye Res. 24 (2002), 196-201, long-term transgene expression in the RPE after gene transfer with a high-capacity adenoviral vector described in Kreppel et al., Invest. Ophthalmol. Vis. Sci. 43 (2002), 1965-1970 and non-invasive observation of repeated adenoviral GFP gene delivery to the anterior segment of the monkey eye in vivo described in Borras et al., J. Gene Med. 3 (2001), 437-449.

CNS gene transfer has also been described in Leone et al., Curr. Opin. Mol. Ther. 1 (1999), 487-492

Said vector in turn can be contained in a host cell. A bacterial, fungal, plant or animal cell can be used as a host but mammalian cells are preferred, especially RPE or neurosensory retina cells.

If these host cells are cultured under conditions allowing the expression of the polypeptide and recovering the produced polypeptide from the culture this constitutes a method for the production of a polypeptide capable of inducing a responsive change in a phenotype. Polypeptides encoded by a nucleic acid molecule as defined above or obtainable by this method are therefore preferred embodiments of this invention as well as antibodies specifically recognizing such a polypeptide. Antibodies or fragments thereof to the aforementioned polypeptides can be obtained by using methods which are described, e.g., in Harlow and Lane "Antibodies, A Laboratory Manual", CSH Press, Cold Spring Harbor, 1988.

Furthermore, the polypeptides encoded by the identified and isolated nucleic acid molecules can be used to identify synthetic chemical peptide mimetics that bind to or can function as a ligand, substrate, binding partner or the receptor of the polypeptide as effectively as does (e.g.) the natural ligand; see, e.g., Engleman, J. Clin. Invest. 99 (1997), 2284-2292. For example, folding simulations and computer redesign of structural motifs of the polypeptide can be performed using appropriate computer programs (Olszewski, Proteins 25 (1996), 286-299; Hoffman, Comput. Appl. Biosci. 11 (1995), 675-679). Computer modeling of protein folding can be used for the conformational and energetic analysis of detailed peptide and protein models (Monge, J. Mol. Biol. 247 (1995), 995-1012; Renouf, Adv. Exp. Med. Biol. 376 (1995), 3745). In particular, the appropriate programs can be used for the identification of interactive sites of the polypeptide and its ligand or other interacting proteins by computer assistant searches for complementary peptide sequences (Fassina, Immunomethods 5 (1994), 114-120. Further appropriate computer systems for the design of protein and peptides are described in the prior art, for example in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. Methods for the generation and use of peptidomimetic combinatorial libraries are described in the prior art, for example in Ostresh, Methods in Enzymology 267 (1996), 220-234 and Domer, Bioorg. Med. Chem. 4 (1996), 709-715. Furthermore, a three-dimensional and/or crystallographic structure of the polypeptide can be used for the design of mimetic inhibitors of the biological activity of the protein of the invention (Rose, Biochemistry 35 (1996), 12933-12944; Rutenber, Bioorg. Med. Chem. 4 (1996), 1545-1558).

The structure-based design and synthesis of low-molecular-weight synthetic molecules that mimic the activity of a native biological polypeptide is further described in, e.g., Dowd, Nature Biotechnol. 16 (1998), 190-195; Kieber-Emmons, Current Opinion Biotechnol. 8 (1997), 435-441; Moore, Proc. West Pharmacol. Soc. 40 (1997), 115-119; Mathews, Proc. West Pharmacol. Soc. 40 (1997), 121-125; Mukhija, European J. Biochem. 254 (1998), 433-438.

The nucleic acid molecules identified and isolated by the method of the present invention can also serve as a target for activators and inhibitors. Activators may comprise, for example, proteins that bind to the mRNA of the corresponding gene, thereby stabilizing the native conformation of the mRNA and facilitating transcription and/or translation, e.g., in like manner as Tat protein acts on HIV-RNA. Furthermore, methods are described in the literature for identifying nucleic acid molecules such as an RNA fragment that mimics the structure of a defined or undefined target RNA molecule to which a compound binds inside of a cell resulting in retardation of cell growth or cell death; see, e.g., WO 98/18947 and references cited therein. These nucleic acid molecules can be used for identifying unknown compounds of pharmaceutical and/or agricultural interest, and for identifying unknown RNA targets for use in treating a disease. Alternatively, for example, the conformational structure of the RNA fragment which mimics the binding site can be employed in rational drug design to modify known ligands to make them bind more avidly to the target. One such methodology is nuclear magnetic resonance (NMR), which is useful to identify drug and RNA conformational structures. Still other methods are, for example, the drug design methods as described in WO 95/35367, U.S. Pat. No. 5,322,933, where the crystal structure of the RNA fragment can be deduced and computer programs are utilized to design novel binding compounds which can act as antibiotics.

Hence, the antagonist/inhibitor can be, for example, an antibody, an antisense nucleic acid molecule or a ligand binding molecule. Preferably, said antagonist/inhibitor interferes with change of conformation/function of the polypeptide, most preferably with a biological activity related to angiogenesis and/or neovascularization.

The antibodies, nucleic acid molecules, inhibitors and activators used in the compositions of the present invention preferably have a specificity at least substantially identical to the binding specificity of the natural ligand or binding partner of the protein, in particular if stimulation is desired. An antibody or inhibitor can have a binding affinity to the protein of at least $10^5$ $M^{-1}$, preferably higher than $10^7$ $M^{-1}$ and advantageously up to $10^{10}$ $M^{-1}$ in case suppression should be mediated. In a preferred embodiment, a suppressive antibody or inhibitor has an affinity of at least about $10^{-7}$ M, preferably at least about $10^{-9}$ M and most preferably at least about $10^{-11}$ M; and an activator has an affinity of less than about $10^{-7}$ M, preferably less than about $10^{-6}$ M and most preferably in order of $10^{-5}$M.

In case of antisense nucleic acid molecules it is preferred that they have a binding affinity to those encoding the protein of at most 2-, 5- or 10-fold less than an exact complement of 20 consecutive nucleotides of the coding sequence.

Another embodiment of this invention is a pharmaceutical composition comprising a nucleic acid molecule described above, a vector, a host cell, a polypeptide and/or an antibody as defined above, and optionally a pharmaceutically acceptable carrier; see supra and infra Those compositions can be used in a method for treating of a disorder of the CNS or the eye comprising administering to the subject such a pharmaceutical compositions in an effective dose.

Similarly the nucleic acid molecule, vector, host cell, polypeptide and/or antibody described above can be used in a diagnostic composition that optionally contains suitable means for detection as well. Expression of a gene involved in a disorder of the CNS or the eye can be detected by obtaining mRNA from a cell; incubating the mRNA so obtained with a probe comprising a nucleic acid molecule as described above or a fragment thereof under hybridizing conditions; and detecting the presence of mRNA hybridized to the probe. On the protein level the method for detecting expression of a gene involves obtaining a cell sample from the subject; contacting the cell sample so obtained with an antibody as defined above; and detecting the presence of antibody so bound. This way the detection of the expression of a protein encoded by a mutated nucleic acid molecule which has lost its capability to induce a responsive change in phenotype is also possible.

The invention also provides a method for diagnosing in a subject a disorder or a predisposition to such disorder of the CNS or the eye which comprises:

(a) isolating DNA from patient suffering from the disorder;
(b) digesting the isolated DNA of step (a) with at least one restriction enzyme;
(c) electrophoretically separating the resulting DNA fragments on a sizing gel;
(d) incubating the resulting gel with a probe comprising a nucleic acid molecule described above or a fragment thereof labeled with a detectable marker;

(e) detecting labeled bands on a gel which have hybridized to the probe as defined to create a band pattern specific to the DNA of patients of the disorder;

(f) preparing subject's DNA by steps (a) to (e) to produce detectable labeled bands on a gel; and (g) comparing the band pattern specific to the DNA of patients of the disorder of step (e) and the subject's DNA of step (f) to determine whether the patterns are the same or different and to diagnose thereby the disorder or a predisposition to the disorder, if the patterns are the same.

Another method provided by this invention for diagnosing in a subject a disorder or a predisposition to such disorder of the CNS or the eye comprises:

(a) analyzing a sample of nucleic acids of a subject by means of a diagnostic chip, primer extension, single nucleotide polymorphisms or sequencing comprising a nucleic acid molecule as defined above, and (b) comparing the result with that of a sample obtained from a patient suffering from the disorder, wherein the identity of expression profile and/or nucleotide sequence is indicative for the disorder.

In these embodiments, the nucleic acid molecules, (poly) peptide, antibodies or compounds identified above are preferably detectably labeled. A variety of techniques are available for labeling biomolecules, are well known to the person skilled in the art and are considered to be within the scope of the present invention. Such techniques are, e.g., described in Tijssen, "Practice and theory of enzyme immuno assays", Burden, R H and von Knippenburg (Eds), Volume 15 (1985), "Basic methods in molecular biology"; Davis L G, Dibmer M D; Battey Elsevier (1990), Mayer et al., (Eds) "Immunochemical methods in cell and molecular biology" Academic Press, London (1987), or in the series "Methods in Enzymology", Academic Press, Inc. There are many different labels and methods of labeling known to those of ordinary skill in the art. Commonly used labels comprise, inter alia, fluorochromes (like fluorescein, rhodamine, Texas Red, etc.), enzymes (like horse radish peroxidase, β-galactosidase, alkaline phosphatase), radioactive isotopes (like $^{32}P$ or $^{125}I$, biotin, digoxygenin, colloidal metals, chemi- or bioluminescent compounds (like dioxetanes, luminol or acridiniums). Labeling procedures, like covalent coupling of enzymes or biotinyl groups, iodinations, phosphorylations, biotinylations, random priming, nick-translations, tailing (using terminal transferases) are well known in the art. Detection methods comprise, but are not limited to, autoradiography, fluorescence microscopy, direct and indirect enzymatic reactions, etc.

In addition, the above-described compounds etc. may be attached to a solid phase. Solid phases are known to those in the art and may comprise polystyrene beads, latex beads, magnetic beads, colloid metal particles, glass and/or silicon chips and surfaces, nitrocellulose strips, membranes, sheets, animal red blood cells, or red blood cell ghosts, duracytes and the walls of wells of a reaction tray, plastic tubes or other test tubes. Suitable methods of immobilizing nucleic acids, (poly) peptides, proteins, antibodies, etc. on solid phases include but are not limited to ionic, hydrophobic, covalent interactions and the like. The solid phase can retain one or more additional receptor(s) which has/have the ability to attract and immobilize the region as defined above. This receptor can comprise a charged substance that is oppositely charged with respect to the reagent itself or to a charged substance conjugated to the capture reagent or the receptor can be any specific binding partner which is immobilized upon (attached to) the solid phase and which is able to immobilize the reagent as defined above.

Commonly used detection assays can comprise radioisotopic or non-radioisotopic methods. These comprise, inter alia, RIA (Radioisotopic Assay) and IRMA (Immune Radioimmunometric Assay), EIA (Enzym Immuno Assay), ELISA (Enzyme Linked Immuno Assay), FIA (Fluorescent Immuno Assay), and CLIA (Chemioluminescent Immune Assay). Other detection methods that are used in the art are those that do not utilize tracer molecules. One prototype of these methods is the agglutination assay, based on the property of a given molecule to bridge at least two particles.

For diagnosis and quantification of (poly)peptides, polynucleotides, etc. in clinical and/or scientific specimens, a variety of immunological methods, as described above as well as molecular biological methods, like nucleic acid hybridization assays, PCR assays or DNA Enzyme Immunoassays (Mantero et al., Clinical Chemistry 37 (1991), 422-429) have been developed and are well known in the art. In this context, it should be noted that the nucleic acid molecules may also comprise PNAs, modified DNA analogs containing amide backbone linkages. Such PNAs are useful, inter alia, as probes for DNA/RNA hybridization.

The above-described compositions may be used for methods for detecting expression of a target gene by detecting the presence of mRNA coding for a (poly)peptide which comprises, for example, obtaining mRNA from cells of a subject and contacting the mRNA so obtained with a probe/primer comprising a nucleic acid molecule capable of specifically hybridizing with the target gene under suitable hybridization conditions, and detecting the presence of mRNA hybridized to the probe/primer. Further diagnostic methods leading to the detection of nucleic acid molecules in a sample comprise, e.g., polymerase chain reaction (PCR), ligase chain reaction (LCR), Southern blotting in combination with nucleic acid hybridization, comparative genome hybridization (CGH) or representative difference analysis (RDA). These methods for assaying for the presence of nucleic acid molecules are known in the art and can be carried out without any undue experimentation.

Furthermore, the invention comprises methods of detecting the presence of a target gene product, i.e. a protein in a sample, for example, a cell sample, which comprises obtaining a cell sample from a subject, contacting said sample with one of the aforementioned antibodies under conditions permitting binding of the antibody to the protein, and detecting the presence of the antibody so bound, for example, using immuno assay techniques such as radioimmunoassay or enzymeimmunoassay. Furthermore, one skilled in the art may specifically detect and distinguish polypeptides which are functional target proteins from mutated forms which have lost or altered their activity by using an antibody which either specifically recognizes a (poly)peptide which has native activity but does not recognize an inactive form thereof or which specifically recognizes an inactive form but not the corresponding polypeptide having native activity.

The invention also encompasses a method for diagnosing in a subject a predisposition to a CNS and/or eye disorder associated with the expression of a target gene allele; see supra. The detectable markers of the present invention may be labeled with commonly employed radioactive labels, such as, for example, $^{32}P$ and $^{35}S$, although other labels such as biotin or mercury as well as those described above may be employed as well. Various methods well-known to the person skilled in the art may be used to label the detectable markers. For example, DNA sequences and RNA sequences may be labeled with $^{32}P$ or $^{35}S$ using the random primer method. Once a suitable detectable marker has been obtained, various methods well-known to the person skilled in the art may be employed for contacting the detectable marker with the sample of interest. For example, DNA-DNA, RNA-RNA and DNA-RNA hybridizations may be performed using standard procedures. Various methods for the detection of nucleic acids are well-known in the art, e.g., Southern and northern blotting, PCR, primer extension and the like. Suitable further DNA amplification techniques are known in the art and comprise, inter alia, Ligase Chain reaction, Strand Displacement Amplification, Nucleic Acid Sequence based Amplification (NASBA), or Q-beta replicase.

Furthermore, the mRNA, cRNA, cDNA or genomic DNA obtained from the subject may be sequenced to identify mutations which may be characteristic fingerprints of target gene mutations in CNS and/or eye disorders such as described above associated with the expression of the target gene or mutated versions thereof. The present invention further, comprises methods, wherein such a fingerprint may be generated by RFLPs or AFLP of DNA or RNA obtained from the subject, optionally the DNA or RNA may be amplified prior to analysis, the methods of which are well known in the art. RNA fingerprints may be performed by, for example, digesting an RNA sample obtained from the subject with a suitable RNA-Enzyme, for example RNase $T_1$, RNase $T_2$ or the like or a ribozyme and, for example, electrophoretically separating and detecting the RNA fragments on PAGE as described above. Preferably, hybridization (and subsequent washing) is effected under stringent conditions; see, e.g., Sambrook et al., loc. cit and supra Furthermore, the present invention relates to a method as described above wherein said sample is or is derived from hair, blood, serum, sputum, feces or another body fluid. The sample to be analyzed may be treated such as to extract, inter alia, nucleic acid molecules, (poly)peptides, or antibodies.

The present invention also relates to kit compositions containing specific reagents such as those described herein-before. Kits containing oligonucleotides, DNA or RNA, antibodies or protein may be prepared. Such kits are used to detect for example DNA which hybridizes to DNA of the target gene or to detect the presence of protein or peptide fragments in a sample. Such characterization is useful for a variety of purposes including but not limited to forensic analyses, diagnostic applications, and epidemiological studies in accordance with the above-described methods of the present invention. The recombinant target proteins, DNA molecules, RNA molecules and antibodies lend themselves to the formulation of kits suitable for the detection and typing of the target gene. Such a kit would typically comprise a compartmentalized carrier suitable to hold in close confinement at least one container. The carrier would further comprise reagents such as recombinant protein or antibodies suitable for detecting the expression or activity of the target gene or gene product. The carrier may also contain a means for detection such as labeled antigen or enzyme substrates or the like.

Another embodiment of this invention comprises the use of an effective dose of a nucleic acid molecule described above or a nucleic acid molecule which is complementary to such a nucleic acid molecule, or a vector as defined previously for the preparation of a composition for treating, preventing and/or delaying a disorder of the CNS and/or the eye in a subject by somatic gene therapy.

As used herein, the term "effective dose" means the total amount of the drug or pro-drug that is sufficient to show a meaningful patient benefit, i.e., treatment, healing, prevention or amelioration of a condition related to the disorder of the CNS, for example neovascularization, or an increase in rate of treatment, healing, prevention or amelioration of such conditions. In addition or alternatively, in particular with respect to pre-clinical testing of the drug the term "effective dose" includes the total amount of the drug or pro-drug that is sufficient to elicit a physiological response in a non-human animal test.

As mentioned above, the vectors of the present invention may also be an expression, a gene transfer or gene targeting vector. Gene therapy, which is based on introducing therapeutic genes into cells by ex-vivo or in-vivo techniques is one of the most important applications of gene transfer. Transgenic mice expressing a neutralizing antibody directed against nerve growth factor have been generated using the "neuroantibody" technique; Capsoni, Proc. Natl. Acad. Sci. USA 97 (2000), 6826-6831 and Biocca, Embo J. 9 (1990), 101-108. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94/29469; WO 97/00957; U.S. Pat. No. 5,580,859; U.S. Pat. No. 5,589,466; U.S. Pat. No. 4,394,448 or Schaper, Current Opinion in Biotechnology 7 (1996), 635-640, and references cited therein. In particular, said vectors and/or gene delivery systems are also described in gene therapy approaches in neurological tissue/cells (see, inter alia Blömer, J. Virology 71 (1997) 6641-6649) or in the hypothalamus (see, inter alia, Geddes, Front Neuroendocrinol. 20 (1999), 296-316 or Geddes, Nat. Med. 3 (1997), 1402-1404). Further suitable gene therapy constructs for use in neurological cells/tissues are known in the art, for example in Meier (1999), J. Neuropathol. Exp. Neurol. 58, 1099-1110. The nucleic acid molecules and vectors of the invention may be designed for direct introduction or for introduction via liposomes, viral vectors (e.g. adenoviral, retroviral), electroporation, ballistic (e.g. gene gun) or other delivery systems into the cell. The introduction and gene therapeutic approach should, preferably, lead to the expression of a functional copy of the target gene of the invention. On the other hand, if target gene expression should be reduced, the expression of the introduced vector preferably leads to the production of an inhibitor as described above, for example antisense RNA or RNAi molecules. In those embodiments, the nucleic acid molecules are preferably linked to cell and/or tissue specific promoters, particularly preferred to promoters directing the expression in the cells and tissue of the eye. Examples for suitable promoters include the angiopoietin 2 promotor (see in Hackett, J. Cell. Physiol. 184 (2000), 275-284) and particularly preferred promotors which are capable of targeting expression to the retinal pigment epithelium such as the tyrosinase related protein-1 (Tyrp1) promoter; see Beermann, Cell Mol. Biol. 45 (1999), 961-968.

In a further aspect, the present invention also provides a method for the screening for compounds modulating the expression or the activity of a polypeptide involved in a disorder of the CNS or the eye. This method involves contacting a cell which expresses a polypeptide as described above identified by the methods illustrated previously with a compound to be screened and determining if the expression or the activity is altered.

The amount of time necessary for cellular contact with the compound is empirically determined, for example, by running a time course with a known modulator and measuring cellular changes as a function of time. The measurement means of the method of the present invention can be further defined by comparing a cell that has been exposed to a compound to an identical cell that has not been similarly expose to the compound. Alternatively two cells, one containing a functional target gene and a second cell identical to the first, but lacking a functional target gene could be both be contacted with the same compound and compared for differences between the two cells. This technique is also useful in establishing the background noise of these assays. One of average skill in the art will appreciate that these control mechanisms also allow easy selection of cellular changes that are responsive to modulation of the functional target gene or gene product.

The term "cell" refers to at least one cell, but includes a plurality of cells appropriate for the sensitivity of the detection method. Cells suitable for the present invention may be bacterial, yeast, or preferably eukaryotic. The methods of this invention employ certain types of cells, certain observations of changes in aspects of the biological state of a cell, and certain comparisons of these observed changes. Preferred cell lines to be used in the assays of the present invention, especially cells and cell lines derived from the CNS or eye of, for example human, porcine, or murine origin, are described in the examples and in the prior art, for example human retinal pigment epithelial cells (see e.g. Dunaief et al. Curr. Eye Res. 24 (2002), 392-396), immortalized human corneal epithelial cell line (see e.g. Athmanathan et al., BMC Ophthalmol. 30 (2002), 3), and also cells of the CNS, for example human neuronal cell lines (see e.g. Li et al., J. Neurosci. Res. 71 (2003), 559-566), CNS cell line immortalized with an N-terminal fragment of SV40 large T (see e.g. Truckenmiller et al., Exp. Neurol. 175 (2002), 318-337), immortalized Z310 choroidal epithelial cell line from murine choroid plexus (see Zheng and Zhao, Brain Res. 958 (2002), 371-380.

Suitable cell lines, in particular animal and human cell lines as well as technical information on the characteristics of cell lines, cytogenetic analysis, suggestions for handling cell cultures, etc can be obtained from depository institutions, for example the American Type Culture Collection (ATCC), P.O. Box 1549, Manassas, Va. 20108, USA and DSMZ—Deutsche Sammlung von Mikroorganismen und Zellkulturen GmbH, Mascheroder Weg 1b, 38124 Braunschweig, GERMANY. Preferred are RPE cells or RPE derived cell lines such as ARPE-19, cells overexpressing or with inhibited expression of candidate genes involved in CNS or eye disorders or host cells as described previously.

In a preferred embodiment said polypeptide is expressed under the control of the GGTB-promoter, which is described in van Bokhoven et al., Genomics 38 (1996), 133-140. The test substance can be a single chemotherapeutic agent or a mixture of chemotherapeutic agents.

The cell that is contacted with the test substance can be derived from a single cell or a multi-cellular organism. Said multi-cellular organism can be selected from the group consisting of a vertebrate animal, a mammal, a primate, an invertebrate animal, an insect and a plant. The above-described cells can also be comprised in a tissue or organism, i.e. non-human animal. General methods for the screening of compounds that have a desired effect on a cell or organism as measured in a specific assay are described in the prior art; see for example U.S. Pat. No. 6,165,709 and references cited herein.

Cells, non-human animals and target gene expression and/or knock out systems can be found in the prior art and adapted for the method of the present invention; see for example the documents cited herein.

The cellular changes suitable for the method of the present invention comprise directly measuring changes in the function or quantity of the target gene product, or by measuring downstream effects, for example by measuring secondary messenger concentrations or changes in transcription or by changes in protein levels of genes that are transcriptionally influenced by the target gene product, or by measuring phenotypic changes in the cell. Preferred measurement means include changes in the quantity of protein, changes in the functional activity, changes in the quantity of mRNA, changes in intracellular protein, changes in cell surface protein, or secreted protein, or changes in $Ca^{2+}$, cAMP or GTP concentration. Changes in the quantity or functional activity of target gene products are described herein. Changes in the levels of mRNA are detected by reverse transcription polymerase chain reaction (RT-PCR), by differential gene expression or by microarrays. Immunoaffinity, ligand affinity, or enzymatic measurement quantities changes in levels of protein in host cells. Protein-specific affinity beads or specific antibodies are used to isolate for example $^{35}$S-methionine labeled or unlabelled protein. Labeled protein is analyzed by SDS-PAGE. Unlabelled protein is detected by Western blotting, cell surface detection by fluorescent cell sorting, cell image analysis, ELISA or RIA employing specific antibodies. Where the protein is an enzyme, the induction of protein is monitored by cleavage of a flourogenic or colorimetric substrate.

Where the endogenous gene encodes a soluble intracellular protein, changes in the endogenous gene may be measured by changes of the specific protein contained within the cell lysate. The soluble protein may be measured by the methods described herein.

The assays may be simple "yes/no" assays to determine whether there is a change in expression or function, or may comprise any one of the above described methods, for example for the detection of angiogenic activity. The assay may be made quantitative by comparing the expression or function of a test sample with the levels of expression or function in a standard sample. Modulators identified in this process are useful as therapeutic agents.

The above-described methods can, of course, be combined with one or more steps of any of the above-described screening methods or other screening methods well known in the art. Methods for clinical compound discovery comprises for example ultrahigh-throughput screening (Sundberg, Curr. Opin. Biotechnol. 11 (2000), 47-53) for lead identification, and structure-based drug design (Verlinde and Hol, Structure 2 (1994), 577-587) and combinatorial chemistry (Salemme et al., Structure 15 (1997), 319-324) for lead optimization.

Once a drug has been selected, the method can have the additional step of repeating the method used to perform rational drug design using the modified drug and to assess whether said modified drug displays better affinity according to for example interaction/energy analysis.

In a preferred embodiment of the method of the present invention, said cell, tissue or non-human animal is a transgenic cell, tissue or non-human animal which displays a substantially reduced or enhanced level of target gene expression and/or gene product activity compared to a corresponding wild-type animal. Usually, said transgenic non-human animal displaying a reduced level of target gene activity comprises at least one mutant allele of the target gene or a corresponding trans-dominant allele of a different gene. Preferably, said transgenic non-human animal is a knock-out animal.

Preferably said substantially reduced or enhanced level of target gene expression and/or gene product activity results in an altered and a phenotypic response of the transgenic cell, tissue or non-human animal. An agonist/activator or antagonist/inhibitor will then be identified by observing whether a candidate compound is able at a certain concentration to revert the phenotypic response of said transgenic cell, tissue or non-human animal back to normal. In a particular preferred embodiment, said transgenic non-human animal displays a CNS and/or eye disorder as defined above.

The assay methods of the present invention can be in conventional laboratory format or adapted for high throughput. The term "high throughput" (HTS) refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include 96-well, 384-well or more-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

The test substances which can be tested and identified according to a method of the invention may be expression libraries, e.g., cDNA expression libraries, peptides, proteins, nucleic acids, antibodies, small organic compounds, hormones, peptidomimetics, PNAs, aptamers or the like (Milner, Nature Medicine 1 (1995), 879-880; Hupp, Cell 83 (1995), 237-245; Gibbs, Cell 79 (1994), 193-198 and references cited supra). The test substances to be tested also can be so called "fast seconds" of known drugs. The invention also relates to further contacting the test cells with a second test substance or mixture of test substances in the presence of the first test substance.

In the method of the invention, said cells are preferably contained in a container, for example in a well in a microtiter plate, which may be a 24, 96, 384 or 1586 well plate. Alternatively, the cells can be introduced into a microfluidics device, such as those provided by Caliper (Newton, Mass., USA). In another preferred embodiment, step (b) of the method of the present invention comprises taking 2, 3, 4, 5, 7, 10 or more measurements, optionally at different positions within the container. In some embodiments of the method of the present invention, a compound known to activate or inhibit the target gene or gene product is added to the medium prior to step (b).

Preferably, in a first screen said test substance is comprised in and subjected as a collection of compounds. Said collection of compounds may have a diversity of about $10^3$ to about $10^5$. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Drug discovery by dynamic combinatorial libraries is described, for example, in Nat. Rev. Drug Discov. 1 (2002), 26-36 and Drug Discov. Today 7 (2002), 117-125.

Furthermore, the above-described methods can, of course, be combined with one or more steps of any of the above-described screening methods or other screening methods well known in the art. Methods for clinical compound discovery comprises for example ultrahigh-throughput screening (Sundberg, Curr. Opin. Biotechnol. 11 (2000), 47-53) for lead identification, and structure-based drug design (Verlinde and Hol, Structure 2 (1994), 577-) 587) and combinatorial chemistry (Salemme et al., Structure 15 (1997), 319-324) for lead optimization. Once a drug has been selected, the method can have the additional step of repeating the method used to perform rational drug design using the modified drug and to assess whether said modified drug displays better affinity according to for example interaction/energy analysis. The method of the present invention may be repeated one or more times such that the diversity of said collection of compounds is successively reduced. Preferably, the target polypeptide is involved in angiogenesis or neovascularization.

As mentioned above, the present invention provides convenient assays, preferably cell based and in vivo assays for identifying and obtaining drugs capable of modulating the gene activity, thereby being useful as a therapeutic agent for the treatment of diseases related to CNS disorders including (e.g.) Schizophrenia, Parkinson's Disease, Alzheimer's Disease, and eye diseases such as those described above. In accordance with this, the present invention provides also a use for compounds which have been known in the art, properly also known to be able to modulate target gene activity but which hitherto have not been suggested for medical use because of the lack of knowledge of phenotypic responses of an organism evoked by target gene activity or the lack of it.

One embodiment of this invention comprises a method for the production of a drug or prodrug identified by such a screening as a modulator or a derivative thereof, particularly if the substance has hitherto not been known as a drug for the treatment of a disorder of the CNS or the eye.

Substances are metabolized after their in vivo administration in order to be eliminated either by excretion or by metabolism to one or more active or inactive metabolites (Meyer, J. Pharmacokinet. Biopharm. 24 (1996), 449-459). Thus, rather than using the actual compound or drug identified and obtained in accordance with the methods of the present invention a corresponding formulation as a pro-drug can be used which is converted into its active form in the patient by his/her metabolism. Precautionary measures that may be taken for the application of pro-drugs and drugs are described in the literature; see, for review, Ozama, J. Toxicol. Sci. 21(1996), 323-329.

Furthermore, the present invention relates to the use of a compound identified, isolated and/or produced by any of these methods for the preparation of a composition for the treatment of said CNS and eye disorders. As a method for treatment the identified substance or the composition containing it can be administered to a subject suffering from such a disorder. Compounds identified, isolated and/or produced by the method described above can also be used as lead compounds in drug discovery and preparation of drugs or prodrugs.

This usually involves modifying the lead compound or a derivative thereof or an isolated compound as a to achieve (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmakinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carbon acids, or (iii) esterification of hydroxyl groups to, e.g. phosphates, pyrophosphates or sulfates or hemi succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiff s bases, oximes, acetales, ketales, enolesters, oxazolidines, thiozolidines or combinations thereof; and (b) formulating the product of said modification with a pharmaceutically acceptable carrier.

The various steps recited above are generally known in the art. For example, computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, peptidomimetics and/or computer aided design of appropriate derivatives and analogues can be used, for example, according to the methods described above. Methods for the lead generation in drug discovery also include using proteins and detection methods such as mass spectrometry (Cheng et al. J. Am. Chem. Soc. 117 (1995), 8859-8860) and some nuclear magnetic resonance (NMR) methods (Fejzo et al., Chem. Biol. 6 (1999), 755-769; Lin et al., J. Org. Chem. 62 (1997), 8930-8931). They may also include or rely on quantitative structure-action relationship (QSAR) analyses (Kubinyi, J. Med. Chem. 41 (1993), 2553-2564, Kubinyi, Pharm. Unserer Zeit 23 (1994), 281-290) combinatorial biochemistry, classical chemistry and others (see, for example, Holzgrabe and Bechtold, Pharm. Acta Helv. 74 (2000), 149-155). Furthermore, examples of carriers and methods of formulation may be found in Remington's Pharmaceutical Sciences.

Once a drug has been selected in accordance with any one of the above-described methods of the present invention, the drug or a pro-drug thereof can be synthesized in a therapeutically effective amount. As used herein, the term "therapeutically effective amount" means the total amount of the drug or pro-drug that is sufficient to show a meaningful patient benefit, i.e., treatment, healing, prevention or amelioration of a condition related to disorders of the CNS and/or the eye, or an increase in rate of treatment, healing, prevention or amelioration of such conditions. In addition or alternatively, in particular with respect to pre-clinical testing of the drug the term "therapeutically effective amount" includes the total amount of the drug or pro-drug that is sufficient to elicit a physiological response in a non-human animal test.

Furthermore the nucleic acid molecules described above can in turn be used for the validation of test substances, lead compounds, drugs and prodrugs for the treatment of a disorder of the CNS or the eye or for the identification and isolation of downstream genes.

The present invention also relates to a chip or array comprising a solid support and attached thereto one or more of the nucleic acid molecules or encoded (poly)peptides described above, which chip or assay is useful for performing any one of the above described methods. Chip-based or other means for the detection of expression and/or activity of a nucleic acid molecule described above or the respective polypeptides can be provided for in form of a kit, which constitutes a preferred embodiment of the invention. Similarly kit can be developed for the methods for identification, production and screening of active molecules.

In a still further embodiment, the present invention relates to a transgenic non-human animal which displays an aberrant expression or activity of the target gene and/or gene product mentioned previously or identified and obtained by the methods described above, especially when said animal reproduces a disorder of the CNS and/or the eye. Preferably, said animal is a mammal.

A method for the production of a transgenic non-human animal, which is also encompassed by the present invention, for example transgenic mouse, comprises introduction of a polynucleotide or targeting vector encoding said polypeptide into a germ cell, an embryonic cell, stem cell or an egg or a cell derived therefrom. The non-human animal can be used in accordance with a screening method of the invention described herein. Production of transgenic embryos and screening of those can be performed, e.g., as described by A. L. Joyner Ed., Gene Targeting, A Practical Approach (1993), Oxford University Press. A general method for making transgenic non-human animals is described in the art, see for example WO 94/24274. For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62: 1073-1085 (1990)) essentially as described (Robertson, E. J. (1987) in Teratocarcinomas and Embryonic Stem Cells: A Practical Approach. E. J. Robertson, ed. (Oxford: IRL Press), p. 71-112) may be used for homologous gene targeting. Other suitable ES lines include, but are not limited to, the E14 line (Hooper et al., Nature 326: 292-295 (1987)), the D3 line (Doetschman et al., J. Embryol. Exp. Morph. 87: 27-45 (1985)), the CCE line (Robertson et al., Nature 323: 445-448 (1986)), the AK-7 line (Zhuang et al., Cell 77: 875-884 (1994)). The success of generating a mouse line from ES cells bearing a specific targeted mutation depends on the pluripotence of the ES cells (i.e., their ability, once injected into a host developing embryo, such as a blastocyst or morula, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having either the recombinase or reporter loci and are backcrossed and screened for the presence of the correctly targeted transgene (s) by PCR or Southern blot analysis on tail biopsy DNA of offspring so as to identify transgenic mice heterozygous for either the recombinase or reporter locus/loci.

Methods for producing transgenic flies, such as *Drosophila melanogaster* are also described in the art, see for example U.S. Pat. No. 4,670,388, Brand & Perrimon, Development (1993) 118: 401-415; and Phelps & Brand, Methods (April 1998) 14: 367-379. Transgenic worms such as *C. elegans* can be generated as described in Mello, et al., Embo J. 10 (1991), 3959-3970, Plasterk, Methods Cell Biol 48 (1995), 59-80.

Preferably, the transgenic non-human animal comprises at least one inactivated or suppressed wild type allele of the corresponding gene, involved in an CNS and/or eye disorder; see supra. This embodiment allows for example the study of the interaction of various mutant forms of these genes or gene products on the onset of the clinical symptoms and/or may be used to verify the involvement of said gene(s) in the disorder to be studied. All the applications that have been herein before discussed with regard to a transgenic animal also apply to animals carrying two, three or more transgenes. It might be also desirable to inactivate target gene expression or function at a certain stage of development and/or life of the transgenic animal. This can be achieved by using, for example, tissue specific (see supra), developmental and/or cell regulated and/or inducible promoters which drive the expression of, e.g., an antisense or ribozyme directed against the RNA transcript encoding the target gene mRNA; see also supra. A suitable inducible system is for example tetracycline-regulated gene expression as described, e.g., by Gossen and Bujard (Proc. Natl. Acad. Sci. 89 USA (1992), 5547-5551) and Gossen et al. (Trends Biotech. 12 (1994), 58-62). Similar, the expression of a mutant target gene may be controlled by such regulatory elements. Preferably, the presence of the transgenes in cells of the transgenic animals leads to various physiological, developmental and/or morphological changes, preferably to conditions related to disorders of the CNS and/or eye such as those described above.

In another embodiment said transgenic non-human animal is used for a process in the discovery of drugs for the treatment of a disorder of the CNS and/or the eye. In particular, mammlian animals are preferred, especially mice and rats. Corresponding animal systems that can be adapted in accordance with the present invention are known to person skilled in the art; see, e.g., molecular biological approaches to neurological disorders including knockout and transgenic mouse models described in Shibata et al., Neuropathology 22 (2002), :337-349. However, the widely used zebra fish may also be used since this model system has also been shown to provide valuable predicitve results; see, e.g. Gerlai et al., Pharmacol. Biochem. Behav. 67 (2000), 773-782.

In a preferred embodiment of the invention the pharmaceutical composition for use in the treatment of the above described CNS and/or eye disorders comprise one or more double-stranded oligoribonucleotides (dsRNA), see supra, which mediate an RNA interference of the corresponding mRNA of one or more nucleic acid molecules which have been shown to be involved in said disorders, and optionally a pharmaceutically acceptable carrier. The method for specific inhibition of genes by double-stranded oligoribonucleotides (dsRNA) is known from WO 01/75164. The disclosure of this application is hereby included in this present description.

This application describes that double-stranded oligoribonucleotides (dsRNA) induce specific degradation of mRNA after delivery to the target cells. The specificity of this process is mediated by the complementarity of one of the two dsRNA strands to the mRNA of the target gene.

The process of gene-specific, post-transcriptional switching off of genes by dsRNA molecules is referred to as RNA interference (RNAi). This term was originally developed by Fire and co-workers to describe the blockage of gene expression observed by delivery of dsRNA molecules to the threadworm *Caenorhabditis elegans* (Fire et al., 1999). Subsequently, RNAi could also be demonstrated in plants, protozoa, insects (Kasschau and Carrington 1998) and recently also in mammalian cells (Caplen et al., 2001; Elbashir et al., 2001). The mechanism by which RNAi suppresses gene expression is not yet fully understood. Studies of non-mammalian cells have shown that dsRNA molecules are transformed into small interfering RNA molecules (siRNA molecules) by endogenous ribonucleases (Bernstein et al., 2001; Grishok et al., 2001; Hamilton and Baulcombe, 1999; Knight and Bass, 2001; Zamore et al., 2000).

Desirably, the region of the double stranded RNA that is present in a double stranded conformation includes at least 5, 10, 20, 30, 50, 75, 100 or 200. Preferably, the double stranded region includes between 15 and 30 nucleotides, most preferably 20 to 25 and particularly preferred 21 to 23 nucleotides, since for the specific inhibition of a target gene, it suffices that a double-stranded oligoribonucleotide exhibits a sequence of 21 to 23 nucleotides (base pairs) in length identical to the target gene; see, e.g., Elbashir et al., Methods 26 (2002), 199-213 and Martinez et al., Cell 110 (2002), 563-574. General means and methods for cell based assays for identifying nucleic acid sequences that modulate the function of a cell, by the use of post-transcriptional gene silencing including definitions, methods for the preparation of dsRNA, vectors, selectable markers, compositions, detection means, etc., and which can be adapted in accordance with the teaching of the present invention are described in European patent application EP 1 229 134 A2, the disclosure content of which is incorporated herein by reference In contrast to the cited literature in which the use of siRNA and other RNA based molecules is described for cell culture only, experiments performed in accordance with the present invention surprisingly demonstrate that dsRNA molecules of a length of 21 to 23 nucleotides are capable of, after systemic application, for example by intravenous injection, to cross the blood-retina barrier, and specifically inactivate target genes in the tissues of the back of the eye. This overcoming the blood-retina barrier is all the more remarkable, because no experiment could demonstrate overcoming the blood-brain barrier by dsRNA so far. The methods and uses of the invention, explained below by means of examples, are thus suitable for the provision of animal models with which targets, the restricted function of which causing diseases of the eye, can be identified and validated. Those methods are moreover suitable for the specific intervention in CNS and eye diseases on a molecular level, without necessitating direct application to the site of, for example affected cells or tissue. The specificity of selected inhibitors such as preferably RNAi for the inhibition of genes expressed specifically in target cells minimizes the risk of unwanted side effects.

The dosage regimen of the pharmaceutical compositions in all of the above described methods and uses of the present invention will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 μg to 10 mg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 0.01 μg to 10 mg units per day. If the regimen is a continuous infusion, it should also be in the range of 0.01 μg to 10 mg units per kilogram of body weight per minute, respectively. Progress can be monitored by periodic assessment. Dosages will vary but a preferred dosage for intravenous administration of nucleics acids is from approximately $10^6$ to $10^{12}$ copies of the nucleic acid molecule.

Therapeutic or diagnostic compositions of the invention are administered to an individual in an effective dose sufficient to treat or diagnose disorders in which modulation of a target gene or gene product is indicated. The effective amount may vary according to a variety of factors such as the individual's condition, weight, sex and age. Other factors include the mode of administration. The pharmaceutical compositions may be provided to the individual by a variety of routes such as by intracoronary, intraperitoneal, subcutaneous, intravenous, transdermal, intrasynovial, intramuscular or oral routes. In addition, co-administration or sequential administration of other agents may be desirable.

A therapeutically effective dose refers to that amount of compounds described in accordance with the present invention needed to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

These and other embodiments are disclosed and encompassed by the description and Examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TEBTECH 12 (1994), 352-364.

The above disclosure generally describes the present invention. A more complete understanding can be obtained by reference to the following specific examples and figure which are provided herein for purposes of illustration only and are not intended to limit the scope of the invention. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature; see, for example, DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986).

Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publication, including Sambrook et al., (1989) Molecular Cloning: A Laboratory Manual, 2nd ed., Cold Spring Harbor Laboratory Press.

The Figure shows:

FIG. 1: eGFP-expression in retina and retinal pigment epithet (RPE) of systemically dsRNA-treated FVB.CG-TG (GFPU)5NAGY mice. The Figure shows eGFP-expression in eye paraffin sections of dsRNA-treated FVB.Cg-Tg(GFPU) 5Nagy mice. Expression in retina and retinal pigment epithel (RPE) of systemically dsRNA-treated FVB.CG-TG(GFPU) 5NAGY mice is highest in the buffer control, slightly decreased in mice treated with non-silencing dsRNA and clearly decreased in eGFP-specific dsRNA treated mice (buffer control >200 μg/kg BW non-silencing dsRNA >100 μg/kg BW eGFP-specific dsRNA >200 μg/kg BW eGFP-specific dsRNA).

EXAMPLES

Example 1

Isolation of Primary Porcine Retinal Pigment Epithelial Cells (RPE Cells)

The following example describes exemplary the isolation of primary porcine RPE cells which is carried out under sterile conditions. The isolation of RPE-cells from pork, human and cattle is in principal the same.

Porcine eyes were obtained from a local slaughter house. After the eyes were liberated from rests of ocular muscle, they were washed once with sterile ice cold phosphate buffered saline (1×PBS: 1.15 g/l $Na_2HPO_4$, 0.20 g/l $KH_2PO_4 \times H_2O$, 8.00 g/l NaCl, 0.20 g/l KCl, 0.10 g/l $MgCl_2$, 0.10 g/l $CaCl_2$) containing penicillin (100 U/ml) and streptomycin (100 μg/ml). The eyes were sliced around the ora serrata and the ocular lens and the vitreous were removed. From the eye cups the retinae were carefully detached with a hitch and removed after cutting the optic nerve. The retinae were used for the isolation of the rod outer segments as described in example 2. The remaining eye cup was covered with 1 ml 1×PBS to wash the cells. The solution was rejected and the cells were incubated in 1 to 1.5 ml of a trypsin/EDTA solution (0.25%/0.02%) for 15 minutes at 37° C. The solution was rejected and the cups were again covered with 1 ml of the trypsin/EDTA solution for 1 hour at 37° C. The RPE cells were carefully removed by pipetting up and down and cells from six eyes were diluted in 20 ml cell culture medium (DMEM F12 (Bio Whittaker) with 10% fetal calf serum (FCS), penicillin (100 U/ml) and streptomycin (100 μg/ml), 2 mM glutamine, 1.5 g/ml sodium bicarbonate). The cells were centrifuged 5 minutes with 120×g at room temperature and washed twice with the cell culture medium. Per T25 cell culture flask, cells according to three retinae were plated. To get rid of cell debris the cells were washed with 1×PBS on the next day. For approximately one week RPE-cells were cultivated in cell culture medium containing 10% FCS. After they have reached confluency the culture medium was substituted against medium containing 2% FCS. After a further one week-incubation the cells were splitted on cell culture dishes in the ratio 1:2 for further experimental use.

Example 2

Isolation of Rod Outer Segments (ROS) from Porcine Eyes

The ROS isolation was carried out under sterile conditions. Thirty retinae isolated during the RPE-cell preparation (see example 1) were transferred to 15 ml of a ice cold homogenisation buffer (containing 20% (w/v) sucrose, 20 mM tris-acetat pH 7.2, 2 mM $MgCl_2$, 10 mM glucose). The suspension was shaken gently for 1 minute, filtered 3 times through cheesecloth to remove tissue fragments and layered on a 24 ml 25-60% w/v continuous sucrose gradient containing 20 mM Tris acetate pH 7.2, 10 mM glucose. Centrifugation was carried out in a Beckman SW-27 rotor at 24,000 rpm for 1 hour at 4° C. The upper white-yellow band of the gradient was collected, diluted with the same volume of 10 mM Hepes buffer pH 7.4, 115 mM NaCl, 2.5 mM KCl, 1 mM DTT, 1 mM $MgCl_2$, mixed cautious and centrifuged 10 minutes in a Sigma 4K15 centrifuge, 2989×g, 4° C. The supernatant was removed carefully and the ROS pellet was stored for further use at −20° C. From one retina were approximately $1\times10^7$ ROS isolated.

Example 3

Incubation of Primary Porcine RPE-Cells with (Physiological Concentrations) of ROS Since the incubation of RPE-cells from pork, human and cattle with ROS is in principal the same, the following example refers to the incubation of RPE cells isolated from porcine eyes (see example 2).

ROS pellet stored at −20° C. was warmed-up slowly to room temperature. According to the number of primary RPE-cells, an amount of 10 to 100 ROS per cell was taken from the ROS-suspension. During incubation, the cell culture medium was changed every day and new ROS were added.

The phagocytosis of ROS by RPE cells was controlled in parallel by two approaches. Approach one comprises the detection of ROS covalently labeled with the dual wavelength fluorescent dye SNAFL-2 (Molecular Probes, Leiden Netherlands). The acid form (pH 5) appears green-yellow whereas the alkaline form (pH 9) appears yellow-orange. SNAFL-2 (10 μg SNAFL-2 in 1 μl dimethylformimide) was added to isolated ROS in 100 μl sucrose buffer (20% sucrose, 2 mM MgCl2, 10 mM glucose, 20 mM tris acetate pH 8.0) and the ROS were labeled for 1 hour at room temperature in the dark with gentle stirring. The labeled ROS were diluted with the same volume of the hepes buffer pH 8.0 spun down for 5 minutes at 2000 rpm in a Heraeus Biofuge pico and washed two times with 100 μl the hepes buffer pH 8.0. The labeled ROS were resuspended in cell culture medium and added to the cells. After an incubation time of 4 to 8 hours cells were washed and cell culture medium pH 9.0 was added for fluorescence microscopy.

In approach two ROS treated cells were washed in 1×PBS (containing $Ca^{2+}$ and $Mg^{2+}$) and analyzed by fluorescence microscopy for autofluorescence-activity of internalized ROS.

Example 4

Post Transcriptional Gene Silencing (PTGS) of a Given Target Gene

The following example describes PTGS of a given target gene (growth factor) X in primary cells isolated from different organisms (i.e. pork, human, cattle) or in cell lines (i.e. ARPE-19).

After optimizing the experimental conditions with respect to the dsRNA identity, its concentration and the appropriate transfection reagent, PTGS was performed using three (to five) dsRNAs homologous to different regions of the mRNA of the target gene synthesized either by a commercial provider (preferential Proligo) or from corresponding oligonucleotides using a commercially available kit (preferential Silencer™ siRNA Construction Kit, Ambion). 1 ng up to 100 μg of each siRNA was introduced into the cells by commercially available transfection reagents (preferential Gene Eraser/Stratagene, Transmessenger/Qiagen, Oligofectamin/Invitrogen).

Up to five days post transfection cells were harvested for the analysis of mRNA expression profile by real time PCR and up to one week post transfection cells were harvested for the analysis of protein expression by western blot analysis or ELISA.

Example 5

Synthesis and Purification of A2-E

A2-E was synthesized from all-trans-retinal and ethanolamine as described from Parish et al. (1998) (Parish C A, Hashimoto M, Nakanishi K, Dillon J, Sparrow J.: Isolation and one-step preparation of A2E and iso-A2E, fluorophores from human retinal pigment epithelium. Proc Natl Acad Sci USA. 1998 Dec. 8; 95(25):14609-13) and purified chromatographically on silica gel 60 thin layer chromatography plates using the primary developing system from Eldred and Katz (1988) (Eldred G E, Katz M L.: Fluorophores of the human retinal pigment epithelium: separation and spectral characterization. Exp Eye Res. 1988 July; 47(1):71-86). 50-150 mg retinal were dissolved in 1.5-5.5 ml ethanol. 5-15 μl ethanolamine was added and stirred. While stirring 5-15 μl acetic acid were slowly added. The mixture was wrapped in aluminum foil, and stirred for two days at room temperature. The reaction mix was distributed 4 times into four Eppendorf tubes and concentrated to dryness in a speedvac overnight. The content of two Eppendorf reaction tubes was dissolved in a total of 200-600 μl "primary developing system" (14.5 ml heptane, 8.8 ml hexane, 9.8 ml chloroform, 3 ml ether, 3 ml acetone, 14.8 ml iso-propanol, 27 ml ethanol, 2.5 ml methanol, 0.4 ml acetic acid, 7.4 ml $H_2O$). Then 5-15 aliquots, containing 20-60 μl each, of this solution were applied to a silica chromatography plate that was developed with the "primary developing system" for about 2 hours. A2-E was detected an the plates by their fluorescence upon illumination with 366-nm light. The material containing A2-E was scraped off (A2-E: upper spot; iso-A2-E: lower spot) and eluted 2-3 times with chloroform/methanol/water by vortexing. The supernatants were combined and dried in a speedvac for few hours. The dried material was taken up in 200-600 μl "primary developing system" and rechromatographed. The extraction and the drying were also repeated. The dried material was taken up as a A2-E stock solution in about 1 ml $Me_2SO$ or ethanol and stored at −20° C. in the dark. Total A2-E diluted in $Me_2SO$ or ethanol was quantified using a molar extinction coefficient of 36,900 at 439 nm (Parish C A, Hashimoto M, Nakanishi K, Dillon J, Sparrow J.: Isolation and one-step preparation of A2E and iso-A2E, fluorophores from human retinal pigment epithelium. Proc Natl Acad Sci USA. 1998 Dec. 8; 95(25):14609-13).

Example 6

Incubation of RPE Cells with A2-E and the Analysis of A2-E Accumulation

A2-E was diluted into the RPE cell culture medium to a concentration of 1 to 100 μM A2-E and 0.5% $Me_2SO$ or ethanol. With the aim to find out sub-apoptocical A2E concentrations, control incubations were done with 0.5% $Me_2SO$ or ethanol in the absence of A2-E as a negative control and with 1 to 200 μM staurosporine as a apoptosis control. Incubation was carried out at 37° C. with 5% $CO_2$ for 24 to 144 h in the darkness (wrapped in aluminum foil) once each day. Cells can also placed under a light source and exposed to light at 390 to 550 nm of various times up to 144 hours. Controls were also run with medium alone. To determine the mean autofluorescence per population of RPE the intracellular fluorescence was assessed using a fluorescence microscope (Nikon; excitation 450-490 nm, emission >510 nm) and a Safire (Tecan; excitation 456 nm, emission 610 nm) at various times after feeding.

Example 7

Apoptosis Assay

The following example describes the analysis of the induction of apoptosis with the Cell Death Detection ELISA Plus (Roche) (Wyllie A H, Kerr J F, Currie A R.: Cell death: the significance of apoptosis. Int Rev Cytol. 1980; 68:251-306. Review). The assay based on a quantitative sandwich-enzyme-immunoassay-principle using mouse monoclonal antibodies directed against DNA and histones, respectively. This allows the specific determination of mono- and oligonucleosomes which are released into the cytoplasm of cells which die from apoptosis. The sample (cell-lysate, serum, culture-supernatant etc.) was placed into a streptavidin-coated microplate. Subsequently, a mixture of anti-histone-biotin and anti-DNA-POD was added and incubated for 2 hours. During the incubation period, the anti-histone antibody binds to the histone-component of the nucleosomes and simultaneously fixes the immunocomplex to the streptavidin-coated microplate via its biotinylation. Additionally, the anti-DNA-POD antibody reacts with the DNA-component of the nucleosomes. After removal of unbound antibodies by a washing step, the amount of nucleosomes was quantified by the POD retained in the immunocomplex. POD was determined photometrically with ABTS (2,2'-Azino-di[3-ethyl-benz-thiazolin-sulfonat]) as substrate.

Example 8

Induction of Hypoxia

RPE cells were incubated in an incubator (Heracell, Kendro) maintained at 37° C. and 95% air, 5% $CO_2$ by vol (normoxic conditions) to 100% confluence (about $10^7$ cells/100-mm plate). Cells were then subjected to hypoxic conditions by placing them in an automatic $CO_2/O_2$ incubator (B 5061 EC/$O_2$, Kendro) maintained at 37° C. and $O_2$ levels ranging from 0 to 8%, 5% $CO_2$, 95 to 87% $N_2$ ($N_2$ to balance) for 1 h to 7 days. Uninduced cells remained in normoxic conditions. $PO_2$ and $PCO_2$ of the medium were measured in a blood gas analyzer (Corning model 178). Normoxic values were as follows: pH=7.2+/−0.1, $PO_2$=39.3+/−0.6 mmHg and $PCO_2$=131.5+/−0.9 mmHg. Hypoxic values were as follows: pH=7.2+/−0.1, $PO_2$=7 to 35+/−1.1 mmHg and $PCO_2$=14.9+/−1.2 mmHg (Liu et al., 1995; Palmer et al., 1998) (Liu Y, Cox S R, Morita T, Kourembanas S.: Hypoxia regulates vascular endothelial growth factor gene expression in endothelial cells. Identification of a 5' enhancer. Circ Res. 1995 September; 77(3):638-43; Palmer L A, Semenza G L, Stoler M H, Johns R A.: Hypoxia induces type II NOS gene expression in pulmonary artery endothelial cells via HIF-1. Am J. Physiol. 1998 February; 274(2 Pt 1):L212-9).

Example 9

Limitation of Essential Factors

The following example describes the cultivation of RPE cells in a modified Dulbecco's modified Eagle's medium (high glucose, Life Technologies, Inc.) for inducing stress in RPE cells by lacking essential factors. In normal RPE cell culture the cells grow in a modified Dulbecco's modified Eagle's medium. (high glucose, Life Technologies, Inc.) supplemented with 2% heat inactivated fetal calf serum (Roche), 100 units/ml penicillin, 100 μg/ml streptomycin, 1× non-essential amino acids, 2 mM L-glutamine, and 1 mM sodium pyruvate (all Life Technologies, Inc.) in a humidified atmosphere containing 5% $CO_2$ at 37° C. Normal cell culture media contains different anorganic salts and is added with vitamins, amino acids, glucose, nucleotides und many other substances. Most cells need for growing blood serum, such as fetal calf serum. The serum supplements proteins, hormones, growth factors, and intermediate products. For limiting these essential factors cells were cultured in a serum free medium. Additionally, a modified Dulbecco's modified Eagle's medium was used. The medium had no anorganic salts (e.g. KCl, NaCl), amino acids (e.g. L-glutamin, L-prolin), vitamins (e.g. biotin, riboflavin, folic acid) or other substances (e.g. glucose, lipon acid, nucleotides).

Example 10

Induction of Metabolic Acidose

The following example describes the induction of a metabolic acidose (pH<7.2+/−0.1) in cultured RPE cells by changing the pH value. Like in vivo, mammalia cell cultures need a pH optimum which is ranging from pH 7.2-7.4. Growing cells will cause a decrease of the pH-value due to lactate production. The pH value of the medium is measured in a blood gas analyzer (Corning model 178). Two ways were used to induce a metabolic acidose: Changing the $CO_2$ pressure (from 5% to 0%) in combination with leaking $HCO_3^-$ in the culture medium (Palmer et al., 1998) (Palmer L A, Semenza G L, Stoler M H, Johns R A.: Hypoxia induces type II NOS gene expression in pulmonary artery endothelial cells via HIF-1. Am J. Physiol. 1998 February; 274(2 Pt 1):L212-9) and the use of a modified Dulbecco's modified Eagle's medium containing 20 mM Hepes buffer. A Hepes buffer medium can be used for pH stress of cells because a medium buffered with Hepes is acidified in a humidified atmosphere containing 5% $CO_2$ at 37° C.

Example 11

RNA-Preparation from Cultured Primary RPE Cells

RNA prepared from primary RPE cells served as starting material for expression analyses for both real-time PCR and DNA-microarrays. After stress exposition (like hypoxic culture conditions, nutrient and/or growth factor deficiencies or pH changes) RPE cells were washed once with PBS prior to cell lysis. Approximately $1\times10^6$ cells (e.g. one well of a six well cell culture plate) were lyzed with 800 μl of β-mercaptoethanol containing RLT buffer (RNeasy Mini Kit from Qiagen Germany) by softly shaking the plate. Lysates were immediately frozen at −80° C. After thawing for 15 min at 37°

C. lysates were processed for isolation of total RNA according to the manufacturer's protocol (RNeasy Mini Kit, Qiagen). The RNA on the matrix of one column (according to $1\times10^6$ cells) was eluted with a suitable volume (10-100 µl) RNase free water. RNA from identically cultivated cells was pooled to yield uniform RNA from one culture condition.

Example 12

DNase I Digestion of Contaminating Genomic DNA

For subsequent analysis of RNA care should be taken to eliminate contaminating genomic DNA. Therefore digestion of genomic DNA via enzymatic restriction with DNA polymerase I (RNase free DNase I) was be performed. In brief a 100 µl reaction volume contained up to 50 µg RNA together with 20 µl of 25 mM $MgSO_4$ (final conc. 5 mM), 3.4 µl 3M NaAc pH 4.7 (final conc. 100 mM) and 20 U DNase I (2 µl of 10 U/µl stock e.g. from Roche Diagnostics). Digestion was performed for 1 h at 37° C. Subsequent purification of RNA from DNAse and restricted DNA fragments was carried out again by utilizing the RNeasy Mini Kit (Qiagen) according to the supplier's recommendations.

Example 13 cDNA Synthesis for Expression Analysis via Real-Time PCR

Synthesis of cDNA from total RNA is a prerequisite for expression analyses both by real-time PCR and microarray technique. To allow comparison of gene expression between mRNAs derived from different culture conditions the same amount of total RNA (here: e.g. 2 µg per different RNA) was reversely transcribed to cDNA by the following: 1 µl oligo-dT-primer (500 µg/ml, Qiagen-Operon, # 55000142), 2 µg RNA from porcine RPE cells, 1 µl 10 mM dNTP-mix (Invitrogen) and RNAse-free water (Qiagen) up to 12 µl in total. The mixture was incubated at 65° C. for 5 min followed by 2 min on ice. After brief centrifugation following kit components (Invitrogen, # 18064-014) were added: 4 µl 5× First Strand buffer, 2 µl 0.1 M DTT and 1 µl RNasin (40 U/µl, Promega, # N2511). After mixing by pipetting up and down the reaction was incubated for 2 min at 42° C. in a water bath. Then 1 µl reverse transcriptase (Superscript II, Invitrogen kit see above) was added and mixed by pipetting up and down. The reaction was incubated for 50 min at 42° C. in water bath and subsequently stopped by switching the reaction tube for 15 min to a 70° C. heat block. After short incubation on ice the newly synthesized cDNA was centrifuged and stored at −20° C. until use.

Example 14

Real-Time PCR

Concentrations of cDNA used as template in real-time PCR varied between 100 pg and 100 ng (referring to the original RNA). For each gene of interest and control genes specific TaqMan™ probes (containing a fluorescent dye and a quencher molecule) can be designed. Alternatively, the dye SYB®-Green can be used, which intercalates in all double stranded DNA molecules, allowing the in process measurement of arising PCR products. Oligonucleotides for PCR amplification (in real-time PCR and microarray analysis) were designed to achieve PCR fragments of usually 150-600 base pairs (bp) in size. Along with the gene(s) of interest PCR probes were set up in duplicate or triplicate together with control or housekeeping genes like beta-actin (ACTB), glyceraldehyde 3-phosphate dehydrogenase (GAPD) or hypoxanthine phosphoribosyltransferase (HPRT1). A typical 25 µl PCR reaction was composed like the following: Template cDNA (100 pg-100 ng), HotStart Taq-polymerase (e.g. Invitrogen) 0.5 U/µl, 1× polymerase reaction buffer, 0.2 mM of each dNTP (e.g. Invitrogen), 1.5 to 7 mM $MgCl_2$ (e.g. Invitrogen), oligonucleotides in the range between 50-300 nM (e.g. Qiagen-Operon, Germany) and SYBR®-Green (e.g. Bio Whittaker Molecular Applications, # 50512, 10,000× conc.) 0.1-0.5× (diluted from stock). Typical PCR conditions for real-time PCR were: 5-15 min activation step at 95° C., 45 cycles with each 30 s denaturation at 94° C., annealing of primers (temperature depending on melting temperature of primers) for 30 s and elongation of primers at 72° C. for up to 1 min. After each cycle the increase in fluorescence of the probe during PCR amplification was determined by the optical unit of the real-time PCR device (e.g. icycler from BIO-RAD). The data from real-time PCR generated from control versus treated sample gave a profound information about changes in mRNA expression.

Example 15

PCR Amplification of Target Genes for Spotting on Microarray Slides

From all selected target genes PCR fragments of 150-600 bp were amplified from RPE-/retina- or liver-specific cDNA (as templates) according to the following protocol: PCR reactions were typically set up in a total of 50 µl. They usually contained 1× polymerase reaction buffer (e.g. Invitrogen), 1.5-4 mM (final concentration) $MgCl_2$ (e.g. Invitrogen), 0.2 mM of each nucleotide (10 mM dNTP stock, e.g. Invitrogen), up to 1 µM of gene specific forward and reverse primer (Qiagen Operon), 0.025-1 U Taq polymerase (e.g. Invitrogen), a suitable amount of template cDNA (1-10 µl, depending on cDNA quality) and nuclease free water to a final volume of 50 µl. Typical conditions for PCR were: a single 5 min denaturation step at 95° C., 30 cycles with each 30 s denaturation at 94° C., annealing of primers (usually between 45°-65° C., temperature depending on melting temperature of primers) for 30 s and elongation of primers at 72° C. for up to 1 min.

Example 16

PCR Purification

PCR purification was performed by utilizing the QiaQuick Purification Kit (Qiagen) according to the manufacturer's recommendations.

Example 17

Spotting of PCR-Products on Coated Glass-Slides

DNA from PCR products was arrayed with splitted pins (Telechem) on CMT GAPS coated slides (Corning) with a Genepak spotter (Genetix) using 50% DMSO as spotting buffer. Spotted slides were stored for up to 6 months.

Example 18

Labeling of RNAs for Hybridization

For each labeling reaction 5 µg of RNA (at least 300 ng/µl, $OD_{260/280}$ between 1.8 and 2.0) are recommended. Direct labeling of control RNA (from control/untreated cells) and test RNA (from stressed/treated cells) with Cy3 and Cy5 (supplied from Amersham Biosciences or Perkin Elmer) was done with the Qiagen kit 'Label Star' according to the supplier's protocol.

Example 19

Hybridization of RNAs with Microarray

Hybridization of mixed RNAs with the spotted DNA on the microarrays was performed at 42° C. overnight on a automated Lucidea Slidepro hybridization station (Amersham Biosciences) under well defined hybridization and washing conditions: Hybridization buffer was composed of 25% formamide, 5×SSC und 0.1% SDS.

Example 20

Image Processing and Data Analysis of Arrays

After hybridization the signals on the microarrays were scanned with a laser scanner. (ScanArray 4000, Perkin Elmer) to yield the raw image data. To extract the signal information from above generated images into tab delimited text files software tools like ScanAlyze (Mike Eisen, Stanford University, CA., http://rana.lbl.gov/EisenSoftware.htm) were applied. Normalization of data was done by applying Microsoft's Excel and Access programs (part of Microsoft Office packages). Such prepared data were analyzed with software programs like GeneSpring from Silicon Genetics, which enable e.g. complex cluster analysis to find differentially expressed genes.

Example 21

Inhibition of the Expression of Green Fluorescent Protein (eGFP) in the Retinal Pigment Epithelium (RPE) and the Retina of Transgenic Mice by dsRNA Molecules This example describes specific post transcriptional gene silencing by dsRNA of the target gene eGFP in the mouse animal model, during which the optimal dsRNA concentration for post transcriptional gene silencing on systemic application is to be determined (experimental procedure 1, results see FIG. 1). The procedure involves the in vivo treatment of transgenic mice (FVB.Cg-Tg(GFPU)5Nagy, The Jackson Laboratory), which express the enhanced form of green fluorescent protein (eGFP) in their body cells, by systemic application of dsRNA oligoribonucleotide molecules against the target gene eGFP. Control animals are also treated systemically with non-silencing dsRNA molecules. For the purpose of post transcriptional gene silencing, the animals not under analgesic or anesthetic influence receive daily i.v. tail vein injections ($1^{st}$ day of treatment: day 0, final day of treatment: day 20) of 100 or 200 μg eGFP-specific dsRNA/kg body weight (BW) and the control group of 200 μg non-silencing dsRNA/kg BW. A control group of animals treated with buffer (daily i.v. injection of 0.1 ml buffer into the tail vein) is also kept. Each group of experimental animals consists of 8 animals, the maximum injection volume/injection being 0.1 ml. On day 21, the animals are sacrificed by $CO_2$ inhalation.

The expression of green fluorescent protein in the eye of the mice is examined immunohistologically (spontaneous eGFP fluorescence: fluorescence microscopic evaluation; eGFP-specific immunofluorescence staining: fluorescence microscopic evaluation).

dsRNA Constructs and Plasmids:

For the design of the dsRNA molecules, sequences of the type AA(N19)TT (where N represents any nucleotide) were selected from the sequence of the target mRNA, in order to obtain 21 nucleotide (nt) long sense and antisense strands with symmetrical 3'-overhangs of two nucleotides in length. In the 3'-overhangs, 2'-deoxy-thymidine was used instead of uridine. In order to ensure that the dsRNA molecules are exclusively directed against the target gene, the chosen dsRNA sequences are tested against the mouse genome in a BLAST analysis. The 21-nt RNA molecules are synthesized chemically and purified. For the duplex formation, 100 μg of the sense and antisense oligoribonucleotides each are mixed in 10 mM Tris/HCl, 20 mM NaCl (pH 7.0) and heated to 95° C. and cooled to room temperature over a period of 18 hours. The dsRNA molecules are precipitated from ethanol and resuspended in sterile buffer (100 mM potassium acetate, 30 mM HEPES-KOH, 2 mM magnesium acetate, pH 7.4). The integrity and double strand character of the dsRNA are verified by gelelectrophoresis. Alternatively, the dsRNA molecules are obtained from commercial suppliers. The sequences of the target genes and the corresponding dsRNA molecules are as follows:

```
DNA target sequence:
5'G CAA GCT GAC CCT GAA GTT CA    (SEQ ID NO 5)
Coding region, 121-141 relative
to the first nucleotide of the
start codon (Acc. No. U55761)

dsRNA (sense)
5'r(GCA AGC UGA CCC UGA AGU U)    (SEQ ID NO 6)

dsRNA (antisense)
5'r(AA CUU CAG GGU CAG CUU GC)    (SEQ ID NO 7)
```

Non-Silencing dsRNA, Control

```
DNA target sequence:
5'AATTCTCCGAACGTGTCACGT          (SEQ ID NO 8)

dsRNA (sense)
5'r(UUCUCCGAACGUGUCACGU)d(TT)    (SEQ ID NO 9)

dsRNA (antisense)
5'r(ACGUGACACGUUCGGAGAA)d(TT)    (SEQ ID NO 10)
```

Analgesia and Anesthesia of the Mice:

For systemic application, the animals are immobilized and the dsRNAs are injected i.v. in the tail vein (maximal injection volume: 0.1 ml), where analgesia or anesthesia are refrained from, since this would put more stress on the animals than the i.v. injection itself. For retrobulbar injection (maximal injection volume: 0.005 ml) the animals are however subjected to short-term isofluorane inhalation anaesthesia and provided with Metamizole sodium for analgesic purposes. The animals are then kept in their accustomed animal cage surroundings. After completion of in vivo diagnosis (the end of each animal experiment is stated respectively in example 1-5) the animals are killed by $CO_2$ inhalation, enucleated and the eyes are studied histologically (immunohistology).

Study of eGFP Expression in Retinal Pigment Epithelium and Retina:

After removal, the eyes are fixed in 4% formalin/PBS solution for 24 hours. Using standard methods, the fixed samples are subsequently dehydrated in a series of increasing alcohol and embedded in paraffin. With the aid of a microtome, standard 5 to 12 μm serial slices are produced, stretched in a heated water bath and transferred to a polylysin-coated cover slip. The sections are then dried in an incubator for 2 hours at a temperature of 52° C. The dried sections are deparaffinated in xylol, transferred to a decreasing series of alcohol followed by Tris/HCl pH 7.4. After blocking, the sections are incubated for 2 hours with primary anti-eGFP antiserum (polyclonal goat anti-eGFP antiserum, Santa Cruz No. sc-5384). Detection occurs by means of immunofluorescence staining by using a Cy2-conjugated rabbit anti-goat IgG (Dianova, No. 305-225-045). The samples are embedded and then mounted for microscopy with an Eclipse TE-2000-S microscope (Nikon), equipped with a 20× and 40×/1.3 objective. The spontaneous, eGFP-specific fluorescence in deparaffinated, untreated sections is analyzed using a fluorescence microscope.

Experimental procedure: Systemic siRNA application. Determination of optimal dsRNA concentration for post transcriptional gene silencing.

| Group | Substance | Number of animals |
|---|---|---|
| Control animals | Buffer | 8 |
| Negative control 200 μg dsRNA/kg BW | non- silencing dsRNA | 8 |
| 200 μg dsRNA/kg BW | eGFP-specific dsRNA | 8 |
| 100 μg dsRNA/kg BW | eGFP-specific dsRNA | 8 |
| Animals per experiment | | 32 |

For results see FIG. 1

| Genname | Accession No | marker for | CDS | Description | Alternative Symbols | Citation |
|---|---|---|---|---|---|---|
| BAX | NM_138761 | apoptosis | 53 . . . 631 | BCL2-associated X protein (BAX), transcript variant alpha | unknown | Martindale et al. J Cell Physiol. 2002 Jul; 192(1): 1-15. |
| BBC3 | NM_014417 | apoptosis | 1 . . . 582 | BCL2 binding component 3 (BBC3) | JFY1, PUMA, PUMA/JFY1 | Martindale et al. J Cell Physiol. 2002 Jul; 192(1): 1-15. |
| BCL2 | NM_000633 | apoptosis | 32 . . . 751 | B-cell CLL/lymphoma 2 (BCL2), transcript variant alpha | unknown | Nicotera. Toxicol Lett. 2002 Feb 28; 127(1-3): 189-95. |
| BIRC2 | NM_001166 | apoptosis | 1160 . . . 3016 | baculoviral IAP repeat-containing 2 (BIRC2) | API1, MIHB, CIAP1, HIAP2 | Martindale et al. J Cell Physiol. 2002 Jul; 192(1): 1-15. |
| BIRC3 | NM_001165 | apoptosis | 725 . . . 2539 | baculoviral IAP repeat-containing 3 (BIRC3) | AP12, MIHC, CIAP2, HAIP1, HIAP1 | Martindale et al. J Cell Physiol. 2002 Jul; 192(1): 1-15. |
| BIRC4 | NM_001167 | apoptosis | 34 . . . 1527 | baculoviral IAP repeat-containing 4 (BIRC4) | ILP, API3, ILP1, MIHA, XIAP, Xiap, hILP, ILP-1 | Martindale et al. J Cell Physiol. 2002 Jul; 192(1): 1-15. |
| CDKN1A | NM_078467 | apoptosis | 236 . . . 730 | cyclin-dependent kinase inhibitor 1A (p21, Cip1) (CDKN1A), transcript variant 2 | P21, CIP1, SDI1, WAF1, CAP20, CDKN1, MDA-6 | Almond & Cohen. Leukemia. 2002 Apr; 16(4): 433-43. |
| ENDOG | NM_004435 | apoptosis | 167 . . . 1060 | endonuclease G (ENDOG) | unknown | Almond & Cohen. Leukemia. 2002 Apr; 16(4): 433-43. |
| HSPD1 | NM_002156 | apoptosis | 25 . . . 1746 | heat shock 60 kDa protein 1 (chaperonin) (HSPD1) | GROEL, HSP60, SPG13 | Martindale et al. J Cell Physiol. 2002 Jul; 192(1): 1-15. |
| HSPE1 | NM_002157 | apoptosis | 42 . . . 350 | heat shock 10 kDa protein 1 (chaperonin 10) (HSPE1) | CPN10, GROES, HSP10 | Ravagnan et al. J Cell Physiol. 2002 Aug; 192(2): 131-7. |
| LRDD | NM_145886 | apoptosis | 144 . . . 2876 | leucine-rich and death domain containing (LRDD), transcript variant 1 | PIDD, MGC16925 | Martindale et al. J Cell Physiol. 2002 Jul; 192(1): 1-15. |
| MCL1 | NM_021960 | apoptosis | 64 . . . 1116 | myeloid cell leukemia sequence 1 (BCL2-related) (MCL1) | EAT | Bae et al. J. Biol. Chem. 275: 25255-25261, 2000. |
| P53AIP1 | AB045830 | apoptosis | 211 . . . 585 | for p53AIP1, complete cds | unknown | Martindale et al. J Cell Physiol. 2002 Jul; 192(1): 1-15. |

-continued

| Genname | Accession No | marker for | CDS | Description | Alternative Symbols | Citation |
|---|---|---|---|---|---|---|
| PMAIP1 | NM_021127 | apoptosis | 174 . . . 338 | phorbol-12-myristate-13-acetate-induced protein 1 (PMAIP1) | APR, NOXA | Martindale et al. J Cell Physiol. 2002 Jul; 192(1): 1-15. |
| TNFRSF10B | NM_147187 | apoptosis | 286 . . . 1521 | tumor necrosis factor receptor superfamily, member 10b (TNFRSF10B), transcript variant 2 | DR5, KILLER, TRICK2, TRICKB, ZTNFR9, TRAILR2, TRICK2A, TRICK2B, TRAIL-R2, KILLER/DR5 | Martindale et al. J Cell Physiol. 2002 Jul; 192(1): 1-15. |
| TNFRSF6 | NM_000043 | apoptosis | 347 . . . 1354 | tumor necrosis factor receptor superfamily, member 6 (TNFRSF6), transcript variant 1,. | FAS, APT1, CD95, APO-1, FASTM | Hueber. Nature Cell Biol. 2: E23-E25, 2000. |
| TOP2B | NM_001068 | apoptosis | 1 . . . 4866 | topoisomerase (DNA) II beta 180 kDa (TOP2B) | TOPIIB | Solovyan et al. J Biol Chem. 2002 Jun 14; 277(24): 21458-67. |
| TP53 | NM_000546 | apoptosis | 252 . . . 1433 | tumor protein p53 (Li-Fraumeni syndrome) (TP53), | P53, p53, TRP53 | Almond & Cohen. Leukemia. 2002 Apr; 16(4): 433-43. |
| EPO | NM_000799 | hypoxic cult.cond | 182 . . . 763 | erythropoietin (EPO),. | EP | Grimm et al. Nature Med. 8: 718-724, 2002. |
| FGF2 | NM_002006 | hypoxic cult.cond | 302 . . . 934 | fibroblast growth factor 2 (basic) (FGF2), | BFGF, FGFB, HBGH-2 | Grimm et al. Nature Med. 8: 718-724, 2002. |
| LDHA | NM_005566 | hypoxic cult.cond | 98 . . . 1096 | lactate dehydrogenase A | unknown | Semenza et al. J Biol Chem. 1996 Dec 20;271(51): 32529-37. |
| NGB | NM_021257 | hypoxic cult.cond | 376 . . . 831 | neuroglobin (NGB),. | unknown | Burmester et al. Nature 407 (6803), 520-523 (2000) |
| VEGF | NM_003376 | hypoxic cult.cond | 702 . . . 1277 | vascular endothelial growth factor (VEGF), | VEGFA | Grimm et al. Nature Med. 8: 718-724, 2002. |
| AVEN | NM_020371 | oxidative stress | 53 . . . 1141 | apoptosis, caspase activation inhibitor (AVEN),. | PDCD12 | Martindale et al. J Cell Physiol. 2002 Jul; 192(1): 1-15. |
| BCL2A1 | NM_004049 | oxidative stress | 184 . . . 711 | BCL2-related protein A1 (BCL2A1),. | GRS, BFL1, HBPA1, BCL2L5 | Martindale et al. J Cell Physiol. 2002 Jul; 192(1): 1-15. |
| CAT | NM_001752 | oxidative stress | 69 . . . 1652 | catalase (CAT), | unknown | Cai et al. Prog Retin Eye Res. 2000 Mar; 19(2): 205-21. |
| DUSP1 | NM_004417 | oxidative stress | 249 . . . 1352 | dual specificity phosphatase 1 (DUSP1),. | HVH1, CL100, MKP-1, PTPN10 | Wu et al. J Biol Chem. 2002 Nov 15; 277(46): 44208-13. |
| GADD45 | NM_001924 | oxidative stress | 296 . . . 793 | growth arrest and DNA-damage-inducible, alpha (GADD45A),. | DDIT1, GADD45 | Martindale et al. J Cell Physiol. 2002 Jul; 192(1): 1-15. |
| HMOX1 | NM_002133 | oxidative stress | 81 . . . 947 | heme oxygenase (decycling) 1 (HMOX1), | HO-1, bK286B10 | Martindale et al. J Cell Physiol. 2002 Jul; 192(1): 1-15. |
| IL6 | NM_000600 | oxidative stress | 63 . . . 701 | interleukin 6 (interferon, beta 2) (IL6) | HGF, HSF, BSF2, IL-6, IFNB2 | Martindale et al. J Cell Physiol. 2002 Jul; 192(1): 1-15. |
| MAP2K6 | NM_002758 | oxidative stress | 341 . . . 1345 | mitogen-activated protein kinase kinase 6 (MAP2K6), transcript variant 1 | MEK6, MKK6, MAPKK6, PRKMK6, SAPKK3 | Seger & Krebs. FASEB J. 9: 726-735, 1995. |
| MAPK8 | NM_139049 | oxidative stress | 18 . . . 1301 | mitogen-activated protein kinase 8 (MAPK8), transcript variant 1 | JNK, JNK1, PRKM8, SAPK1, JNK1A2, JNK21B1/2 | Almond & Cohen. Leukemia. 2002 Apr; 16(4): 433-43. |
| MAPK9 | NM_002752 | oxidative stress | 50 . . . 1324 | mitogen-activated protein kinase 9 (MAPK9), transcript variant 1 | JNK2, JNK2A, JNK2B, PRKM9, JNK-55, JNK2BETA, P54ASAPK, | Martindale et al. J Cell Physiol. 2002 Jul; 192(1): 1-15. |

-continued

| Genname | Accession No | marker for | CDS | Description | Alternative Symbols | Citation |
|---|---|---|---|---|---|---|
| | | | | | p54aSAPK, JNK2ALPHA | |
| NFKB2 | NM_002502 | oxidative stress | 164 . . . 2965 | nuclear factor of kappa light polypeptide gene enhancer in B-cells 2 (p49/p100) (NFKB2), | LYT10, LYT-10 | Martindale et al. J Cell Physiol. 2002 Jul; 192(1): 1-15. |
| PRDX2 | NM_005809 | oxidative stress | 90 . . . 686 | peroxiredoxin 2 (PRDX2),. | PRP, TSA, NKEFB, TDPX1 | Fujii & Ikeda. Redox Rep. 2002; 7(3): 123-30. Review. |
| SFN | NM_006142 | oxidative stress | 166 . . . 912 | stratifin (SFN), | unknown | Martindale et al. J Cell Physiol. 2002 Jul; 192(1): 1-15. |
| SHC1 | NM_003029 | oxidative stress | 195 . . . 1946 | SHC (Src homology 2 domain containing) transforming protein 1 (SHC1), | SHC, SHCA | Martindale et al. J Cell Physiol. 2002 Jul; 192(1): 1-15. |
| SOD1 | NM_000454 | oxidative stress | 1 . . . 465 | superoxide dismutase 1, soluble (amyotrophic lateral sclerosis 1 (adult)) (SOD1), | ALS, ALS1, IPOA | Martindale et al. J Cell Physiol. 2002 Jul; 192(1): 1-15. |
| SOD2 | NM_000636 | oxidative stress | 5 . . . 673 | superoxide dismutase 2, mitochondrial (SOD2), | IPO-B, MNSOD | Martindale et al. J Cell Physiol. 2002 Jul; 192(1): 1-15. |
| TNFAIP3 | NM_006290 | oxidative stress | 67 . . . 2439 | tumor necrosis factor, alpha-induced protein 3 (TNFAIP3), | A20, TNFA1P2 | Martindale et al. J Cell Physiol. 2002 Jul; 192(1): 1-15. |
| TRAF1 | NM_005658 | oxidative stress | 79 . . . 1329 | TNF receptor-associated factor 1 (TRAF1), | EBI6, MGC:10353 | Martindale et al. J Cell Physiol. 2002 Jul; 192(1): 1-15. |
| TRAF2 | NM_021138 | oxidative stress | 58 . . . 1563 | TNF receptor-associated factor 2 (TRAF2), transcript variant 1, | TRAP, TRAP3, MGC:45012 | Martindale et al. J Cell Physiol. 2002 Jul; 192(1): 1-15. |

REFERENCES

Banks C N, Hutton W K. Blindness in New South Wales: an estimate of the prevalence and some of the contributing causes. Aust J Ophthalmol 9:285-288 (1981).

Bohler C, Nielsen P E, Orgel L E. Template switching between PNA and RNA oligonucleotides. Nature. 376(6541):578-81 (1995).

Bernstein E, Caudy A A, Hammond S M, Hannon G J. Role for a bidentate ribonuclease in the initiation step of RNA interference. Nature 409(6818):363-6 (2001).

Bressler N M. Early detection and treatment of neovascular age-related macular degeneration.) J Am Board Fam Pract. 15:142-152 (2002).

Bressler N M, Bressler S B. Preventative ophthalmology. Age-related macular degeneration. Ophthalmology 102: 1206-1211 (1995).

Bressler N M, Bressler S B, Fine S L. Age-related macular degeneration. Surv Ophthalmol 32:375-413 (1988).

Bressler S B, Bressler N M, Fine S L, Hillis A, Murphy R P, Olk R J, Patz A. Natural course of choroidal neovascular membranes within the foveal avascular zone in senile macular degeneration. Am J Ophthalmol 93:157-163 (1982).

Campochiaro P A, Soloway P, Ryan S J, Miller J W. The pathogenesis of choroidal neovascularization in patients with age-related macular degeneration. Mol Vis. 5:34 (1999).

Caplen N. J., Parrish S., Imani F., Fire A., and Morgan R. A. Specific inhibition of gene expression by small double-stranded RNAs in invertebrate and vertebrate systems. Proc. Natl. Acad. Sci. 09:9742-9747 (2001).

Davis L G, Kuehl M, Kuehl M W, Battey J F. Basic methods in molecular biology. Sec. Ed. Elsevier (1990).

Elbashir S. M., Harborth J., Lendeckel W., Yalcin A., Weber K., and Tuschel T. Duplexes of 21-nucleotide RNAs mediate RNA interference in cultured mammalian cells. Nature 411: 494-498 (2001).

Feeney L. Lipofuscin and melanin of human retinal pigment epithelium. Fluorescence, enzyme cytochemical, and ultrastructural studies. Invest Ophthalmol Vis Sci 17:583-600 (1978).

Feeney-Burns L, Ellersieck M R. Age-related changes in the ultrastructure of Bruch's membrane. Am J Ophthalmol 100:686-697(1985).

Finn P J, Gibson N J, Fallon R, Hamilton A, Brown T. Synthesis and properties of DNA-PNA chimeric oligomers. Nucleic Acids Res. 24: 3357-3363 (1996).

Fire A., Xu S., Montgomery M. K., Kostas S. A., Driver S. E., and Mello C. C. Potent and specific genetic interference by double-stranded RNA in *Coenorhabditis elegans*. Nature 391:806-811(1998).

Fischer S G, Lerman L S. DNA fragments differing by single base-pair substitutions are separated in denaturing gradient gels: correspondence with melting theory. Proc Natl Acad Sci USA. 80(6):1579-83 (1983).

Gass J D. Drusen and disciform macular detachment and degeneration. Arch Ophthalmol 90:206-217 (1973).

Gass J D. Pathogenesis of disciform detachment of the neuroepithelium. Am J Ophthalnol 63: Suppl:1-139(1967).

Ghafour I M, Allan D, Foulds W S. Common causes of blindness and visual handicap in the west of Scotland. Br J Ophthalmol 67: 209-213 (1983).

Gossen M, Bonin A L, Freundlieb S, Bujard H. Inducible gene expression systems for higher eukaryotic cells. Curr Opin Biotechnol. 5(5):516-20 (1994).

Gossen M, Bujard H. Tight control of gene expression in mammalian cells by tetracycline-responsive promoters. Proc Natl Acad Sci USA. 89(12):5547-5551 (1992).

Gotoh M, Hasebe M, Ohira T, Tosu M. [Gene diagnosis with an affinity sensor, BIACORE—principle and applications]. Rinsho Byori. 45(3):224-8 (1997). Japanese.

Green W R, McDonnell P J, Yeo J H. Pathologic features of senile macular degeneration. Ophthalmology 92:615-27 (1985).

Grey R H, Burns-Cox C J, Hughes A. Blind and partial sight registration in Avon. Br J Ophthalmol 73:88-94(1989).

Grishok A, Pasquinelli A E, Conte D, Li N, Parrish S, Ha I, Baillie D L, Fire A, Ruvkun G, Mello C C. Genes and mechanisms related to RNA interference regulate expression of the small temporal RNAs that control *C. elegans* developmental timing. Cell 106(1):23-34 (2001).

Hamilton A J and Baulcombe D C. A species of small antisense RNA in posttranscriptional gene silencing in plants. Science 286: 950-952(1999).

Heiba I M, Elston R C, Klein B E, Klein R. Sibling correlations and segregation analysis of age-related maculopathy: the Beaver Dam Eye Study. Genet Epidemiol 11:51-67 (1994).

Hogan M J, Alvarado J. Studies on the human macula. IV. Aging changes in Bruch's membrane. Arch Ophthalmol 77:410-420(1967).

Hyman L G, Lilienfeld A M, Ferris F L, Fine S L. Senile macular degeneration: a case-control study. Am J Epidemiol 118:213-227 (1983).

Hyman L. Epidemiology of eye disease in the elderly. Eye 1: 330-341 (1987).

Jalkanen M, Nguyen H, Rapraeger A, Kurn N, Bernfield M. Heparan sulfate proteoglycans from mouse mammary epithelial cells: localization on the cell surface with a monoclonal antibody. J. Cell Biol. 101(3):976-984 (1985).

Jalkanen M, Rapraeger A, Saunders S, Bernfield M. Cell surface proteoglycan of mouse mammary epithelial cells is shed by cleavage of its matrix-binding ectodomain from its membrane-associated domain. J. Cell Biol. 105:3087-96 (1987).

Jensen K K, Orum H, Nielsen P E, Norden B. Kinetics for hybridization of peptide nucleic acids (PNA) with DNA and RNA studied with the BIAcore technique. Biochemistry 36(16):5072-5077 (1997).

Joyner A. Gene Targeting, A Practical Approach, Second edition, Oxford University Press (1999).

Kasschau K D and Carrington J C. A counterdefensive strategy of plant viruses: suppression of posttranscriptional gene silencing. Cell 95:461-470(1998).

Klein R, Klein B E, Franke T. The relationship of cardiovascular disease and its risk factors to age-related maculopathy. The Beaver Dam Eye Study. Ophthalmology 100:406-414 (1993).

Knight S W and Bass B L. A role for the RNase III enzyme DCR-1 in RNA interference and germ line development in *Caenorhabditis elegans*. Science 2: 2269-2271(2001).

Koch T, Hansen H F, Andersen P, Larsen T, Batz H G, Otteson K, Orum H. Improvements in automated PNA synthesis using Boc/Z monomers. J Pept Res. 49(1):80-8 (1997).

Köhler G, Milstein C. Continuous cultures of fused cells secreting antibody of predefined specificity. Nature 256 (5517):495-497 (1975).

Leibowitz H M, Krueger D E, Maunder L R, Milton R C, Kini M M, Kahn H A, Nickerson R J, Pool J, Colton T L, Ganley J P, Loewenstein J I, Dawber T R. The Framingham Eye Study monograph: An ophthalmological and epidemiological study of cataract, glaucoma, diabetic retinopathy, macular degeneration, and visual acuity in a general population of 2631 adults, 1973-1975. Surv Ophthalmol 24(Suppl): 335-610 (1980).

Le Mouellic H, Lallemand Y, Brulet P. Targeted replacement of the homeobox gene Hox-3.1 by the *Escherichia coli* lacZ in mouse chimeric embryos. Proc Natl Acad Sci USA. 87(12):4712-4716 (1990).

Maguire P, Vine A K. Geographic atrophy of the retinal pigment epithelium. Am J Ophthalmol 102:621-625 (1986).

Mantero G, Zonaro A, Albertini A, Bertolo P, Primi D. DNA enzyme immunoassay: general method for detecting products of polymerase chain reaction. Clin Chem. 37(3):422-429 (1991).

Mayer R J, Walker J H, eds. Immunochemical methods in cell and molecular biology. Academic Press, London (1987).

Melani C, Rivoltini L, Parmiani G, Calabretta B, Colombo M P. Inhibition of proliferation by c-myb antisense oligodeoxynucleotides in colon adenocarcinoma cell lines that express c-myb. Cancer Res. 51:2897-2901 (1991)

Meyers S M, Zachary A A. Monozygotic twins with age-related macular degeneration. Arch Ophthalnol 106:651-653 (1988).

Paetkau M E, Boyd T A, Grace M, Bach-Mills J, Winship B. Senile disciform macular degeneration and smoking. Can J Ophthalmol 13:67-71 (1978).

Pauleikhoff D, Harper C A, Marshall J, Bird A C. Aging changes in Bruch's membrane. A histochemical and morphologic study. Ophthalmology 97:171-178(1990).

Piguet B, Wells J A, Palmvang I B, Wormald R, Chisholm I H, Bird A C. Age-related Bruch's membrane change: a clinical study of the relative role of heredity and environment. Br J Ophthalmol 77:400-403 (1993).

Sambrook et al., Molecular Cloning, A Laboratory Manual, $2^{nd}$ edition (1989) Cold Spring Harbor Laboratory Press, Cold Spring Harbor, N.Y.

Sarks S H. Ageing and degeneration in the macular region: a clinico-pathological study. Br J Ophthalmol 60:324-341 (1976).

Schuler G D. Pieces of the puzzle: expressed sequence tags and the catalog of human genes. J Mol Med. 75(10):694-8 (1997)

Seddon J M, Ajani U A, Mitchel B D. Fainilial aggregation of age-related maculopathy. Am J Ophthalmol 123: 199-206 (1997).

Smith and Johnson. Single-step purification of polypeptides expressed in *Escherichia coli* as fusions with glutathione S-transferase. Gene 67:3140 (1988)

Silvestri G, Johnston P B, Hughes A E. Is genetic predisposition an important risk factor in age-related macular degeneration? Eye 8:564-568 (1994).

Sobol R E, Astarita R W, Chisari F V, Griffiths J C, Royston I. Use of immunoglobulin light chain analysis to detect bone marrow involvement in B-cell neoplasms. Clin Immunol Immunopathol. 24(1):139-144 (1982).

Sobol R E, Dillman R O, Collins H, Griffiths J C, Green M R, Royston I. Applications and limitations of peripheral blood lymphocyte immunoglobulin light chain analysis in the evaluation of non-Hodgkin's lymphoma. Cancer 56(8): 2005-2010 (1985).

Sperduto R D, Hiller R. Systemic hypertension and age-related maculopathy in the Framingham Study. Arch Ophthalmol 104:216-219 (1986).

Steinecke, Ribozymes, Methods in Cell Biology 50, Galbraith et al. eds Academic Press, Inc.: 449-460 (1995).

The Eye Disease Case-Control Study Group. Risk factors for neovascular age-related macular. Arch Ophthalmol 110: 1701-1708 (1992).

Tijssen P.; Burden, R H and von Knippenburg (Eds). Practice and theory of enzyme immuno-assays. Elsevier, Amsterdam, Vol. 15 (1985).

Verma R. S.; Babu A. Human chromosomes; Manual of basic techniques. New York, Pergamon Press (1989).

Veselkov A G, Demidov V V, Frank-Kamenetskii M, Nielsen P E. PNA as a rare genome-cutter. Nature. 379(6562):214 (1996).

Wahl R L, Parker C W, Philpott G W. Improved radioimaging and tumor localization with monoclonal F(ab')2. J Nucl Med. 24(4):316-25 (1983).

Weiler J, Gausepohl H, Hauser N, Jensen O N, Hoheisel J D. Hybridisation based DNA screening on peptide nucleic acid (PNA) oligomer arrays. Nucleic Acids Res. 25(14): 2792-9 (1997).

Yap M, Weatherill J. Causes of blindness and partial sight in the Bradford Metropolitan District from 1980 to 1985. Ophthalmic Physiol Opt 9:289-292 (1989).

Yuzawa M, Isomae T, Mori R, Shimada H, Utsunomiya I. Surgical excision versus laser photocoagulation for subfoveal choroidal neovascular membrane with age-related macular degeneration: comparison of visual outcomes. Jpn J Ophthalmol. 45(2):192-8 (2001).

Zamore P D, Tuschl T, Sharp P A, Bartel D P. RNAi: double-stranded RNA directs the ATP-dependent cleavage of mRNA at 21 to 23 nucleotide intervals. Cell 101: 25-33 (2000).

The invention claimed is:

1. A method for the treatment of autosomal recessive retinitis pigmentosa or congenital stationary night blindness comprising:

administering to a subject a therapeutically effective amount of a composition comprising a dsRNA between 21 and 23 nucleotides in length and a carrier, said dsRNA having a nucleotide sequence corresponding to mRNA of a target gene expressed in the eye; said administering of the composition occurring outside the blood-retina barrier, said composition inhibiting the target gene by RNA interference inside the eye, thereby treating autosomal recessive retinitis pigmentosa or congenital stationary night blindness, and wherein said target gene is SEQ ID NO:1 or SEQ ID NO:3.

2. The method of claim 1, wherein said autosomal recessive retinitis pigmentosa or congenital stationary night blindness is related to angiogenesis and/or neovascularization.

3. The method of claim 1, wherein said autosomal recessive retinitis pigmentosa or congenital stationary night blindness is related to the retinal pigment epithelium (RPE), neurosensory retina, choroid, and a combination thereof.

4. The method of claim 1, wherein the dsRNA comprises a terminal 3'-hydroxyl group.

5. The method of claim 1, further comprising preparing the dsRNA.

6. The method of claim 1, further comprising diagnosing a subject with autosomal recessive retinitis pigmentosa or congenital stationary night blindness or a predisposition to autosomal recessive retinitis pigmentosa or congenital stationary night blindness.

7. The method of claim 1, further comprising isolating the target gene.

8. The method of claim 1, wherein said administering is by systemic administration.

* * * * *